(12) United States Patent
Stieber et al.

(10) Patent No.: US 8,435,986 B2
(45) Date of Patent: May 7, 2013

(54) BICYCLIC TRAIZOLE DERIVATIVES FOR TREATING OF TUMORS

(75) Inventors: Frank Stieber, Heidelberg (DE); Oliver Schadt, Rodenbach (DE); Dieter Dorsch, Ober-Ramstadt (DE); Andree Blaukat, Schriesheim (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 162 days.

(21) Appl. No.: 13/059,016

(22) PCT Filed: Jul. 16, 2009

(86) PCT No.: PCT/EP2009/005172
§ 371 (c)(1),
(2), (4) Date: Feb. 14, 2011

(87) PCT Pub. No.: WO2010/017870
PCT Pub. Date: Feb. 18, 2010

(65) Prior Publication Data
US 2011/0135600 A1   Jun. 9, 2011

(30) Foreign Application Priority Data

Aug. 14, 2008 (DE) .......................... 10 2008 037 790

(51) Int. Cl.
*A61K 31/535* (2006.01)
*A61K 31/4965* (2006.01)
*C07D 471/04* (2006.01)
*C07D 413/14* (2006.01)

(52) U.S. Cl.
USPC ................. 514/234.2; 514/255.05; 544/117; 544/350

(58) Field of Classification Search ............... 514/234.2, 514/255.05; 544/117, 350
See application file for complete search history.

(56) References Cited

U.S. PATENT DOCUMENTS

| | | | |
|---|---|---|---|
| 6,242,461 B1 | 6/2001 | Goldstein | |
| 6,403,586 B1 | 6/2002 | Ohkuchi et al. | |
| 8,071,593 B2 | 12/2011 | Schadt et al. | |
| 8,173,653 B2 | 5/2012 | Dorsch et al. | |
| 2004/0152739 A1 | 8/2004 | Hanau | |
| 2004/0259863 A1 | 12/2004 | Eggenweiler et al. | |
| 2005/0107391 A1 | 5/2005 | Cui et al. | |
| 2007/0015771 A1 | 1/2007 | Matteucci et al. | |
| 2007/0043057 A1 | 2/2007 | Matteucci et al. | |
| 2007/0203136 A1 | 8/2007 | Lu et al. | |
| 2007/0265272 A1 | 11/2007 | Cheng et al. | |
| 2008/0293719 A1 | 11/2008 | Dorsch et al. | |
| 2009/0098181 A1 | 4/2009 | Lu et al. | |
| 2009/0124612 A1 | 5/2009 | Albrecht et al. | |
| 2010/0197690 A1 | 8/2010 | Schadt et al. | |
| 2010/0234354 A1 | 9/2010 | Dorsch et al. | |
| 2010/0273796 A1 | 10/2010 | Dorsch et al. | |
| 2010/0280030 A1 | 11/2010 | Schadt et al. | |
| 2010/0286390 A1 | 11/2010 | Shigeta et al. | |
| 2011/0034474 A1 | 2/2011 | Dorsch et al. | |
| 2011/0092498 A1 | 4/2011 | Dorsch et al. | |
| 2011/0098269 A1 | 4/2011 | Becknell et al. | |
| 2011/0112061 A1 | 5/2011 | Hu et al. | |
| 2011/0263596 A1 | 10/2011 | Schadt et al. | |
| 2011/0269957 A1 | 11/2011 | Fandrick et al. | |
| 2012/0028988 A1 | 2/2012 | Sakamoto et al. | |
| 2012/0040949 A1 | 2/2012 | Berthel et al. | |

FOREIGN PATENT DOCUMENTS

| | | |
|---|---|---|
| DE | 196 04 388 | 8/1997 |
| DE | 10 2005 057 924 | 6/2007 |
| EP | 1 061 077 | 12/2000 |
| JP | 10 259176 | 9/1998 |
| JP | 2001 192384 | 7/2001 |
| WO | WO-03 037349 | 5/2003 |
| WO | WO-2004 58762 | 7/2004 |
| WO | WO 2005/004607 | 1/2005 |
| WO | WO 2006/015263 A2 | 2/2006 |
| WO | WO-2007 044796 | 4/2007 |
| WO | WO-2007 064797 | 6/2007 |
| WO | WO-2007 065518 | 6/2007 |
| WO | WO-2007 075567 | 7/2007 |
| WO | WO 2007/075567 A1 | 7/2007 |
| WO | WO-2007 130383 | 11/2007 |
| WO | WO 2007/132308 A1 | 11/2007 |
| WO | WO-2008 008539 | 1/2008 |
| WO | WO-2008 075068 | 6/2008 |
| WO | WO-2009 006959 | 1/2009 |
| WO | WO-2009 007074 | 1/2009 |
| WO | WO-2009 050197 | 4/2009 |
| WO | WO-2009 053737 | 4/2009 |
| WO | WO-2009 063061 | 5/2009 |
| WO | WO-2009 080314 | 7/2009 |
| WO | WO-2009 080364 | 7/2009 |
| WO | WO-2009 080533 | 7/2009 |
| WO | WO-2009 080534 | 7/2009 |

(Continued)

OTHER PUBLICATIONS

International Search Report of PCT/EP2009/005172, Date of Completion Jan. 20, 2010, Date of Mailing Jan. 26, 2010.

(Continued)

*Primary Examiner* — Rebecca Anderson
(74) *Attorney, Agent, or Firm* — Millen, White, Zelano & Branigan, P.C.

(57) ABSTRACT

Compounds of the formula (I), in which $X^1$, $X^2$, $X^3$, $X^4$, $X^5$, $R^1$, $R^2$, $R^3$, $R^{3'}$, $R^4$, $R^6$ and $R^7$ have the meanings indicated in Claim 1, are inhibitors of tyrosine kinases, in particular Met kinase, and can be employed, inter alia, for the treatment of tumours.

26 Claims, No Drawings

FOREIGN PATENT DOCUMENTS

| WO | WO-2009 080555 | 7/2009 |
|---|---|---|
| WO | WO-2009 080721 | 7/2009 |
| WO | WO-2009 080725 | 7/2009 |
| WO | WO-2009 081197 | 7/2009 |
| WO | WO-2009 083076 | 7/2009 |
| WO | WO-2009 083105 | 7/2009 |
| WO | WO-2009 085659 | 7/2009 |
| WO | WO-2009 086041 | 7/2009 |
| WO | WO-2009 086264 | 7/2009 |

OTHER PUBLICATIONS

"Cancer" MedLine Plus (2009). Accessed Mar. 17, 2009. http://www.nlm.nih.gov/medlineplus/cancer.html.

Berthou, S. et al., "The Met kinase inhibitor SU11274 exhibits a selective inhibition pattern toward different receptor mutated variants," Oncogene, 2004, vol. 23, pp. 5387-5393.

Buchanan, Sean G. "SGX523 is an exquisitely selectively, ATP-competitive inhibitor of the MET receptor tyrosine kinase with antitumor activity in vivo" Molecular Cancer Therapeutics, Dec. 2009;8(12): 3181-3190.

Cancer Drug Design and Discovery, Neidle, Stephen, ed. (Elsevier/Academic Press), pp. 427-431, 2008.

Chen et al., Circulation, 2008, vol. 118, pp. 84-95.

Database Beilstein, Beilstein Institute for Organic Chemistry, Frankfurt, DE, XP002506064M 1991.

Database CA (Online) Chemical Abstracts Service, Columbus, Ohio US:2002, Dushamov, D.A.et al., Acylation of 6-halobenzoxazolin-2-ones by acid chlorides in the presence of a small quantity of iron(III) chloride hexahydrate, XP002496356.

Database CA (Online) Chemical Abstracts Service, Columbus, Ohio US:1979, Domagalina, Eugenia et al, "Acylation of benzoxazolin -2-ones and 3-hydroxyl-1, 2 benzisoxazoles," XP002496357 Polish Journal of Pharmacology and Pharmacy.

Database CA (Online) Chemical Abstracts Service, Columbus, Ohio US; 1967, Nitta, yoshihiro et al: "Benzoxazolone derivatives," XP002496358.

Databse Beilstein, Beilstein Institute for Organic Chemistry, Frankfurt, DE, XP002506065, Need Date, 2008.

Ettmayer et al. "Lessons Learned from Marketed and Investigational Prodrugs" J. Med. Chem., (2004), 47(10):2393-2404.

Flouzat, Christine et al. "Synthesis and N-substitution of an uncommon heterocyclic system: oxazolo[5,4-b] yridine-2(1H)-one," Tetrahedron Letters, Bd. 33, Nr. 32, 1992 Seiten 4571-4574, XP00249354.

Fujisawa Pharmaceut Co Ltd., "Pyrazolopyridine compound and pharmaceutical use thereof," Patent Abstracts of Japan, Publication Date: Jul. 17, 2001.

Glen, H. et al., "E7080, a multi-targeted tyrosin kinase inhibitor suppresses tumor cell migration and invasion," BMC Cancer, 2011, vol. 11, No. 309.

Golub et al. "Molecular Classification of Cancer: Class Discovery and Class Prediction by Gene Expression Monitoring" Science (1999), 286:521-537.

Guessous, Fadila et al. "An orally Bioavailable c-Met Kinase Inhibitor Potently Inhibits Brain Tumor Malignancy and Growth", Anti-Cancer in Medicinal Chemistry, 2010, 10(1):28-35.

H. Refaat et al., "Synthesis and Anti-Inflammatory Activity of Certain Piperazinylthienylpyridazine Derivatives," Arch Pharm Res., vol. 30, No. 7 (2007) pp. 803-811.

Hackh's Chem Dict., 3rd. Ed 1944, p. 18.

Hawley's Condensed Chem Dict., 14th Ed., 2002.

Hill, K. S. et al., "Met Receptor Tyrosine Kinase Signaling Induces Secretion of the Angiogenic Chemokine Interleukin-8/CXCL8 in Pancreatic Cancer," PloS One, Jul. 1, 2012, vol. 7, No. 7, e40420.

http://www.iupac.org/goldbook/A00123.pdf, downloaded Oct. 29, 2010.

http://www.uspto.gov/wb/offices/pac/dapp/1pecba.htm#7 last accessed on Nov. 22, 2011.

International Search Report "International Application No. PCT/EP2008/003696," Date of Completion Sep. 18, 2008, Date of Mailing Oct. 1, 2008, 4 pages.

International Search Report for PCT/EP2008/003473 dated Jul. 28, 2008.

International Search Report for PCT/EP2008/005928 dated Dec. 11, 2008.

International Search Report of PCT/EP2008/009970 dated Jan. 28, 2009.

International Search Report of PCT/EP2009/002137 (Jun. 4, 2009).

International Search Report of PCT/EP2009/003675 (Aug. 26, 2009).

Japan Tobacco Inc., "New Amide derivative having vascularization inhibiting action and its use," Patent Abstracts of Japan, Publication Date: Sep. 29, 1998; English Abstracts of JP-10 259176.

Jin et al., Mol. Cancer Ther., Jul. 2006, vol. 5, pp. 1754-1763.

Jin, Hongkui et al. "MetMAb, the One-Armed 5D5 Anti-c-Met Antibody, Inhibits Orthotopic Pancreatic Tumor Growth and Improves Survival", Cancer Res 2008;68(11):4360-4368; Jun. 1, 2008. www.aacrjournals.org.

Johnson et al. "Relationships between drug activity in NCI preclinical in vitro and in vivo models and early clinical trials." British Journal of Cancer (2001) 84(10):1424-1431.

Knowles, Lynn M. et al. "HGF and c-Met Participate in Paracrine Tumorigenic Pathways in Head and Neck Squamous Cell Cancer", Clin Cancer Res, Jun. 1, 2009; 15(11):3740-3750. www.aacrjournals.org.

Lala et al. "Role of nitric oxide in tumor progression: Lessons from experimental tumors." Cancer and Metastasis Review (1998), 17(1), 91-106.

Lima, L. M. et al., "Bioisosterism: a useful strategy for molecular modification and drug design," Current Medicinal Chemistry, 2005, vol. 12, No. 1, pp. 23-49.

Liu, Xiangdong et al. "A novel kinase inhibitor INCB28060 blocks c-MET-dependent signaling, neoplastic activities, and crosstalk with EGFR and HER-3", Clin Cancer Res (45 pages); Published: Sep. 14, 2011.

Locatelli et al., J. Biol. Chem., Jun. 17, 2011, vol. 286, No. 24, pp. 21062-21072.

M. Goekce et al., "Synthesis of New Mannich Bases of Arylpyridazinones as Analgesic and Anti-Inflammatory Agents," Drug Research, vol. 55, No. 6 (2005) pp. 318-325.

Merck Patent GMBH, "New Aryl-alkyl diazinone derivatives," Espacenet, Publication Date: Aug. 14, 1997; English Abstract of DE-196 04 388.

Morissette et al. "High-throughput crystallization: polymorphs, salts, co-crystals and solvates of pharmaceutical solids." Advanced Drug Deliver Reviews 2004, 56 275-300.

Office Action for Related Columbian Patent Application No. 09-138245 dated Sep. 21, 2012.

Qian, Fawn et al. "Inhibition of Tumor Cell Growth, Invasion, and Metastasis by EXEL-2880 (XL880, GSK1363089), a Novel Inhibitor of HGF and VEGF Receptor Tyrosine Kinases", Cancer Res 2009;69(20):8009-8016. Dated: Oct. 15, 2009. www.aacrjournals.org.

Samlowski et al., BJU Int., 2008, vol. 102, No. 2, pp. 162-165, Abstract.

Sampson, Erik R. et al. "The Orally Bioavailable Met Inhibitor PF-2341066 Inhibits Osteosarcoma Growth and Osteolysis/Matrix Production in a Xenograft Model", Journal of Bone and Mineral Research, 26(6):1283-1294; Dated: Jun. 2011.

Sausville et al. "Contributions of Human Tumor Xenografts to Anti-cancer Drug Development" Cancer Res. 2006, 66(7), Apr. 1, 2006.

Search Report for Chilean Patent Application No. 3854-08 filed Dec. 19, 2008.

Singapore Written Opinion for Application No. 201007486-2 (Sep. 26, 2011).

Smolen et al., Proc. Natl Acad Sci USA, Feb. 2006, vol. 103, No. 7, pp. 2316-2321.

Souillac et al. Characterization of Delivery Systems, Differential Scanning Calorimetry, pp. 217-218 (in Encyclopedia of Controlled Drug Delivery, 1999, John Wiley & Sons, pp. 212-227).

Stella, V. "Prodrugs as therapeutics" Expert Opin. Ther. Patents (2004), 14(3):277-280.

Testa, B. "Prodrug research: futile or fertile?" Biochemical Pharmacology, 68 (2004): 2097-2106.

Tuynman et al., Br. J. Cancer, 2008, vol. 98, No. 6, pp. 1102-1108, Abstract.

Ucar, Huseyin et al., "Fries Like Rearragement: a novel and efficient metod for the sythesis of 6-acyl-2(3H)-benzoxazolones and 6-acyl-2(3H)-benzothiazolones" Tetrahedron, Bd. 54, Nr. 9, 1998, Seiten 1763-1772 XP002496355.

Underiner et al., Anti-Cancer Agents in Medicinal Chemistry, 2010, vol. 10, pp. 7-27.

Vippagunta, S.R. "Crystalline Solids" Advanced Drug Delivery Reviews 48(2001):3-26.

Wang et al., Clin Cancer Res., Mar. 15, 2012, vol. 18, No. 6, pp. 1663-1671.

Ziegler, D. S. et al., "Resistance of human glioblastoma multiforme cells to growth factor inhibitors is overcome by blockade of inhibitors of apoptosis proteins," Journal of Clinical Investigation, Sep. 9, 2008, vol. 118, pp. 3109-3122.

Zillhardt, Marion et al. "Foretinib (GSK1363089), an Orally Available Multikinase Inhibitor of c-Met and VEGFR-2, Blocks Proliferation, Induces Anoikis, and Impairs Ovarian Cancer Metastasis", Clin Cancer Res 2011;17:4042-4051. Published: May 6, 2011. www.aacrjournals.org.

Zou, Helen Y. et al. "An Orally Available Small-Molecule Inhibitor of c-Met, PF-2341066, Exhibits Cytoreductive Antitumor Efficacy through Antiproliferative and Antiangiogenic Mechanisms", Cancer Res 2007; 67:(9)4408-4417. Dated: May 1, 2007. www.aacrjournals.org.

Zou, Helen Y. et al. "Sensitivity of Selected Human tumor Models to PF-04217903, a Novel Selective c-Met Kinase Inhibitor", Molecular Cancer Therapeutics, American Association for Cancer Research. 32 pages. Published: Mar. 2, 2012.

BICYCLIC TRAIZOLE DERIVATIVES FOR TREATING OF TUMORS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases and/or serine/threonine kinases, plays a role, furthermore to pharmaceutical compositions which comprise these compounds, and to the use of the compounds for the treatment of kinase-induced diseases.

In particular, the present invention relates to compounds and to the use of compounds in which the inhibition, regulation and/or modulation of signal transduction by Met kinase plays a role.

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The role of the receptor tyrosine kinase Met in human oncogenesis and the possibility of inhibition of HGF (hepatocyte growth factor) dependent Met activation are described by S. Berthou et al. in Oncogene, Vol. 23, No. 31, pages 5387-5393 (2004). The inhibitor SU11274 described therein, a pyrrole-indoline compound, is potentially suitable for combating cancer. Another Met kinase inhibitor for cancer therapy is described by J. G. Christensen et al. in Cancer Res. 2003, 63(21), 7345-55.

A further tyrosine kinase inhibitor for combating cancer is reported by H. Hov et al. in Clinical Cancer Research Vol. 10, 6686-6694 (2004). The compound PHA-665752, an indole derivative, is directed against the HGF receptor c-Met. It is furthermore reported therein that HGF and Met make a considerable contribution to the malignant process of various forms of cancer, such as, for example, multiple myeloma.

The synthesis of small compounds which specifically inhibit, regulate and/or modulate signal transduction by tyrosine kinases and/or serine/threonine kinases, in particular Met kinase, is therefore desirable and an aim of the present invention.

It has been found that the compounds according to the invention and salts thereof have very valuable pharmacological properties while being well tolerated.

The present invention specifically relates to compounds of the formula I which inhibit, regulate and/or modulate signal transduction by Met kinase, to compositions which comprise these compounds, and to processes for the use thereof for the treatment of Met kinase-induced diseases and complaints, such as angiogenesis, cancer, tumour formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases and diseases of the immune system, also autoimmune diseases, cirrhosis, diabetes and diseases of the blood vessels, also instability and permeability and the like in mammals.

Solid tumours, in particular fast-growing tumours, can be treated with Met kinase inhibitors. These solid tumours include monocytic leukaemia, brain, urogenital, lymphatic system, stomach, laryngeal and lung carcinoma, including lung adenocarcinoma and small-cell lung carcinoma.

The present invention is directed to processes for the regulation, modulation or inhibition of Met kinase for the prevention and/or treatment of diseases in connection with unregulated or disturbed Met kinase activity. In particular, the compounds of the formula I can also be employed in the treatment of certain forms of cancer. The compounds of the formula I can furthermore be used to provide additive or synergistic effects in certain existing cancer chemotherapies, and/or can be used to restore the efficacy of certain existing cancer chemotherapies and radiotherapies.

The compounds of the formula I can furthermore be used for the isolation and investigation of the activity or expression of Met kinase. In addition, they are particularly suitable for use in diagnostic methods for diseases in connection with unregulated or disturbed Met kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-anti-bodies (phospho-ABs). The phospho-AB binds only the phosphorylated substrate. This binding can be detected by chemiluminescence using a second peroxidase-conjugated anti-sheep antibody (Ross et al., 2002, Biochem. J.).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

Other triazolopyrazines are described as cMet kinase inhibitors in WO 2005/004607, WO 2007/132308 and US 2007/0265272. Triazolopyridazine derivatives are described as Met kinase inhibitors in WO 2007/064797, WO 2007/075567, WO 2007/138472, WO 2008/008539, WO 2008/051805.

SUMMARY OF THE INVENTION

The invention relates to compounds of the formula I

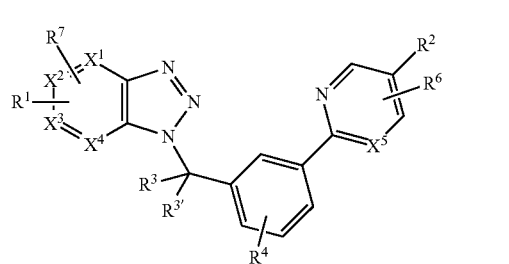

in which
$X^1, X^2, X^3,$
$X^4, X^5$ each, independently of one another, denote CH or N,
$R^1, R^2, R^7$ each, independently of one another, denote H, Hal, A, $[C(R^5)_2]_n OR^5$, $N=CR^5N(R^5)_2$, $SR^5$, $NO_2$, CN, $[C(R^5)_2]_n COOR^5$, $CON(R^5)_2$, $NR^5COA$, $NR^5SO_2A$, $SO_2N(R^5)_2$, $S(O)_m A$, $[C(R^5)_2]_n N(R^5)_2$, $[C(R^5)_2]_n$Het, $O[C(R^5)_2]_p OR^5$, $O[C(R^5)_2]_p N(R^5)_2$, $O[C(R^5)_2]_p N^+O^-(R^5)_2$, $O[C(R^5)_2]_n$Het, $S[C(R^5)_2]_p N(R^5)_2$, $S[C(R^5)_2]_p$Het, $NR^5[C(R^5)_2]_n N(R^5)_2$, $NR^5[C(R^5)_2]_n$Het, $NHCON(R^5)_2$, $NHCONH[C(R^5)_2]_n N(R^5)_2$, $NHCONH[C(R^5)_2]_n$Het, $NHCO[C(R^5)_2]_p N(R^5)_2$, $NHCO[C(R^5)_2]_n$-Het, $[C(R^5)_2]_n CON(R^5)_2$, $CONR^5[C(R^5)_2]_n N(R^5)_2$, $CONR^5[C(R^5)_2]_n NR^5COOA$, $[C(R^5)_2]_n NR^5COOA$, $CONR^5[C(R^5)_2]_n OR^5$, $CONR^5[C(R^5)_2]_n$Het, COHet, COA, $CH=CH-COOR^5$, $CH=CH-N(R^5)_2$, $CH=CH-CON(R^5)_2$, $O-[C(R^5)_2]_n$-cycloalkylene-$[C(R^5)_2]_n$-Het, $O-[C(R^5)_2]_n$-cycloalkylene-$[C(R^5)_2]_n$-$N(R^5)_2$, $O-[C(R^5)_2]_n$-cycloalkylene-$[C(R^5)_2]_n$-$OR^5$, $[C(R^5)_2]_n$Ar, $O[C(R^5)_2]_n$Ar, $S[C(R^5)_2]_n$Ar, $NR^5[C(R^5)_2]_n$Ar, $NHCONH[C(R^5)_2]_n$Ar, $NHCO[C(R^5)_2]_n$Ar or $CONR^5[C(R^5)_2]_n$Ar or COAr,
$R^3, R^{3'}$ each, independently of one another, denote H, F or $R^8$,
$R^3$ and $R^{3'}$ together also denote an alkylene chain having 2-5 C atoms, in which 1 or 2 non-adjacent $CH_2$ groups may be replaced by O, NH and/or $NR^5$,
$R^4, R^6$ each, independently of one another, denote H, A or Hal,
$R^5$ denotes H or $R^8$,
$R^8$ denotes unbranched or branched alkyl having 1-6 C atoms,
A denotes unbranched or branched alkyl having 1-10 C atoms, in which 1-7H atoms may be replaced by OH, F, Cl and/or Br,
and/or in which one or two $CH_2$ groups may be replaced by O, $NR^8$, NH, S, SO, $SO_2$ and/or CH=CH groups, or
cyclic alkyl having 3-7 C atoms, which may be monosubstituted by OH,
Ar denotes phenyl, naphthyl or biphenyl, each of which is unsubstituted or mono-, di- or trisubstituted by Hal, A, $OR^5$, $N(R^5)_2$, $SR^5$, $NO_2$, CN, $COOR^5$, $CON(R^5)_2$, $NR^5COA$, $NR^5SO_2A$, $SO_2N(R^5)_2$ and/or $S(O)_m A$,
Het denotes a mono-, bi- or tricyclic saturated, unsaturated or aromatic heterocycle having 1 to 4 N, O and/or S atoms, which may be unsubstituted or mono-, di- or trisubstituted by Hal, A, $OR^5$, $N(R^5)_2$, $SR^5$, $NO_2$, CN, $COOR^5$, $CON(R^5)$ $_2$, NR$^5$COA, NR$^5$SO$_2$A, SO$_2$N(R$^5$)$_2$, S(O)$_m$A, CO-Het$^1$, Het$^1$, [C(R$^5$)$_2$]$_n$N(R$^5$)$_2$, [C(R$^5$)$_2$]$_n$OR$^5$, [C(R$^5$)$_2$]$_n$Het$^1$, O[C(R$^5$)$_2$]$_p$N(R$^5$)$_2$, O[C(R$^5$)$_2$]$_p$OR$^5$, O[C(R$^5$)$_2$]$_n$Het$^1$, NHCOOA, NHCON(R$^5$)$_2$, NHCOO[C(R$^5$)$_2$]$_p$N(R$^5$)$_2$, NHCOO[C(R$^5$)$_2$]$_n$Het$^1$, NHCONH[C(R$^5$)$_2$]$_n$N(R$^5$)$_2$, NHCONH[C(R$^5$)$_2$]$_n$Het$^1$, OCONH[C(R$^5$)$_2$]$_n$N(R$^5$)$_2$, OCONH[C(R$^5$)$_2$]$_n$Het$^1$, CO-Het$^1$, CHO, COA, =S, =NH, =NA and/or =O (carbonyl oxygen), Het$^1$ denotes a monocyclic saturated heterocycle having 1 to 2 N and/or O atoms, which may be mono- or disubstituted by A, COOA, OA, OH, Hal and/or =O (carbonyl oxygen), Hal denotes F, Cl, Br or I, m denotes 0, 1 or 2, n denotes 0, 1, 2, 3 or 4, p denotes 1, 2, 3 or 4, and pharmaceutically usable salts, tautomers and stereoisomers thereof, including mixtures thereof in all ratios, Compounds of the formula I are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to Claims 1-14 and pharmaceutically usable salts, tautomers and stereoisomers thereof, characterised in that a) a compound of the formula II

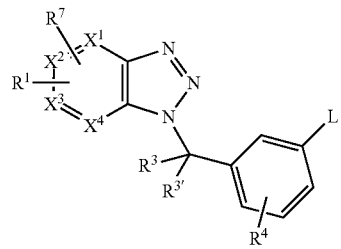

in which X$^1$, X$^2$, X$^3$, X$^4$, R$^1$, R$^3$, R$^{3'}$, R$^4$ and R$^7$ have the meanings
indicated in Claim 1 and
L denotes a boronic acid or boronic acid ester radical,
is reacted with a compound of the formula III

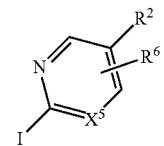

in which X$^5$, R$^2$ and R$^6$ have the meanings indicated in Claim 1, or b) a radical R$^1$, R$^2$ and/or R$^7$ is replaced by another radical R$^1$, R$^2$ and/or R$^7$ by replacing a halogen atom by a radical Het and/or Ar, which have the meanings indicated in Claim 1, or c) a compound of the formula IV

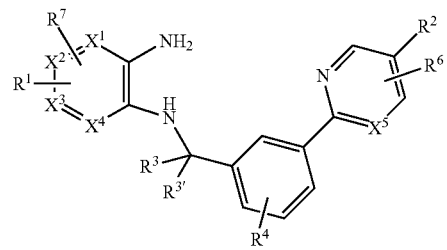

in which X$^1$, X$^2$, X$^3$, X$^4$, X$^5$, R$^1$, R$^2$, R$^3$, R$^{3'}$, R$^4$, R$^6$ and R$^7$
have the meanings indicated in Claim 1,
is reacted with NaNO$_2$,
and/or
a base or acid of the formula I is converted into one of its salts.

Above and below, the radicals X$^1$, X$^2$, X$^3$, X$^4$, X$^5$, R$^1$, R$^2$, R$^3$, R$^{3'}$, R$^4$, R$^6$ and R$^7$ have the meanings indicated for the formula I, unless expressly stated otherwise.

For all radicals which occur more than once, such as, for example, R$^5$, their meanings are independent of one another.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A particularly preferably denotes unbranched or branched alkyl having 1-10 C atoms, in which 1-7H atoms may be replaced by OH, F, Cl and/or Br,
or
cyclic alkyl having 3-7 C atoms, which may be monosubstituted by OH.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl (cycloalkyl) preferably denotes cyclopropyl, cyclobutyl, cylopentyl, cyclohexyl or cycloheptyl.

Cycloalkylene preferably denotes cyclopropylene, cyclobutylene, cylopentylene, cyclohexylene or cycloheptylene.

$X^1$, $X^4$ preferably denote CH or N.
$X^2$, $X^3$ preferably denote CH.
$X^5$ preferably denotes N, furthermore CH.

$R^1$ preferably denotes H, Hal, A, $S(O)_m A$, Ar, Het, $O[C(R^5)_2]_n Ar$, $O[C(R^5)_2]_n Het$ or $OR^5$.

$R^1$ particularly preferably denotes H, Hal, A, $OR^5$, $S(O)_m A$ or thiazolyl, thiophenyl, furanyl, pyrrolyl, oxazolyl, isoxazolyl, oxadiazolyl, pyrazolyl, imidazolyl, thiadiazolyl, pyridazinyl, pyrazinyl, pyridinyl, pyrimidinyl, pyrazolyloxy, where the heterocycles may also be mono-, di- or trisubstituted by Hal, A and/or $O[C(R^5)_2]_p OR^5$,
or
phenyl or phenoxy, each of which is mono-, di- or trisubstituted by Hal and/or CN.

$R^2$ preferably denotes A, Hal, $[C(R^5)_2]_n N(R^5)_2$, $[C(R^5)_2]_n Het$, $O[C(R^5)_2]_p N(R^5)_2$, $O[C(R^5)_2]_n Het$, $[C(R^5)_2]_n OR^5$, $O[C(R^5)_2]_p OR^5$, $O-[C(R^5)_2]_n$-cycloalkylene-$[C(R^5)_2]_n-N(R^5)_2$, $[C(R^5)_2]_n NR^5 COOA$ or $CH=CH-COOR^5$.

$R^3$, $R^{3'}$ preferably, in each case independently of one another, denote H or $R^8$, particularly preferably H, methyl, ethyl or propyl, very particularly preferably H or methyl.

$R^4$, $R^6$ preferably denote H.
$R^7$ preferably denotes H or Hal.
$R^5$ preferably denotes H, methyl, ethyl or propyl, very particularly preferably H or methyl.
$R^8$ preferably denotes alkyl having 1, 2, 3, 4, 5 or 6 C atoms, preferably methyl, ethyl, propyl, isopropyl, butyl, isobutyl, sec-butyl, tert-butyl, pentyl or hexyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)-phenyl, o-, m- or p-(N-ethylamino)phenyl, o-, m- or p-(N,N-diethylamino)-phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-aminosulfonylphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar particularly preferably denotes phenyl which is unsubstituted or mono-, di- or trisubstituted by Hal, A and/or CN.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het particularly preferably denotes a monocyclic saturated, unsaturated or aromatic heterocycle having 1 to 4 N, O and/or S atoms, which may be un-substituted or mono-, di- or trisubstituted by Hal, A, $COOR^5$, $O[C(R^5)_2]_p OR^5$, $[C(R^5)_2]_n Het^1$, $O[C(R^5)_2]_n Het^1$ and/or $=O$.

Het very particularly preferably denotes piperidinyl, pyrrolidinyl, morpholinyl, piperazinyl, oxazolidinyl, pyrazolyl, pyridinyl, pyrimidinyl, furyl, thienyl, oxazolyl, oxadiazolyl, imidazolyl, pyrrolyl, isoxazolyl or imidazolidinyl, where the radicals may also be mono- or disubstituted by Hal, A, $COOR^5$, $O[C(R^5)_2]_pOR^5$, $[C(R^5)_2]_nHet^1$, $O[C(R^5)_2]_nHet^1$ and/or =O.

$Het^1$ preferably denotes piperidinyl, pyrrolidinyl, morpholinyl, piperazinyl, oxazolidinyl or imidazolidinyl, where the radicals may also be mono- or disubstituted by COOA, =O and/or A.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Il, which conform to the formula I and in which the radicals not designated in greater detail have the meaning indicated for the formula I, but in which in Ia $R^1$ denotes H, Hal, A, $S(O)_mA$, Ar, Het, $O[C(R^5)_2]_nAr$, $O[C(R^6)_2]_nHet$ or $OR^5$;

in Ib $R^7$ denotes H or Hal;

in Ic $R^2$ denotes A, Hal, $[C(R^5)_2]_nN(R^5)_2$, $[C(R^5)_2]_nHet$, $O[C(R^5)_2]_pN(R^5)_2$, $O[C(R^5)_2]_nHet$, $[C(R^5)_2]_nOR^5$, $O[C(R^5)_2]_pOR^5$, $O-[C(R^5)_2]_n$-cycloalkylene-$[C(R^5)_2]_n$-$N(R^5)_2$, $[C(R^5)_2]_nNR^5COOA$ or $CH=CH-COOR^5$;

in Id $R^3$, $R^{3'}$ each, independently of one another, denote H or $R^8$;

in Ie $R^4$, $R^6$ denote H;

in If $R^1$ denotes H, Hal, A, $S(O)_mA$ or
  thiazolyl, thiophenyl, furanyl, pyrrolyl, oxazolyl, isoxazolyl, oxadiazolyl, pyrazolyl, imidazolyl, thiadiazolyl, pyridazinyl, pyrazinyl, pyridinyl, pyrimidinyl or pyrazolyloxy, where the heterocycles may also be mono-, di- or trisubstituted by Hal, A and/or $O[C(R^5)_2]_pOR^5$,
  or
  phenyl or phenoxy, each of which is mono-, di- or trisubstituted by Hal and/or CN;

in Ig Het denotes a monocyclic saturated, unsaturated or aromatic heterocycle having 1 to 4 N, O and/or S atoms, which may be unsubstituted or mono-, di- or trisubstituted by Hal, A, $COOR^5$, $O[C(R^5)_2]_pOR^5$, $[C(R^5)_2]_nHet^1$, $O[C(R^5)_2]_nHet^1$ and/or =O;

in Ih Het denotes piperidinyl, pyrrolidinyl, morpholinyl, piperazinyl, oxazolidinyl, pyrazolyl, pyridinyl, pyrimidinyl, furyl, thienyl, oxazolyl, oxadiazolyl, imidazolyl, pyrrolyl, isoxazolyl or imidazolidinyl, where the radicals may also be mono- or disubstituted by Hal, A, $COOR^5$, $O[C(R^5)_2]_pOR^5$, $[C(R^5)_2]_nHet^1$, $O[C(R^5)_2]_nHet^1$ and/or =O;

in Ii $Het^1$ denotes piperidinyl, pyrrolidinyl, morpholinyl, piperazinyl, oxazolidinyl or imidazolidinyl, where the radicals may also be mono- or disubstituted by COOA, =O and/or A;

in Ij Ar denotes phenyl which is unsubstituted or mono-, di- or trisubstituted by Hal, A and/or CN;

in Ik A denotes unbranched or branched alkyl having 1-10 C atoms,
  in which 1-7H atoms may be replaced by OH, F, Cl and/or Br,
  or
  cyclic alkyl having 3-7 C atoms, which may be monosubstituted by OH;

in Il $X^1$, $X^2$, $X^3$, $X^4$, $X^5$ each, independently of one another, denote CH or N, $R^1$ denotes H, Hal, A, $S(O)_mA$, Ar, Het, $O[C(R^5)_2]_nAr$, $O[C(R^5)_2]_nHet$ or $OR^5$, $R^7$ denotes H or Hal, $R^2$ denotes A, Hal, $[C(R^5)_2]_nN(R^5)_2$, $[C(R^5)_2]_nHet$, $O[C(R^5)_2]_pN(R^5)_2$, $O[C(R^5)_2]_nHet$, $[C(R^5)_2]_nOR^5$, $O[C(R^5)_2]_pOR^5$, $O-[C(R^5)_2]_n$-cycloalkylene-$[C(R^5)_2]_n$-$N(R^5)_2$, $[C(R^5)_2]_nNR^5COOA$ or $CH=CH-COOR^5$, $R^3$, $R^{3'}$ each, independently of one another, denote H or $R^8$, $R^4$, $R^6$ denote H, $R^5$ denotes H or $R^8$, $R^8$ denotes unbranched or branched alkyl having 1-6 C atoms, A denotes unbranched or branched alkyl having 1-10 C atoms,
  in which 1-7H atoms may be replaced by OH, F, Cl and/or Br,
  or
  cyclic alkyl having 3-7 C atoms, which may be monosubstituted by OH, Ar denotes phenyl which is unsubstituted or mono-, di- or trisubstituted by Hal, A and/or CN, Het denotes a monocyclic saturated, unsaturated or aromatic heterocycle having 1 to 4 N, O and/or S atoms, which may be unsubstituted or mono-, di- or trisubstituted by Hal, A, $COOR^5$, $O[C(R^5)_2]_pOR^5$, $[C(R^5)_2]_nHet^1$, $O[C(R^5)_2]_nHet^1$ and/or =O, $Het^1$ denotes piperidinyl, pyrrolidinyl, morpholinyl, piperazinyl, oxazolidinyl or imidazolidinyl, where the radicals may also be mono- or disubstituted by COOA, =O and/or A, Hal denotes F, Cl, Br or I, m denotes 0, 1 or 2, n denotes 0, 1, 2, 3 or 4, p denotes 1, 2, 3 or 4;

and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by reacting a compound of the formula II with a compound of the formula III.

The reaction is carried out under conditions as are known to the person skilled in the art for a Suzuki reaction.

The starting compounds of the formulae II and III are generally known. If they are novel, however, they can be prepared by methods known per se.

In the compounds of the formula II, L preferably denotes

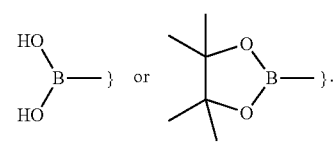

The reaction is carried out under standard conditions of a Suzuki coupling. Depending on the conditions used, the reaction time is between a few minutes and 14 days, the reaction temperature is between about −30° and 140°, normally between 0° and 100°, in particular between about 60° and about 90°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanol, toluene, dimethoxyethane.

Compounds of the formula I can furthermore preferably be obtained by replacing a radical $R^1$ and/or $R^7$ by another radical $R^1$ and/or $R^7$. Preferably, a halogen atom is replaced by a radical Het and/or Ar, which have the meanings indicated in claim 1. The reaction is preferably carried out under the conditions of a Suzuki coupling.

Compounds of the formula I can furthermore preferably be obtained by reacting a compound of the formula IV preferably with $NaNO_2$.

The reaction is carried out under standard conditions

Depending on the conditions used, the reaction time is between a few minutes and 14 days, the reaction temperature is between about −30° and 140°, normally between 0° and 100°, in particular between about 60° and about 90°. Suitable inert solvents are those mentioned above.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula I, but contain an NHR' group (in which R' is an amino-protecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxyl-protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the formula I and/or pharmaceutically usable salts and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of partdoses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable salts and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to Claim 1 according to the invention and/or physiologically acceptable salts thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable salts and stereoisomers thereof, including mixtures thereof in all ratios, for the preparation of a medicament for the treatment of diseases in which the inhibition, regulation and/or modulation of kinase signal transduction plays a role.

Preference is given here to Met kinase.

Preference is given to the use of compounds of the formula I, and pharmaceutically usable salts and stereoisomers thereof, including mixtures thereof in all ratios, for the preparation of a medicament for the treatment of diseases which are influenced by inhibition of tyrosine kinases by the compounds according to Claim 1.

Particular preference is given to the use for the preparation of a medicament for the treatment of diseases which are influenced by inhibition of Met kinase by the compounds according to Claim 1.

Especial preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (Cl 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multidrug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokinetransfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin |
| | Tetraplatin | (Johnson Matthey) |
| | Ormiplatin | BBR-3464 |
| | Iproplatin | (Hoffrnann-La Roche) |
| | | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC |
| | Idatrexate | (Hoffmann-La Roche) |
| | | Ethynylcytidine (Taiho) |
| Topo-isomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan |
| | 7-ethyl-10-hydroxycamptothecin | (Beaufour-Ipsen) |
| | | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 |
| | | (Chong Kun Dang) |
| | BBR-3576 (Novuspharrna) | KW-2170 (Kyowa Hakko) |
| Anti-tumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate |
| | Epirubicin | (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem |
| | Mitoxantron (Novantron) | Pharmaceuticals) |
| Anti-mitotic agents | Paclitaxel | SB 408075 |
| | Docetaxel | (GlaxoSmithKline) |
| | Colchicine | E7010 (Abbott) |
| | Vinblastine | PG-TXL |
| | Vincristine | (Cell Therapeutics) |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | Cemadotin (BASF) | ER-86526 (Eisai) |
| | RPR 109881A (Aventis) | Combretastatin A4 (BMS) |

TABLE 1-continued

| Category | | | |
|---|---|---|---|
| | TXD 258 (Aventis) | Isohomohalichondrin-B | |
| | Epothilone B (Novartis) | (PharmaMar) | |
| | T 900607 (Tularik) | ZD 6126 (AstraZeneca) | |
| | T 138067 (Tularik) | PEG-Paclitaxel (Enzon) | |
| | Cryptophycin 52 (Eli Lilly) | AZ10992 (Asahi) | |
| | Vinflunine (Fabre) | IDN-5109 (Indena) | |
| | Auristatin PE (Teikoku Hormone) | AVLB (Prescient NeuroPharma) | |
| | BMS 247550 (BMS) | Azaepothilon B (BMS) | |
| | BMS 184476 (BMS) | BNP-7787 (BioNumerik) | |
| | BMS 188797 (BMS) | CA-4-prodrug (OXiGENE) | |
| | Taxoprexin (Protarga) | Dolastatin-10 (NrH) | |
| | | CA-4 (OXiGENE) | |
| Aromatase inhibitors | Aminoglutethimide | Exemestan | |
| | Letrozole | Atamestan (BioMedicines) | |
| | Anastrazole | YM-511 (Yamanouchi) | |
| | Formestan | | |
| Thymidylate synthase inhibitors | Pemetrexed (Eli Lilly) | Nolatrexed (Eximias) | |
| | ZD-9331 (BTG) | CoFactor™ (BioKeys) | |
| DNA antagonists | Trabectedin (PharmaMar) | Mafosfamide (Baxter International) | |
| | Glufosfamide (Baxter International) | Apaziquone (Spectrum Pharmaceuticals) | |
| | Albumin + 32P (Isotope Solutions) | O6-benzylguanine (Paligent) | |
| | Thymectacin (NewBiotics) | | |
| | Edotreotid (Novartis) | | |
| Farnesyl transferase inhibitors | Arglabin (NuOncology Labs) | Tipifarnib (Johnson & Johnson) | |
| | Ionafarnib (Schering-Plough) | Perillyl alcohol (DOR BioPharma) | |
| | BAY-43-9006 (Bayer) | | |
| Pump inhibitors | CBT-1 (CBA Pharma) | Zosuquidar trihydrochloride (Eli Lilly) | |
| | Tariquidar (Xenova) | Biricodar dicitrate (Vertex) | |
| | MS-209 (Schering AG) | Pivaloyloxymethyl butyrate (Titan) | |
| Histone acetyl transferase inhibitors | Tacedinaline (Pfizer) | Depsipeptide (Fujisawa) | |
| | SAHA (Aton Pharma) | | |
| | MS-275 (Schering AG) | | |
| Metalloproteinase inhibitors | Neovastat (Aeterna Laboratories) | CMT-3 (CollaGenex) | |
| | Marimastat (British Biotech) | BMS-275291 (Celltech) | |
| | | Tezacitabine (Aventis) | |
| Ribonucleoside reductase inhibitors | Gallium maltolate (Titan) | Didox (Molecules for Health) | |
| | Triapin (Vion) | | |
| TNF-alpha agonists/antagonists | Virulizin (Lorus Therapeutics) | Revimid (Celgene) | |
| | CDC-394 (Celgene) | | |
| Endothelin-A receptor antagonists | Atrasentan (Abbot) | YM-598 (Yamanouchi) | |
| | ZD-4054 (AstraZeneca) | | |
| Retinoic acid receptor agonists | Fenretinide (Johnson & Johnson) | Alitretinoin (Ligand) | |
| | LGD-1550 (Ligand) | | |
| Immunomodulators | Interferon | Dexosome therapy (Anosys) | |
| | Oncophage (Antigenics) | Pentrix (Australian Cancer Technology) | |
| | GMK (Progenics) | JSF-154 (Tragen) | |
| | Adenocarcinoma vaccine (Biomira) | Cancer vaccine (Intercell) | |
| | CTP-37 (AVI BioPharma) | Norelin (Biostar) | |
| | JRX-2 (Immuno-Rx) | BLP-25 (Biomira) | |
| | PEP-005 (Peplin Biotech) | MGV (Progenics) | |
| | Synchrovax vaccines (CTL Immuno) | I3-Alethin (Dovetail) | |
| | Melanoma vaccine (CTL Immuno) | CLL-Thera (Vasogen) | |
| | p21-RAS vaccine (GemVax) | | |
| Hormonal and antihormonal agents | Oestrogens | Prednisone | |
| | Conjugated oestrogens | Methylprednisolone | |
| | Ethynyloestradiol | Prednisolone | |
| | chlortrianisene | Aminoglutethimide | |
| | Idenestrol | Leuprolide | |
| | Hydroxyprogesterone caproate | Goserelin | |
| | | Leuporelin | |
| | Medroxyprogesterone | Bicalutamide | |
| | Testosterone | Flutamide | |
| | Testosterone propionate | Octreotide | |
| | Fluoxymesterone | Nilutamide | |
| | Methyltestosterone | Mitotan | |
| | Diethylstilbestrol | P-04 (Novogen) | |
| | Megestrol | 2-Methoxyoestradiol (EntreMed) | |
| | Tamoxifen | | |
| | Toremofin | Arzoxifen (Eli Lilly) | |
| | Dexamethasone | | |
| Photodynamic agents | Talaporfin (Light Sciences) | Pd-Bacteriopheophorbid (Yeda) | |
| | Theralux (Theratechnologies) | Lutetium-Texaphyrin (Pharmacyclics) | |
| | Motexafin-Gadolinium (Pharmacyclics) | Hypericin | |
| Tyrosine kinase inhibitors | Imatinib (Novartis) | Kahalide F (PharmaMar) | |
| | Leflunomide (Sugen/Pharmacia) | CEP-701 (Cephalon) | |
| | | CEP-751 (Cephalon) | |
| | ZDI839 (AstraZeneca) | MLN518 (Millenium) | |
| | Erlotinib (Oncogene Science) | PKC412 (Novartis) | |
| | Canertjnib (Pfizer) | Phenoxodiol O | |
| | Squalamine (Genaera) | Trastuzumab (Genentech) | |
| | SU5416 (Pharmacia) | C225 (ImClone) | |
| | SU6668 (Pharmacia) | rhu-Mab (Genentech) | |
| | ZD4190 (AstraZeneca) | MDX-H210 (Medarex) | |
| | ZD6474 (AstraZeneca) | 2C4 (Genentech) | |
| | Vatalanib (Novartis) | MDX-447 (Medarex) | |
| | PKI166 (Novartis) | ABX-EGF (Abgenix) | |
| | GW2016 (GlaxoSmithKline) | IMC-1C11 (ImClone) | |
| | EKB-509 (Wyeth) | | |
| | EKB-569 (Wyeth) | | |
| Various agents | SR-27897 (CCK-A inhibitor, Sanofi-Synthelabo) | BCX-1777 (PNP inhibitor, BioCryst) |  |
| | Tocladesine (cyclic AMP agonist, Ribapharm) | Ranpirnase (ribonuclease stimulant, Alfacell) | |
| | Alvocidib (CDK inhibitor, Aventis) | Galarubicin (RNA synthesis inhibitor, Dong-A) | |
| | CV-247 (COX-2 inhibitor, Ivy Medical) | Tirapazamine (reducing agent, SRI International) | |
| | P54 (COX-2 inhibitor, Phytopharm) | N-Acetylcysteine (reducing agent, Zambon) | |
| | CapCell™ (CYP450 stimulant, Bavarian Nordic) | R-Flurbiprofen (NF-kappaB inhibitor, Encore) | |
| | GCS-IOO (gal3 antagonist, GlycoGenesys) | 3CPA (NF-kappaB inhibitor, Active Biotech) | |
| | G17DT immunogen (gastrin inhibitor, Aphton) | Seocalcitol (vitamin D receptor agonist, Leo) | |
| | Efaproxiral (oxygenator, Allos Therapeutics) | 131-I-TM-601 (DNA antagonist, TransMolecular) | |
| | PI-88 (heparanase inhibitor, Progen) | Eflornithin (ODC inhibitor, ILEX Oncology) | |
| | Tesmilifen (histamine antagonist, YM BioSciences) | Minodronic acid (osteoclast inhibitor, Yamanouchi) | |
| | Histamine (histamine H2 receptor agonist, Maxim) | Indisulam (p53 stimulant, Eisai) | |
| | Tiazofurin (IMPDH inhibitor, Ribapharm) | Aplidin (PPT inhibitor, PharmaMar) | |
| | Cilengitide (integrin antagonist, Merck KGaA) | Rituximab (CD20 antibody, Genentech) | |
| | SR-31747 (IL-1 antagonist, Sanofi-Synthelabo) | Gemtuzumab (CD33 antibody, Wyeth Ayerst) | |
| | CCI-779 (mTOR kinase inhibitor, Wyeth) | PG2 (haematopoiesis promoter, Pharmagenesis) | |
| | Exisulind (PDE-V inhibitor, Cell Pathways) | Immunol™ (triclosan mouthwash, Endo) | |
| | CP-461 (PDE-V inhibitor, Cell Pathways) | Triacetyluridine (uridine prodrug, Wellstat) | |
| | AG-2037 (GART inhibitor, Pfizer) | SN-4071 (sarcoma agent, Signature BioScience) | |
| | WX-UK1 (plasminogen activator inhibitor, Wilex) | TransMID-107™ (immunotoxin, KS Biomedix) | |
| | PBI-1402 (PMN stimulant, ProMetic LifeSciences) | PCK-3145 (apoptosis promoter, Procyon) | |
| | Bortezomib (proteasome inhibitor, Millennium) | Doranidazole (apoptosis promoter, Pola) | |
| | SRL-172 (T-cell stimulant, SR Pharma) | CHS-828 (cytotoxic agent, Leo) | |
| | TLK-286 (glutathione-S transferase inhibitor, Telik) | Trans-retinic acid (differentiator, NIH) | |
| | PT-100 (growth factor agonist, Point Therapeutics) | MX6 (apoptosis promoter, MAXIA) | |
| | Midostaurin (PKC inhibitor, Novartis) | Apomine (apoptosis |

TABLE 1-continued

| Category | | |
|---|---|---|
| | Bryostatin-1 (PKC stimulant, GPC Biotech) | promoter ILEX Oncology) |
| | CDA-II (apoptosis promoter, Everlife) | Urocidin (apoptosis promoter, Bioniche) |
| | SDX-101 (apoptosis promoter Salmedix) | Ro-31-7453 (apoptosis promoter, La Roche) |
| | Ceflatonin (apoptosis promoter, ChemGenex) | Brostallicin (apoptosis promoter, Pharmacia) |
| Alkylating agents | Cyclophosphamide | Lomustin |
| | Busulfan | Procarbazin |
| | Ifosfamide | Altretamin |
| | Melphalan | Estramustine phosphate |
| | Hexamethylmelamine | Mechlorethamin |
| | Thiotepa | Streptozocin |
| | chloroambucil | Temozolomid |
| | Dacarbazine | Semustin |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin |
| | Tetraplatin | (Johnson Matthey) |
| | Ormiplatin | BBR-3464 (Hoffmann-La Roche) |
| | Iproplatin | SM-11355 (Sumitomo) |
| | | AP-5280 (Access) |
| Antimeta-bolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topo-isomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | |
| | Topotecan | TAS-103 (Taiho) |
| | Dexrazoxanet (TopoTarget) | Elsamitrucin (Spectrum) |
| | Pixantrone (Novuspharrna) | J-107088 (Merck & Co) |
| | Rebeccamycin analogue (Exelixis) | BNP-1350 (BioNumerik) |
| | | CKD-602 (Chong Kun Dang) |
| | BBR-3576 (Novuspharrna) | KW-2170 (Kyowa Hakko) |
| Anti-tumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Anti-mitotic agents | Paclitaxel | SB 408075 (GlaxoSmithKline) |
| | Docetaxel | |
| | Colchicine | E7010 (Abbott) |
| | Vinblastine | PG-TXL |
| | Vincristine | (Cell Therapeutics) |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | Cemadotin (BASF) | ER-86526 (Eisai) |
| | RPR 109881A (Aventis) | Combretastatin A4 (BMS) |
| | TXD 258 (Aventis) | Isohomohalichondrin-B |
| | Epothilone B (Novartis) | (PharmaMar) |
| | T 900607 (Tularik) | ZD 6126 (AstraZeneca) |
| | T 138067 (Tularik) | PEG-Paclitaxel (Enzon) |
| | Cryptophycin 52 (Eli Lilly) | AZ10992 (Asahi) |
| | Vinflunine (Fabre) | !DN-5109 (Indena) |
| | Auristatin PE (Teikoku Hormone) | AVLB (Prescient NeuroPharma) |
| | BMS 247550 (BMS) | Azaepothilon B (BMS) |
| | BMS 184476 (BMS) | BNP-7787 (BioNumerik) |
| | BMS 188797 (BMS) | CA-4-prodrug (OXiGENE) |
| | Taxoprexin (Protarga) | Dolastatin-10 (NrH) |
| | | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thy-midylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metallo-proteinase inhibitors | Neovastat (Aeterna Laboratories) | CMT-3 (CollaGenex) |
| | Marimastat (British Biotech) | BMS-275291 (Celltech) |
| Ribo-nucleoside reductase inhibitors | Gallium maltolate (Titan) | Tezacitabine (Aventis) |
| | Triapin (Vion) | Didox (Molecules for Health) |
| TNF-alpha agonists/antagonists | Virulizin (Lorus Therapeutics) | Revimid (Celgene) |
| | CDC-394 (Celgene) | |
| Endo-thelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | Melanoma vaccine (CTL Immuno) | !3-Alethin (Dovetail) |
| | p21-RAS vaccine (GemVax) | CLL-Thera (Vasogen) |
| Hormonal and anti-hormonal agents | Oestrogens | Prednisone |
| | Conjugated oestrogens | Methylprednisolone |
| | Ethynyloestradiol | Prednisolone |
| | chlorotrianisene | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |

TABLE 1-continued

| | | | |
|---|---|---|---|
| | Fluoxymesterone | Nilutamide | |
| | Methyltestosterone | Mitotan | |
| | Diethylstilbestrol | P-04 (Novogen) | |
| | Megestrol | 2-Methoxyoestradiol | |
| | Tamoxifen | (EntreMed) | |
| | Toremofin | Arzoxifen (Eli Lilly) | |
| | Dexamethasone | | |
| Photo-dynamic agents | Talaporfin (Light Sciences) | Pd-Bacteriopheophorbid (Yeda) | |
| | Theralux (Theratechnologies) | Lutetium-Texaphyrin (Pharmacyclics) | |
| | Motexafin-Gadolinium (Pharmacyclics) | Hypericin | |
| Tyrosine kinase inhibitors | Imatinib (Novartis) | Kahalide F (PharmaMar) | |
| | Leflunomide (Sugen/Pharmacia) | CEP-701 (Cephalon) | |
| | | CEP-751 (Cephalon) | |
| | ZDI839 (AstraZeneca) | MLN518 (Millenium) | |
| | Erlotinib (Oncogene Science) | PKC412 (Novartis) | |
| | Canertjnib (Pfizer) | Phenoxodiol O | |
| | Squalamine (Genaera) | Trastuzumab (Genentech) | |
| | SU5416 (Pharmacia) | C225 (ImClone) | |
| | SU6668 (Pharmacia) | rhu-Mab (Genentech) | |
| | ZD4190 (AstraZeneca) | MDX-H210 (Medarex) | |
| | ZD6474 (AstraZeneca) | 2C4 (Genentech) | |
| | Vatalanib (Novartis) | MDX-447 (Medarex) | |
| | PKI166 (Novartis) | ABX-EGF (Abgenix) | |
| | GW2016 (GlaxoSmithKline) | IMC-1C11 (ImClone) | |
| | EKB-509 (Wyeth) | | |
| | EKB-569 (Wyeth) | | |
| Various agents | SR-27897 (CCK-A inhibitor, Sanofi-Synthelabo) | BCX-1777 (PNP inhibitor, BioCryst) | |
| | Tocladesine (cyclic AMP agonist, Ribapharm) | Ranpirnase (ribonuclease stimulant, Alfacell) | |
| | Alvocidib (CDK inhibitor, Aventis) | Galarubicin (RNA synthesis inhibitor, Dong-A) | |
| | CV-247 (COX-2 inhibitor, Ivy Medical) | Tirapazamine (reducing agent, SRI International) | |
| | P54 (COX-2 inhibitor, Phytopharm) | N-Acetylcysteine (reducing agent, Zambon) | |
| | CapCell ™ (CYP450 stimulant, Bavarian Nordic) | R-Flurbiprofen (NF-kappaB inhibitor, Encore) | |
| | GCS-IOO (gal3 antagonist, GlycoGenesys) | 3CPA (NF-kappaB inhibitor, Active Biotech) | |
| | G17DT immunogen (gastrin inhibitor, Aphton) | Seocalcitol (vitamin D receptor agonist, Leo) | |
| | Efaproxiral (oxygenator, Allos Therapeutics) | 131-I-TM-601 (DNA antagonist, TransMolecular) | |
| | PI-88 (heparanase inhibitor, Progen) | Eflornithin (ODC inhibitor, ILEX Oncology) | |
| | Tesmilifen (histamine antagonist, YM BioSciences) | Minodronic acid (osteoclast inhibitor, Yamanouchi) | |
| | Histamine (histamine H2 receptor agonist, Maxim) | Indisulam (p53 stimulant, Eisai) | |
| | Tiazofurin (IMPDH inhibitor, Ribapharm) | Aplidin (PPT inhibitor, PharmaMar) | |
| | Cilengitide (integrin antagonist, Merck KGaA) | Rituximab (CD20 antibody, Genentech) | |
| | SR-31747 (IL-1 antagonist, Sanofi-Synthelabo) | Gemtuzumab (CD33 antibody, Wyeth Ayerst) | |
| | CCI-779 (mTOR kinase inhibitor, Wyeth) | PG2 (haematopoiesis promoter, Pharmagenesis) | |
| | Exisulind (PDE-V inhibitor, Cell Pathways) | Immunol ™ (triclosan mouthwash, Endo) | |
| | CP-461 (PDE-V inhibitor, Cell Pathways) | Triacetyluridine (uridine prodrug, Wellstat) | |
| | AG-2037 (GART inhibitor, Pfizer) | SN-4071 (sarcoma agent, Signature BioScience) | |
| | WX-UK1 (plasminogen activator inhibitor, Wilex) | TransMID-107 ™ (immunotoxin, KS Biomedix) | |
| | PBI-1402 (PMN stimulant, ProMetic LifeSciences) | PCK-3145 (apoptosis promoter, Procyon) | |
| | Bortezomib (proteasome inhibitor, Millennium) | Doranidazole (apoptosis promoter, Pola) | |
| | SRL-172 (T-cell stimulant, SR Pharma) | CHS-828 (cytotoxic agent, Leo) | |
| | TLK-286 (glutathione-S transferase inhibitor, Telik) | Trans-retinic acid (differentiator, NIH) | |
| | PT-100 (growth factor agonist, Point Therapeutics) | MX6 (apoptosis promoter, MAXIA) | |
| | Midostaurin (PKC inhibitor, Novartis) | Apomine (apoptosis promoter, ILEX Oncology) | |
| | Bryostatin-1 (PKC stimulant, GPC Biotech) | Urocidin (apoptosis promoter, Bioniche) | |
| | CDA-II (apoptosis promoter, Everlife) | Ro-31-7453 (apoptosis promoter, La Roche) | |
| | SDX-101 (apoptosis promoter, Salmedix) | Brostallicin (apoptosis promoter, Pharmacia) | |
| | Ceflatonin (apoptosis promoter, ChemGenex) | | |

A combined treatment of this type can be achieved with the aid of simultaneous, consecutive or separate dispensing of the individual components of the treatment. Combination products of this type employ the compounds according to the invention.

Assays

The compounds of the formula I described in the examples were tested by the assays described below and were found to have kinase inhibitory activity. Other assays are known from the literature and could readily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

Measurement of Met Kinase Activity

According to the manufacturer's data (Met, active, Upstate, catalogue No. 14-526), Met kinase is expressed for the purposes of protein production in insect cells (Sf21; S. frugiperda) and subsequent affinity-chromatographic purification as "N-terminal 6His-tagged" recombinant human protein in a baculovirus expression vector.

The kinase activity can be measured using various available measurement systems. In the scintillation proximity method (Sorg et al., J. of Biomolecular Screening, 2002, 7, 11-19), the flashplate method or the filter binding test, the radioactive phosphorylation of a protein or peptide as substrate is measured using radioactively labelled ATP ($^{32}$P-ATP, $^{33}$P-ATP). In the case of the presence of an inhibitory compound, a reduced radioactive signal, or none at all, can be detected. Furthermore, homogeneous time-resolved fluorescence resonance energy transfer (HTR-FRET) and fluoroescence polarisation (FP) technologies can be used as assay methods (Sills et al., J. of Biomolecular Screening, 2002, 191-214).

Other non-radioactive ELISA assay methods use specific phospho anti-bodies (phospho-ABs). The phospho antibody only binds the phosphorylated substrate. This binding can be detected by chemiluminescence using a second peroxidase-conjugated antibody (Ross et al., 2002, Biochem. J.).

Flashplate Method (Met Kinase)

The test plates used are 96-well Flashplate® microtitre plates from Perkin Elmer (Cat. No. SMP200). The components of the kinase reaction described below are pipetted into the assay plate. The Met kinase and the substrate poly Ala-Glu-Lys-Tyr, (pAGLT, 6:2:5:1), are incubated for 3 hrs at room temperature with radioactively labelled $^{33}$P-ATP in the presence and absence of test substances in a total volume of 100 µl. The reaction is terminated using 150 µl of a 60 mM EDTA solution. After incubation for a further 30 min at room temperature, the supernatants are filtered off with suction, and the wells are washed three times with 200 µl of 0.9% NaCl solution each time. The measurement of the bound radioactivity is carried out by means of a scintillation measuring instrument (Topcount NXT, Perkin-Elmer).

The full value used is the inhibitor-free kinase reaction. This should be approximately in the range 6000-9000 cpm. The pharmacological zero value used is staurosporin in a final concentration of 0.1 mM. The inhibitory values (IC50) are determined using the RS1_MTS program.

Kinase reaction conditions per well:
30 μl of assay buffer
10 μl of substance to be tested in assay buffer with 10% of DMSO
10 μl of ATP (final concentration 1 μM cold, 0.35 μCi of $^{33}$P-ATP)
50 μl of Met kinase/substrate mixture in assay buffer; (10 ng of enzyme/well, 50 ng of pAGLT/well)
Solutions used:
Assay buffer:
50 mM HEPES
   3 mM magnesium chloride
   3 μM sodium orthovanadate
   3 mM manganese(II) chloride
   1 mM dithiothreitol (DTT)
pH=7.5 (to be set using sodium hydroxide)
Stop solution:
60 mM Titriplex III (EDTA)
$^{33}$P-ATP: Perkin-Elmer;
Met kinase: Upstate, Cat. No. 14-526, Stock 1 μg/10 μl; spec. activity 954 U/mg;
Poly-Ala-Glu-Lys-Tyr, 6:2:5:1: Sigma Cat. No. P1152
In-Vivo Tests Experimental procedure: Female Balb/C mice (breeder: Charles River Wiga) were 5 weeks old on arrival. They were acclimatised to our keeping conditions for 7 days. Each mouse was subsequently injected subcutaneously in the pelvic area with 4 million TPR-Met/NIH3T3 cells in 100 μl of PBS (without Ca++ and Mg++). After 5 days, the animals were randomised into 3 groups, so that each group of 9 mice had an average tumour volume of 110 μl (range: 55-165). 100 μl of vehicle (0.25% methylcellulose/100 mM acetate buffer, pH 5.5) were administered daily to the control group, and 200 mg/kg of "A56" or "A91" dissolved in the vehicle (volume likewise 100 μl/animal) were administered daily to the treatment groups, in each case by gastric tube. After 9 days, the controls had an average volume of 1530 μl and the experiment was terminated.

Measurement of the tumour volume: The length (L) and breadth (B) were measured using a Vernier calliper, and the tumour volume was calculated from the formula L×B×B/2.

Keeping conditions: 4 or 5 animals per cage, feeding with commercial mouse food (Sniff).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M$^+$
FAB (fast atom bombardment) (M+H)$^+$
ESI (electrospray ionisation) (M+H)$^+$
APCI-MS (atmospheric pressure chemical ionisation-mass spectrometry) (M+H)$^+$.
HPLC Methods:
Method A:
Flow rate: 2 ml/min 99:01-0:100 water+0.1% (vol.) of TFA:acetonitrile+0.1% (vol.) of TFA
0.0 to 0.2 min: 99:01
0.2 to 3.8 min: 99:01->0:100
3.8 to 4.2 min: 0:100
Column: Chromolith Performance RP18e; 100 mm long, internal diameter 3 mm, wavelength: 220 nm
Retention time Rt. in minutes [min].
Method B:
Gradient: 4.2 min/flow rate: 2 ml/min
99% (A): 1% (B)–0:100 water+0.01% (vol.) of AS (A): acetonitrile+0.01% (vol.) of AS (B)
0.0 to 0.2 min: 99:01
0.2 to 3.8 min 99:01-0:100
3.8 to 4.2 min 0:100
Method C:
Gradient: 4.2 min/flow rate: 2 ml/min
99% (A): 1% (B)–0:100
water+0.05% (vol.) of AS (A): acetonitrile+0.04% (vol.) of AS (B)
0.0 to 0.2 min: 99:01
0.2 to 3.8 min 99:01-0:100
3.8 to 4.2 min 0:100

EXAMPLES

Preparation of Benzyl Alcohols

Preparation of {3-[5-(3-dimethylaminopropoxy)pyrimidin-2-yl]phenyl}methanol

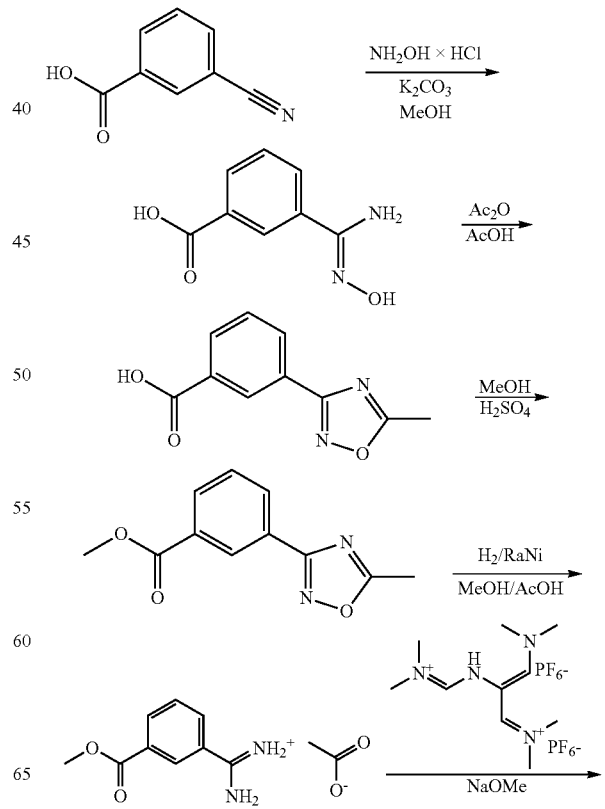

-continued

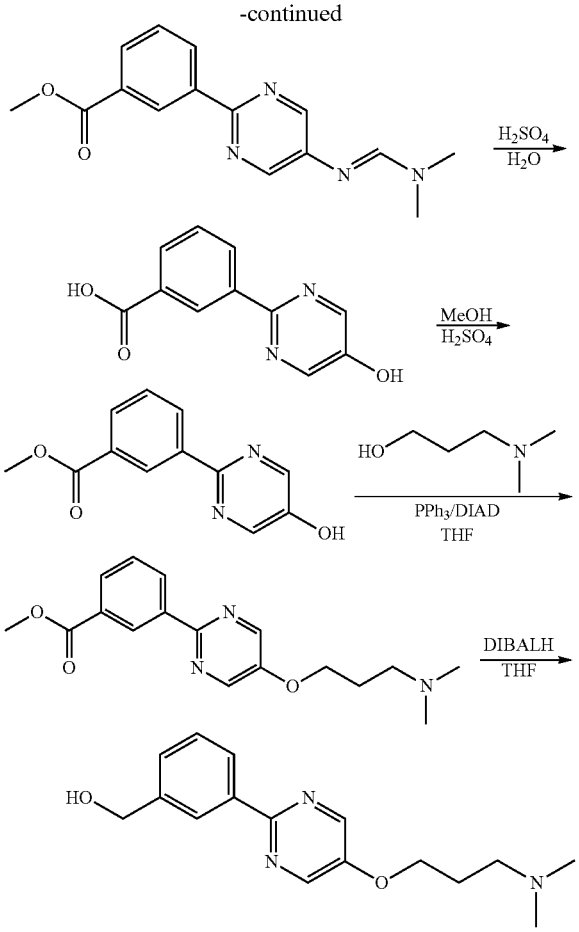

Step 1:

1382 g (10.0 mol) of potassium carbonate are added in portions with stirring to a suspension, kept at 30° C., of 500 g (3.40 mol) of 3-cyanobenzoic acid in 8 l of methanol. 695 g (10.0 mol) of hydroxylammonium chloride are subsequently added in small portions at an internal temperature of 40-45° C. The reaction mixture is then heated at the boil for 15 hours. The reaction mixture is evaporated in vacuo, the residue is dissolved in water and acidified using 37% aqueous hydrochloric acid. The resultant precipitate is filtered off with suction, washed with water and dried in vacuo: 3-(N-hydroxycarbamimidoyl)benzoic acid as colourless crystals; LCMS 181.

Step 2:

A mixture of 614 g (3.41 mol) of 3-(N-hydroxycarbamimidoyl)benzoic acid, 756 ml (8.0 mol) of acetic anhydride and 2 l of acetic acid is heated at a temperature of 118° C. for 14 hours. The reaction mixture is cooled to 6° C. and filtered off with suction. The residue is taken up in 2 l of water, filtered off with suction and washed well with water. The residue is recrystallised from ethanol/water: 3-(5-methyl-1,2,4-oxadiazol-3-yl)benzoic acid as colourless crystals;

m.p. 225° C.; LCMS 205.

Step 3:

7.83 ml (147 mmol) of concentrated sulfuric acid are added to a suspension of 30.0 g (147 mmol) of 3-(5-methyl-1,2,4-oxadiazol-3-yl)benzoic acid in 150 ml of methanol, and the mixture is heated at the boil for 18 hours. The reaction mixture is cooled in an ice bath, water is added, the product is filtered off with suction and washed well with water:methyl 3-(5-methyl-1,2,4-oxadiazol-3-yl)-benzoate as colourless crystals; LCMS 219.

Step 4:

150 ml of acetic acid, 150 ml of water and 50 g of water-moist Raney nickel are added to a solution of 327 g (1.47 mol) of methyl 3-(5-methyl-1,2,4-oxadiazol-3-yl)benzoate in 3 l of methanol, and the mixture is hydrogenated for 18 hours at room temperature and atmospheric pressure. The catalyst is filtered off, and the filtrate is evaporated. The residue is taken up in tert-butyl methyl ether, heated to the boil and filtered off with suction. The residue is dried in vacuo: 3-methoxycarbonylbenzamidinium acetate as colourless crystals; LCMS 179.

Step 5:

2.2 l of a freshly prepared 1.5 M sodium methoxide solution are added dropwise with stirring to a suspension of 259 g (1.09 mol) of 3-methoxycarbonylbenzamidinium acetate and 528 g (1.08 mol) of ({2-dimethylamino-1-[dimethylimmoniomethyl]vinylamino}methylene)dimethylammonium dihexafluorophosphate (prepared by the method of C. B. Dousson et al., Synthesis 2005, 1817) in 1 l of methanol. The reaction mixture is then warmed to 60° C. over the course of 40 min and kept at this temperature for 30 min. The reaction mixture is then cooled to room temperature, diluted with 10 l of dichloromethane and washed three times with 5 l of water each time. The organic phase is dried over sodium sulfate and evaporated. The residue is recrystallised from ethyl acetate: methyl 3-[5-(dimethylaminomethyleneamino)-pyrimidin-2-yl]benzoate as beige crystals; m.p. 140° C.; LCMS 285.

Step 6:

160 ml (2.88 mol) of concentrated sulfuric acid are added to a suspension of 103.5 g (364 mmol) of methyl 3-[5-(dimethylaminomethyleneamino)pyrimidin-2-yl]benzoate in 1.3 l of water, and the mixture is heated at the boil for 4 hours. The reaction mixture is cooled to room temperature, diluted with water and filtered off with suction. The residue is washed with water and dried in vacuo: 3-(5-hydroxypyrimidin-2-yl)benzoic acid as brownish crystals; LCMS 217.

Step 7:

32.7 ml (445 mmol) of thionyl chloride are added to a suspension of 88.0 g (366 mmol) of 3-(5-hydroxypyrimidin-2-yl)benzoic acid in 1.4 l of methanol, and the mixture is heated at 80° C. for 2 hours. 20 ml (276 mmol) of thionyl chloride and, after 2 hours, again 10 ml (138 mmol) of thionyl chloride are then added. After each addition, the reaction mixture is stirred at 80° C. for 2 hours. The reaction mixture is evaporated in vacuo to a volume of about 300 ml. The resultant precipitate is filtered off and dried in vacuo: methyl 3-(5-hydroxypyrimidin-2-yl)benzoate as brownish crystals; LCMS 231.

Step 8:

A solution, kept under nitrogen, of 6.1 g (26.5 mmol) of methyl 3-(5-hydroxypyrimidin-2-yl)benzoate, 10.5 g (39.8 mmol) of triphenylphosphine and 4.76 ml (39.8 mmol) of 3-(dimethylamino)-1-propanol in 200 ml of THF is cooled in an ice bath, and 8.21 ml (39.8 mmol) of diisopropyl azodicarboxylate are slowly added dropwise with stirring. After stirring at room temperature for 2 hours, the reaction mixture is evaporated in vacuo. The residue is partitioned between dichloromethane and saturated aqueous potassium hydrogensulfate solution. The aqueous phase is separated off, adjusted to a pH of 12 using saturated aqueous sodium hydroxide solution and extracted twice with dichloromethane. The organic phase is dried over sodium sulfate and evaporated. The residue is chromatographed on a silica-gel column with dichloromethane/methanol as eluent: methyl 3-[5-(3-dimethylaminopropoxy)pyrimidin-2-yl]benzoate as colourless crystals; LCMS 316.

Step 9:

200 ml of a 1 M solution of diisobutylaluminium hydride in THF are added dropwise with stirring to a solution, kept under nitrogen, of 12.6 g (40.0 mmol) of methyl 3-[5-(3-dimethylaminopropoxy)pyrimidin-2-yl]benzoate in 200 ml of THF. After stirring at room temperature for 1 hour, 10 ml of a saturated aqueous sodium sulfate solution are added dropwise. The resultant precipitate is filtered off with suction and washed with dichloromethane. The filtrate is dried over sodium sulfate and evaporated. The residue is taken up in a mixture of diethyl ether and petroleum ether. The resultant precipitate is filtered off with suction, washed with petroleum ether and dried in vacuo: {3-[5-(3-dimethylaminopropoxy)pyrimidin-2-yl]phenyl}methanol as white crystals; m.p. 103-104° C.; LCMS 288; Rt.=1.76 min (method A).

The following can be prepared analogously:

| Compound No. | Name and/or structure | LCMS [M + H] | Rt. in min |
|---|---|---|---|
| | (structure) | 316 | 1.73 (method A) |
| | (structure) | 300 | |
| | (structure) | 386 | |
| | (structure) | 314 | |
| | (structure) | 400 | |

Alternative synthetic route for the preparation of methyl 3-(5-hydroxypyrimidin-2-yl)benzoate Step 1:

A solution of 10.6 g (100 mmol) of sodium carbonate in 50 ml of water is added to a solution of 14.5 g (50.5 mmol) of 5-bromo-2-iodopyrimidine in 50 ml of toluene, and the mixture is warmed to 80° C. under nitrogen. 351 mg (0.50 mmol) of bis(triphenylphosphine)palladium(II) chloride and a solution of 9.18 g (50.0 mmol) of (3-methoxycarbonylphenyl) boronic acid in 75 ml of ethanol are then added, and the resultant suspension is stirred at 80° C. for 24 hours. The reaction mixture is evaporated in vacuo, and the residue is partitioned between water and ethyl acetate. The organic phase is dried over sodium sulfate and evaporated. The residue is taken up in 100 ml of methanol, and 5.30 g (50 mmol) of sodium carbonate are added. The resultant suspension is heated under reflux for 32 hours. After cooling to room temperature, the residue is filtered off with suction. The residue is washed with methanol and water and dried in vacuo: methyl 3-(5-bromopyrimidin-2-yl)-benzoate as sand-coloured crystals; LCMS 293/295;

$^1$H-NMR (d$_6$-DMSO): δ [ppm]=3.91 (s, 3H), 7.71 (t, J=7.8 Hz, 1H), 8.14 (dt, J=7.5 Hz, J=1.5 Hz, 1H), 8.61 (dt, J=7.9 Hz, J=1.4 Hz, 1H), 8.96 (t, J=1.7 Hz, 1H), 9.13 (s, 2H).

Step 2:

7.47 g (76.2 mmol) of potassium acetate are added to a solution of 7.44 g (25.4 mmol) of methyl 3-(5-bromopyrimidin-2-yl)benzoate and 7.26 g (27.9 mmol) of bis(pinacolato) diboron in 50 ml of DMF, and the mixture is heated to 80° C. under nitrogen. 535 mg (0.76 mmol) of bis(triphenylphosphine)palladium(II) chloride are then added, and the mixture is stirred at 80° C. for 18 hours. The reaction mixture is partitioned between water and dichloromethane. The organic phase is dried over sodium sulfate and evaporated. The residue is heated with tert-butyl methyl ether, allowed to cool and filtered off with suction and washed with tert-butyl methyl ether and dried in vacuo: methyl 3-[5-(4,4,5,5-tetramethyl-1,3,2-dioxaborolan-2-yl)-pyrimidin-2-yl]benzoate as beige crystals;

$^1$H-NMR (d$_6$-DMSO): δ [ppm]=1.35 (s, 12H), 3.92 (s, 3H), 7.72 (t, J=7.8 Hz, 1H), 8.15 (dt, J=7.5 Hz, J=1.5 Hz, 1H), 8.69 (dt, J=7.9 Hz, 1.4 Hz, 1H), 9.04 (t, J=1.7 Hz, 1H), 9.07 (s, 2H).

Step 3:

A suspension of 1.24 g (8.09 mmol) of sodium perborate tetrahydrate in 13 ml of water is added to a solution of 1.93 g (5.39 mmol) of methyl 3-[5-(4,4,5,5-tetramethyl-1,3,2-dioxaborolan-2-yl)pyrimidin-2-yl]benzoate in 13 ml of THF, and the resultant two-phase mixture is stirred at room temperature for 18 hours. The reaction mixture is filtered, and the filtrate is evaporated in vacuo to about half of the original volume. The mixture is re-filtered, and the filtrate is acidified using 10 ml of 1 N hydrochloric acid. The resultant precipitate is filtered off with suction, washed with water and dried in vacuo: methyl 3-(5-hydroxypyrimidin-2-yl)benzoate as pale-yellow crystals; LCMS 231; 1H-NMR (d$_6$-DMSO): δ [ppm]

=3.91 (s, 3H), 7.64 (t, J=7.8 Hz, 1H), 8.02 (dt, J=7.5 Hz, 1.5 Hz, 1H), 8.49 (s, 2H) 8.52 (dt, J=7.9 Hz, 1.4 Hz, 1H), 8.89 (t, J=1.7 Hz, 1H), 10.7 (bs, 1H).

Preparation of [3-(5-methylpyridin-2-yl)phenyl]methanol

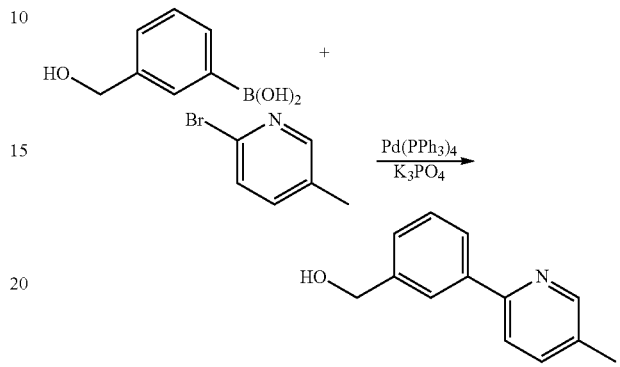

92 mg (0.08 mmol) of tetrakis(triphenylphosphine)palladium are added to a suspension, kept under nitrogen, of 849 mg (4.0 mmol) of tripotassium phosphate, 344 mg (2.0 mmol) of 2-bromo-5-methylpyridine and 304 mg (2.0 mmol) of 3-hydroxymethylbenzeneboronic acid in 12 ml of dioxane and 1 ml of water, and the mixture is heated at the boil with stirring for 18 hours. The reaction mixture is cooled to room temperature and partitioned between water and ethyl acetate. The organic phase is dried over sodium sulfate, evaporated, and the residue is chromatographed on a silica-gel column with dichloromethane/methanol as eluent: [3-(5-methylpyridin-2-yl)phenyl]methanol as yellowish oil; LCMS 200.

Preparation of [3-(5-methylpyrimidin-2-yl)phenyl]methanol

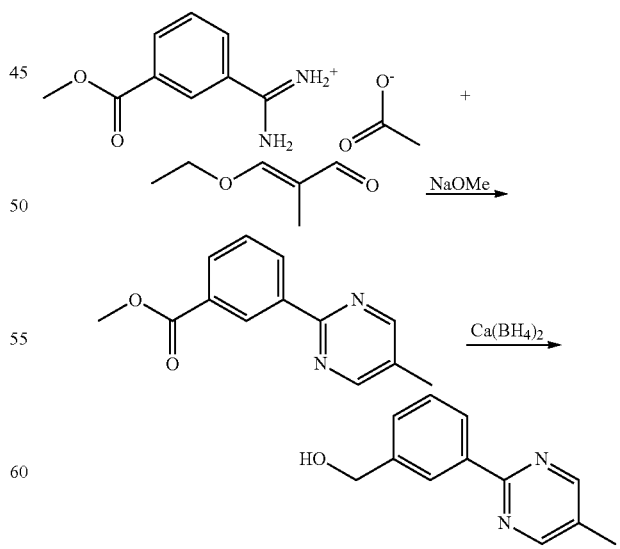

Step 1:

1.31 ml (11.0 mmol) of 3-ethoxymethacrolein and 2.04 ml (11.0 mmol) of a 30% solution of sodium ethoxide in methanol are added to a suspension of 2.41 g (10.0 mmol) of methyl 3-carbamimidoylbenzoate acetate in 40 ml of methanol, and the resultant solution is stirred at 50° C. for 18 hours. The reaction mixture is evaporated in vacuo, and water is added. The resultant precipitate is filtered off with suction, washed with water and dried in vacuo: methyl 3-(5-methylpyrimidin-2-yl)benzoate as colourless crystals; LCMS 229.

Step 2:

600 mg (5.41 mmol) of powdered calcium chloride are added to a suspension of 400 mg (10.6 mmol) of sodium borohydride in 20 ml of THF, and the mixture is stirred at room temperature for 1.5 hours. A solution of 751 mg (3.29 mmol) of methyl 3-(5-methylpyrimidin-2-yl)benzoate in 10 ml of THF is added dropwise to this suspension with stirring, and the mixture is stirred at room temperature for 18 hours. 10 ml of 1 N NaOH, water and dichloromethane are added to the reaction mixture, which is then filtered. The organic phase of the filtrate is separated off, dried over sodium sulfate and evaporated. The residue is chromatographed on a silica-gel column with dichloromethane/methanol as eluent: [3-(5-methylpyrimidin-2-yl)phenyl]methanol as colourless solid; LCMS 201.

Preparation of [3-(5-bromopyrimidin-2-yl)phenyl]methanol

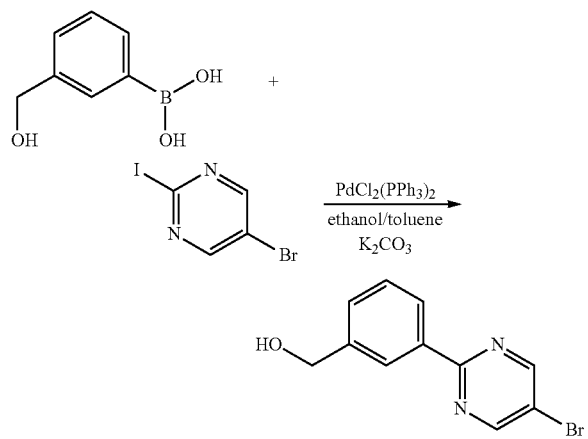

A solution of 70.0 g (660 mmol) of sodium carbonate in 325 ml of water is added to a solution, kept under nitrogen, of 95.0 g (332 mmol) of 5-bromo-2-iodopyrimidine in 325 ml of toluene, and the mixture is heated to 80° C. 2.3 g (3.3 mmol) of bis(triphenylphosphine)palladium(II) chloride are added, and a solution of 50.0 g (329 mmol) of 3-(hydroxymethyl) benzeneboronic acid in 650 ml of ethanol is subsequently added dropwise. The reaction mixture is stirred at 80° C. for 18 hours. The reaction mixture is cooled to room temperature and filtered. 1 l of ethyl acetate and 1 l of water are added to the filtrate. The organic phase is separated off, dried over sodium sulfate and evaporated. The residue is recrystallised from 2-propanol: [3-(5-bromopyrimidin-2-yl)-phenyl] methanol as pale-yellow crystals; m.p. 115-116° C.; LCMS 265, 267.

Preparation of methyl (E)-3-[2-(3-hydroxymethylphenyl)pyrimidin-5-yl]acrylate

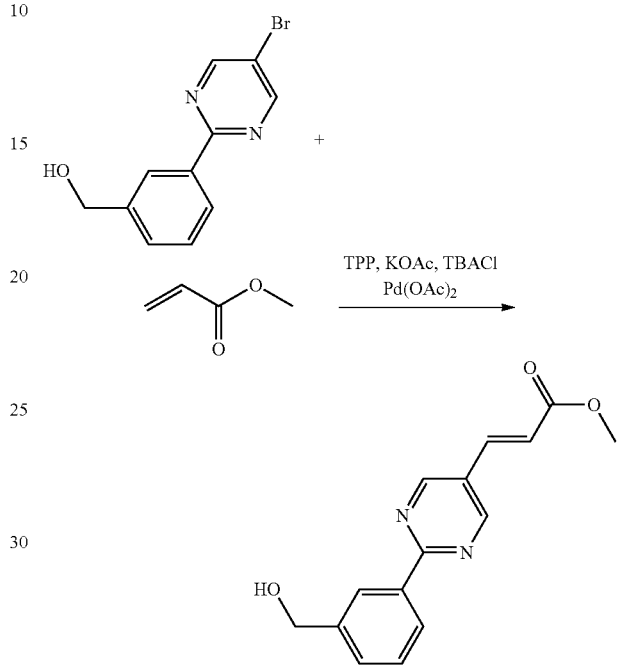

100 mg (0.38 mmol) of [3-(5-bromopyrimidin-2-yl)phenyl]methanol and 51 µl (0.56 mmol) of methyl acrylate are suspended in 2 ml of DMF, and 20 mg (0.075 mmol) of triphenylphosphine, 222 mg (2.26 mmol) of potassium acetate and 157 mg (0.57 mmol) of tetra-n-butylammonium chloride are added. The reaction mixture is degassed, flushed with argon, and 17 mg (0.075 mmol) of palladium(II) acetate are added under an argon atmosphere. The mixture is heated at 80° C. for 2 h. After cooling, water is added, during which a pale-grey precipitate forms. This is filtered off with suction, washed with water and dried in vacuo. The product is reacted further without further purification; yield: 111 mg; HPLC: Rt.=2.42 min (method A); LC-MS: 271 (M+H).

Preparation of tea-butyl {(E)-3-[2-(3-hydroxymethylphenyl)pyrimidin-5-yl]allyl}-carbamate

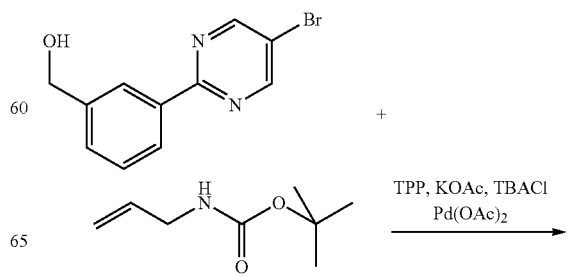

-continued

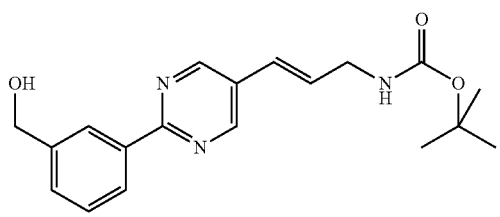

812 mg (3.06 mmol) of [3-(5-bromopyrimidin-2-yl)phenyl]methanol and 722 mg (4.59 mmol) of tert-butyl N-allylcarbamate are suspended in 16 ml of DMF, and 160 mg (0.61 mmol) of triphenylphosphine, 1.8 g (4.6 mmol) of potassium acetate and 1.28 g (4.59 mmol) of tetra-n-butylammonium chloride are added. The reaction mixture is degassed and flushed with argon, and 137 mg (0.0.61 mmol) of palladium (II) acetate are added under an argon atmosphere. The mixture is heated at 80° C. for 2 h. After cooling, the mixture is filtered off through kieselguhr with suction, and the filtrate is added to water and extracted with 2×100 ml of ethyl acetate, dried over sodium sulfate and evaporated. The product was reacted further without purification. Yield: 380 mg; HPLC: Rt.=2.66 min (method A); LC-MS: 342 (M+H).

Preparation of tea-butyl {3-[2-(3-hydroxymethylphenyl)pyrimidin-5-yl]propyl}-carbamate

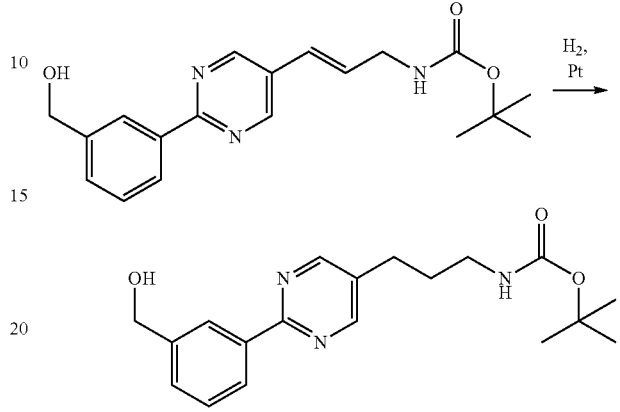

280 mg (0.82 mmol) of tert-butyl {(E)-3-[2-(3-hydroxymethylphenyl)pyrimidin-5-yl]allyl}carbamate are dissolved in 10 ml of THF, shaken at room temperature for 17 h with 300 mg of platinum on active carbon (5%, comprises 56% of water) under a hydrogen atmosphere. The catalyst is filtered off with suction, and the filtrate is evaporated to dryness. Yield: 289 mg; HPLC: Rt.=2.60 min (method A), LC-MS: 344 (M+H).

Preparation of {3-[5-(4-methylpiperazin-1-yl)pyrimidin-2-yl]phenyl}methanol

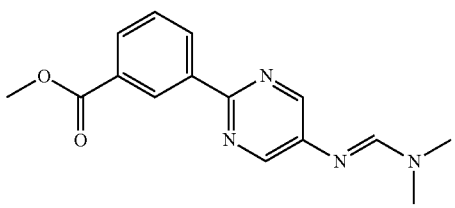

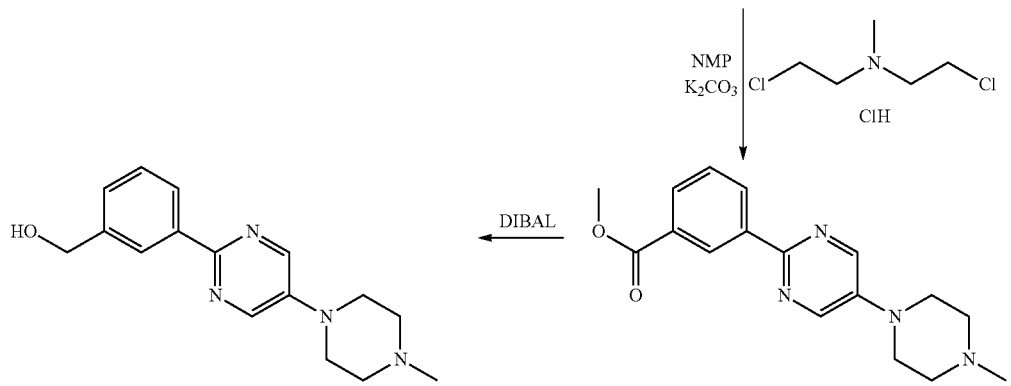

Step 1:

10.2 g (35.9 mmol) of methyl 3-[5-(dimethylaminomethyleneamino)pyrimidin-2-yl]benzoate are suspended in 1 l of methanol. 5.3 ml (107.3 mmol) of fuming sulfuric acid are added dropwise with gentle cooling (about 5-10° C.) (note, strongly exothermic reaction). When the addition is complete, the mixture is stirred firstly for 30 min at RT and subsequently at an oil-bath temperature of 88° C. The reaction is followed by means of HPLC. After 20 h, the clear, dark-yellow solution is evaporated to dryness. The residue is dissolved in 600 ml of ethyl acetate and washed with 2×150 ml of 1 N NaOH and 2×1 N HCl, dried over sodium sulfate and evaporated.

Yield: 3 g; HPLC: Rt.=2.17 min (method A); LC-MS: 300 (M+H).

Step 2:

2.5 g (10.9 mmol) of methyl 3-(5-aminopyrimidin-2-yl)benzoate are dissolved in 10 ml of NMP, 2.59 g (18.5 mmol) of potassium carbonate and 3.6 g (18.5 mmol) of bis(2-chloroethyl)ethylamine hydrochloride are added. The suspension is stirred at 120° C. for 15 h under an argon atmosphere. The mixture is subsequently stirred at 140° C. for a further 12 h. After cooling to room temperature, the reaction mixture is stirred into 150 ml of water. The resultant precipitate is filtered off through kieselguhr with suction and discarded. The filtrate is adjusted to pH=14 using 32% NaOH. The slightly cloudy solution is extracted with 2×200 ml of ethyl acetate. The combined organic phases are washed with saturated sodium chloride solution, dried over sodium sulfate and evaporated to dryness and dried in vacuo. The product is reacted further without further purification.

Yield: 860 mg; HPLC: Rt.=2.11 min (method A); LC-MS: 313 (M+H).

Step 3:

860 mg (2.75 mmol) of methyl 3-[5-(4-methylpiperazin-1-yl)pyrimidin-2-yl]-benzoate are dissolved in 16 ml of THF, and 13.8 ml (13.8 mmol) of 1 M diisobutylaluminium hydride in THF are added dropwise at room temperature, and the reaction mixture is stirred at room temperature for 1 h. A further 13.8 ml 13 (13.8 mmol) of 1 M diisobutylaluminium hydride in THF are added dropwise, and the reaction mixture is stirred at room temperature for 1 h. 3 ml of saturated sodium sulfate solution are added to the reaction mixture with ice-cooling. Dichloromethane is added to the gelatinous mixture, which is then stirred for 30 min and filtered. The filtrate is dried over sodium sulfate and evaporated.

Yield: 300 mg, yellow solid. The product is reacted further without further purification; HPLC: 1.68 min (method A); LC-MS: 285 (M+H).

Preparation of tert-butyl 4-[2-(3-hydroxymethylphenyl)pyrimidin-5-yl]piperazine-1-carboxylate

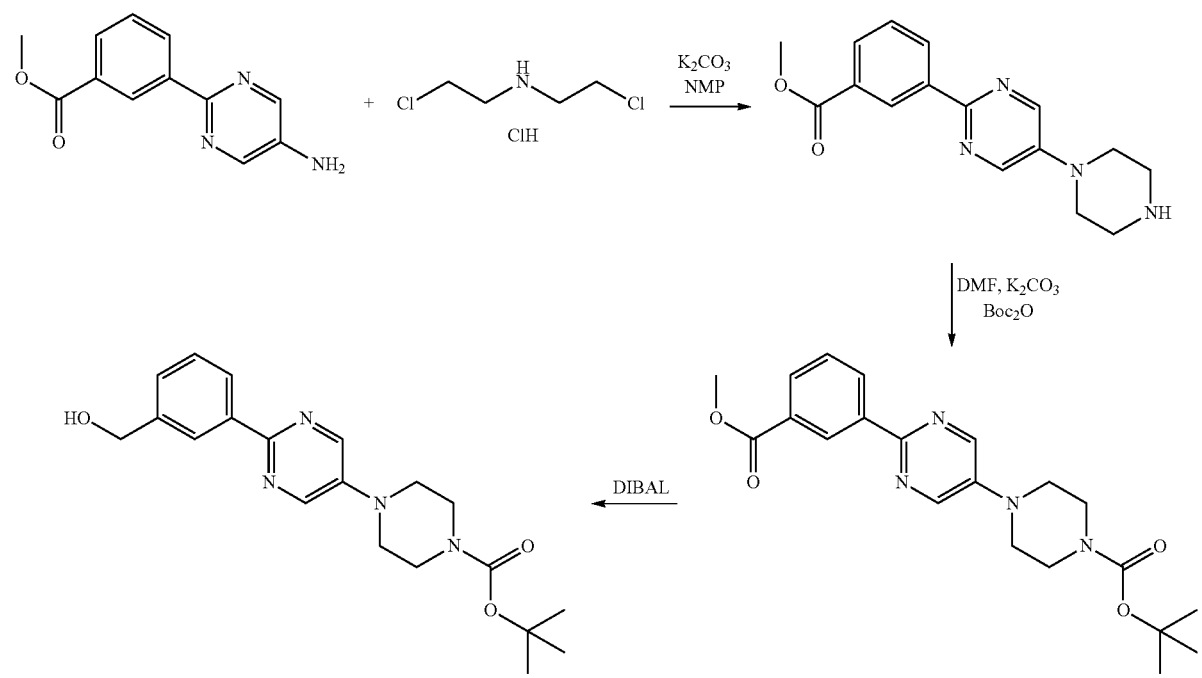

Step 1:

3.2 g (13.95 mmol) of methyl 3-(5-aminopyrimidin-2-yl)benzoate are dissolved in 80 ml of NMP, 4.73 g (25.96 mmol) of bis(2-chloroethyl)ammonium chloride and 3.13 g (23.73 mmol) of potassium carbonate are added. The suspension is stirred at 130° C. for 7 days under an argon atmosphere. The reaction mixture is filtered, the filtrate is stirred into 1 l of diethyl ether, during which a residue deposits as an oil. The organic phase is separated off and discarded. 500 ml of ethyl acetate and 200 ml of saturated sodium hydrogencarbonate solution are added to the residue, the organic phase is separated off, and the aqueous phase is again extracted with 500 ml of ethyl acetate. The organic phases are combined, dried over sodium sulfate and evaporated. The residue is reacted further without further work-up.

Yield: 2.4 g; HPLC: Rt.=2.07 min (method A); LC-MS: 299 (M+H).

Step 2:

2.4 g (5.4 mmol) of methyl 3-(5-piperazin-1-ylpyrimidin-2-yl)benzoate is dissolved in 15 ml of DMF, 2.98 g (21.6 mmol) of potassium carbonate and 1.5 ml (7.0 mmol) of di-tert-butyl dicarbonate are added, and the mixture is stirred at room temperature for 30 min. The reaction mixture is filtered, and the filtrate is evaporated. The residue is taken up in 200 ml of ethyl acetate and 50 ml of saturated sodium hydrogencarbonate solution. The organic phase is separated off and washed with 50 ml of 1 N HCl, dried over sodium sulfate and evaporated. The product is reacted further without further purification.

Yield: 1.1 g; HPLC: 3.18 min (method A); LC-MS: 399 (M+H).

Step 3:

862 mg (2.16 mmol) of tert-butyl 4-[2-(3-methoxycarbonylphenyl)pyrimidin-5-yl]piperazine-1-carboxylate are dissolved in 15 ml of THF, and 10.8 ml (10.8 mmol) of 1 M diisobutylaluminium hydride in THF are added at room temperature. The reaction mixture is stirred at room temperature for 1 h. 3 ml of saturated sodium sulfate solution are added to the reaction mixture with ice-cooling. 30 ml of dichloromethane and 5 ml of methanol are added to the gelatinous mixture, which is then stirred for 10 min and filtered off through kieselguhr with suction. The filtrate is dried over sodium sulfate and evaporated. The residue is dissolved in dichloromethane, filtered, and the filtrate is evaporated. The product is reacted further without further purification; yield:

677 mg; HPLC: 2.66 min (method A); LC-MS: 371 (M+H).

Preparation of (3-{5-[1-(2-morpholin-4-ylethyl)-1H-pyrazol-4-yl]pyrimidin-2-yl}-phenyl)methanol

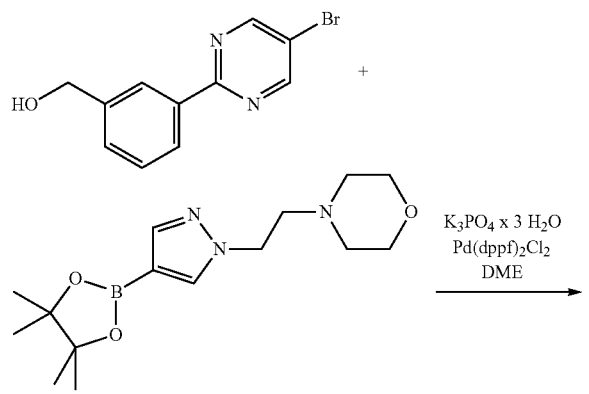

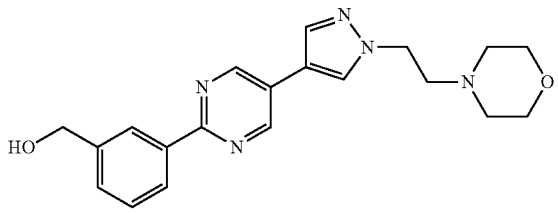

Under an argon atmosphere, 2.82 g (10 mmol) of [3-(5-bromopyrimidin-2-yl)-phenyl]methanol are dissolved in 100 ml of ethylene glycol dimethyl ether, 3.38 g (10 mmol) of 4-{2-[4-(4,4,5,5-tetramethyl-1,3,2-dioxaborolan-2-yl)pyrazol-1-yl]ethyl}morpholine and 4.25 g (20 mmol) of tripotassium phosphate trihydrate are added. The reaction mixture is evacuated twice and flushed with argon. 840 mg (1.2 mmol) of bis(triphenylphosphine)palladium(II) chloride are added, the mixture is again evacuated and flushed argon. The reaction mixture is stirred at 80° C. for 16 hours. The reaction mixture is diluted with dichloromethane and water and filtered through Celite. The organic phase is separated off, washed with water again, the organic phase is dried over sodium sulfate and evaporated to dryness. The residue is recrystallised from isopropanol; yield: 2.74 g, LCMS: 366 (M+H).

The following compounds can be prepared analogously. In some cases, the crude products are purified by means of column chromatography on silica gel.

| Compound No. | Name and/or structure | LCMS [M + H] | Rt. in min |
|---|---|---|---|
|  |  | 436 |  |
|  |  | 350 |  |

Preparation of the Benzylamines from the Benzyl Alcohols

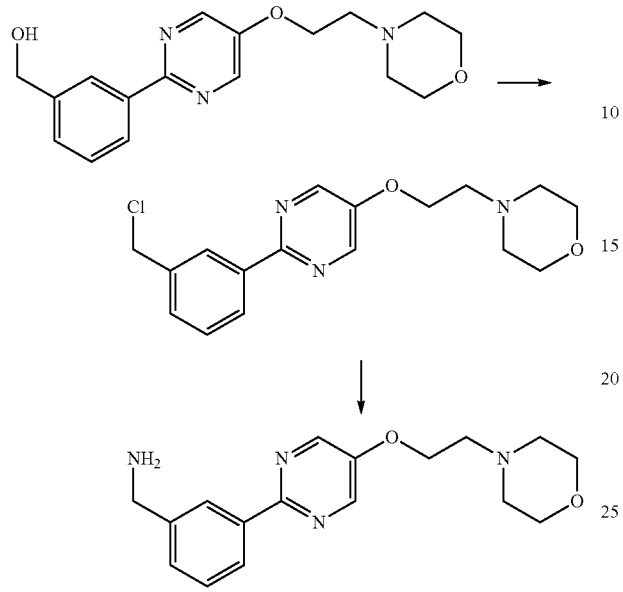

Step 1:

16.5 ml (227 mmol) of thionyl chloride are added to 3.66 g (11.6 mmol) of {3-[5-(2-morpholin-4-ylethoxy)pyrimidin-2-yl]phenyl}methanol, and the mixture is stirred at room temperature for 30 min. Diethyl ether is added to the reaction mixture, whereupon a precipitate forms. The supernatant is decanted off, the residue is stirred with 50 ml of acetonitrile, and the crystals formed are filtered off with suction, washed with acetonitrile and diethyl ether and dried.

Yield: 4.0 g; pale-beige crystals; Rt. 2.24 min (method A); LCMS: 334 (M+H).

Step 2:

587 mg (2.70 mmol) of di-tert-butyl iminodicarboxylate are dissolved in 10 ml of ethyl methyl ketone, 2.64 g (8.10 mmol) of caesium carbonate are added, and the mixture is stirred for 90 min. 1.0 g (2.70 mmol) of 4-{2-[2-(3-chloromethylphenyl)pyrimidin-5-yloxy]ethyl}morpholine and 29 mg (0.22 mmol) of lithium iodide are subsequently added. The reaction mixture is stirred at room temperature for 16 h and at 70° C. for 6 h. The reaction mixture is filtered, and the residue is washed with ethyl acetate, the filtrate is evaporated and dissolved in ethyl acetate. The organic phase is washed with saturated sodium hydrogencarbonate solution and water, dried over sodium sulfate and evaporated. 5 ml of dioxane and 5 ml of 4N HCl in dioxane are added to the crude product, and the mixture is stirred at room temperature. A precipitate forms, the organic phase is decanted off, and the residue is dissolved in water. The aqueous phase is washed with ethyl acetate, adjusted to pH 12 using 32% sodium hydroxide solution and extracted twice with ethyl acetate. The combined organic phases are dried over sodium sulfate and evaporated.

Yield: 510 mg; Rt.=1.52 min; LCMS 315 (M+H).

Alternative Synthetic Route:

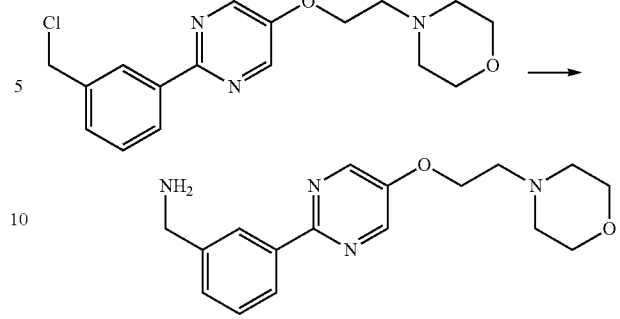

5.20 g (14.0 mmol) of 4-{2-[2-(3-chloromethylphenyl)pyrimidin-5-yloxy]-ethyl}morpholine are dissolved in 36 ml of 25% ammonia solution and 36 ml of n-butanol. The reaction mixture is irradiated in the microwave at 120° C. for 20 min. The organic phase is separated off, and the aqueous phase is again extracted with butanol. The combined organic phases are dried over sodium sulfate, and the butanol is distilled off under reduced pressure, and the product is subsequently dried in a high vacuum. The product was reacted further without further purification; yield: 2.26 g.

Alternative Synthesis for the Preparation of Benzylamines from Benzyl Alcohols

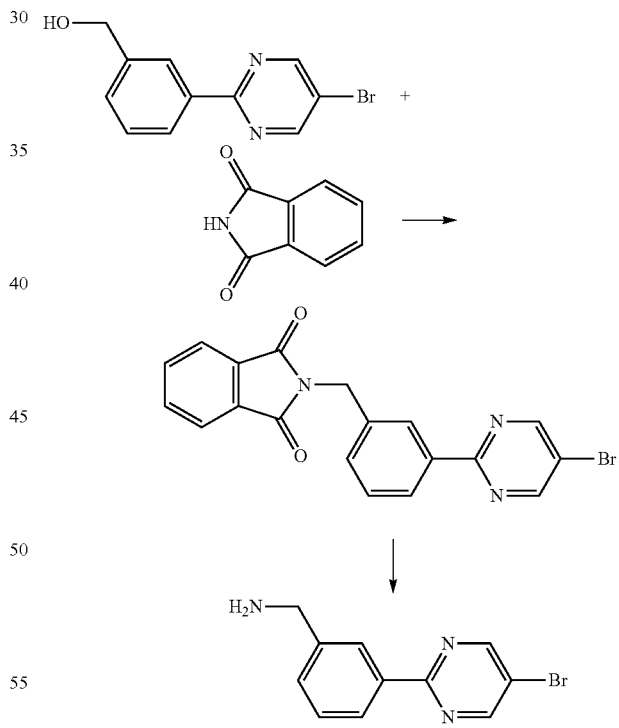

Step 1:

5.0 g (18.9 mmol) of [3-(5-bromopyrimidin-2-yl)phenyl] methanol and 3.05 g (20.7 mmol) of phthalimide are dissolved in 150 ml of THF, 6.9 g (20.7 mmol) of polymer-bound triphenylphosphine (3 mol/g) are added, and the mixture is shaken at room temperature for 15 min. 4.78 g (20.7 mmol) of di-tert-butyl azodicarboxylate is subsequently added and shaken at room temperature under a nitrogen atmosphere for 18 h. The reaction mixture is filtered, the residue is washed intensively with DMF and DMF/methanol, and the filtrate is evaporated. The residue is taken up in ethyl acetate and washed with water, dried and evaporated. The residue is purified by means of column chromatography on silica gel; HPLC: Rt.=3.41 min (method A), LCMS: 394/396 (M+H).

Step 2:

60 ml of ethanol are added to the product from step 1, and 5 equiv. of hydrazine hydrate are added. The reaction mixture is stirred at 70° C. for 18 h, evaporated and taken up in ethyl acetate and saturated sodium hydrogen-carbonate solution. The organic phase is separated off, dried and purified by means of column chromatography on silica gel; HPLC: Rt.=2.11 min (method A), LCMS: 264/266 (M+H).

The following benzylamines are prepared analogously to the procedures described:

| Compound No. | Name and/or structure | LCMS [M + H] | Rt. in min |
|---|---|---|---|
| | 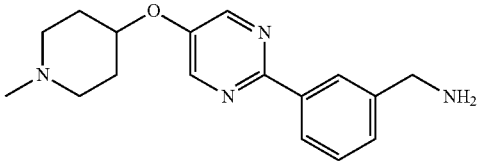 | 299 | |
| | 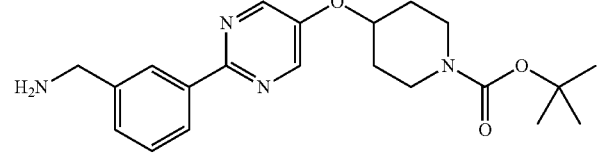 | 385 | |
| | 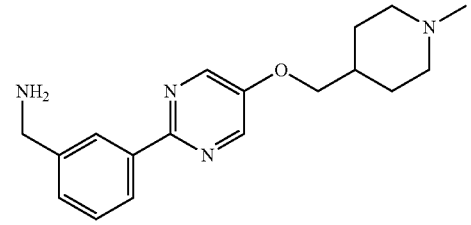 [SMILES: CN1CCC(COc2cnc(-c3cccc(CO)c3)nc2)CC1] | 313 | |
| | 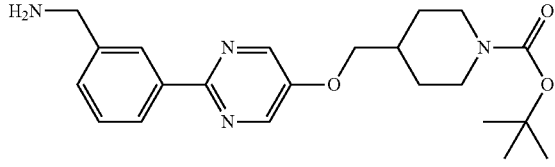 [SMILES: CC(C)(C)OC(=O)N1CCC(COc2cnc(-c3cccc(CN)c3)nc2)CC1] | 399 | |
| | 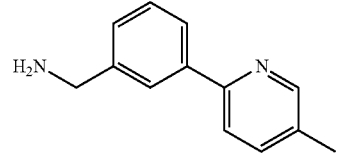 | 199 | |
| | 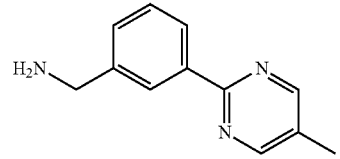 | 200 | |
| | 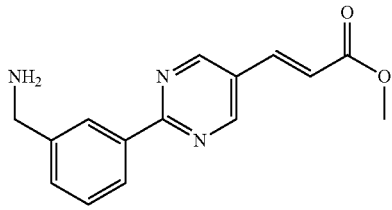 [SMILES: COC(=O)/C=C/c1cnc(-c2cccc(CN)c2)nc1] | 270 | |

-continued

| Compound No. | Name and/or structure | LCMS [M + H] | Rt. in min |
|---|---|---|---|
| | | 343 | |
| | | 284 | |
| | | 370 | |
| | | 301 | |
| | | 365 | |
| | | 435 | |
| | | 349 | |

Preparation of 6-(1-methyl-1H-pyrazol-4-yl)-1-{3-[5-(2-morpholin-4-ylethoxy)-pyrimidin-2-yl]benzyl}-1H-1,2,3-triazolo[4,5-b]pyrazine ("A2")

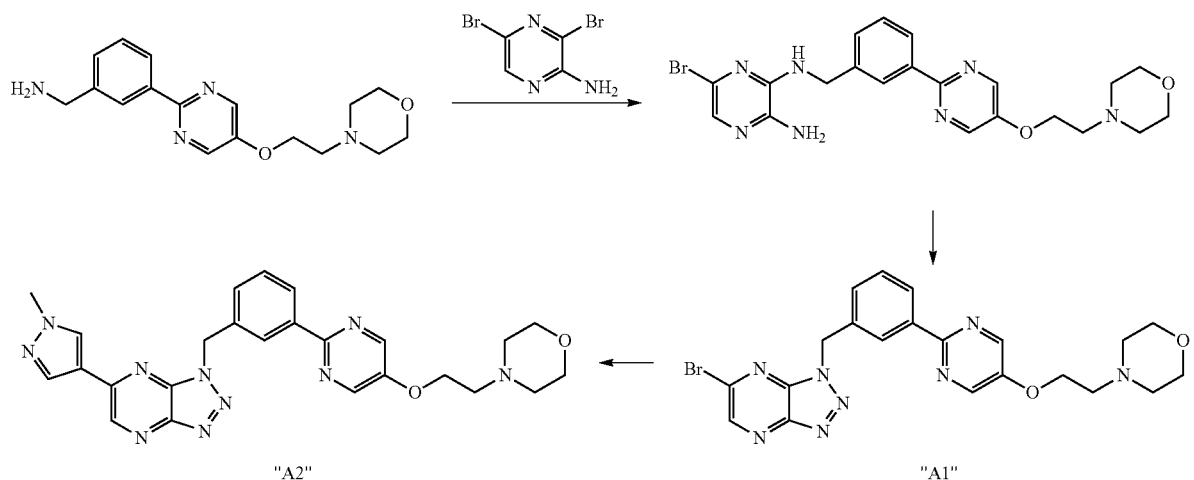

Step 1:
800 µl of diisopropylethylamine are added to 400 mg (1.27 mmol) of 3-[5-(2-morpholin-4-ylethoxy)pyrimidin-2-yl]benzylamine. 319 mg (1.26 mmol) of 2-amino-3,5-dibromopyrazine are added to this suspension, and the reaction mixture is stirred at 130° C. for 5 hours. Dichloromethane and water are added to the brown reaction solution, the organic phase is dried over sodium sulfate and evaporated. The crude product is purified by means of column chromatography on silica gel.

Yield: 396 mg of brown oil; Rt.=2.20 min (method A), LC-MS: 487 (M+H).

Step 2:
396 mg (0.81 mmol) of 5-bromo-N*3*-{3-[5-(2-morpholin-4-ylethoxy)pyrimidin-2-yl]benzyl}pyrazine-2,3-diamine are dissolved in 7 ml of water/acetic acid 1:1. A solution of 562 mg (8.14 mmol) of sodium nitrite in 3.5 ml of water is slowly added dropwise to this orange solution. During this addition, the temperature rises from 22° C. to 26° C. The mixture is stirred at room temperature for 1 hour. The mixture is subsequently stirred at an internal temperature of 65° C. for 4 hours.

The reaction mixture is evaporated, the residue is dissolved in water and neutralised using solid sodium hydrogencarbonate. A brown oil precipitates out. The latter is extracted with a mixture of ethyl acetate and a little methanol. The organic phase is dried and evaporated.

Some of the crude product is purified by means of preparative HPLC, the remainder is reacted further without further purification, giving 6-bromo-1-{3-[5-(2-morpholin-4-ylethoxy)pyrimidin-2-yl]benzyl}-1H-1,2,3-triazolo[4,5-b]-pyrazine ("A1"); product is in the form of the TFA salt;

$^1$H-NMR (500 MHz, DMSO-$d_6$) δ [ppm] 10.05 (b, 1H), 9.00 (s, 1H), 8.70 (s, 2H), 8.38 (s, 1H), 8.28 (m, 1H), 7.48-7.54 (m, 2H), 6.08 (s, 2H), 4.58 (b, 2H), 3.98 (b, 2H), 3.1-3.8 (b, 8H).

Step 3:
Under an argon atmosphere, 225 mg (0.24 mmol) of 6-bromo-1-{3-[5-(2-morpholin-4-ylethoxy)pyrimidin-2-yl]benzyl}-1H-1,2,3-triazolo[4,5-b]pyrazine are dissolved in 5 ml of ethylene glycol dimethyl ether, and 102 mg (0.48 mmol) of tripotassium phosphate trihydrate and 55 mg (0.26 mmol) of 1-methyl-4-(4,4,5,5-tetramethyl-1,3,2-dioxaborolan-2-yl)-1H-pyrazole are added. The reaction mixture is evacuated and flushed with argon twice. 14 mg (0.02 mmol) of bis (triphenylphosphine)palladium(II) chloride are added, the mixture is again evacuated and flushed argon. The reaction mixture is stirred at 80° C. for 16 hours. 10 ml of water are added to the reaction mixture, during which an oil precipitates out. This is extracted with dichloromethane and with dichloromethane comprising about 10% of MeOH, the aqueous phase is adjusted to pH 14 using 32% NaOH and again extracted with dichloromethane. The combined organic phases are dried over sodium sulfate and purified by means of preparative HPLC, giving 42 mg of 6-(1-methyl-1H-pyrazol-4-yl)-1-{3-[5-(2-morpholin-4-ylethoxy)pyrimidin-2-yl]benzyl}-1H-1,2,3-triazolo[4,5-b]-pyrazine ("A2"); the product is in the form of the TFA salt; Rt.=2.26 (method A), LCMS: 499 (M+H);

$^1$H-NMR (500 MHz, DMSO-$d_6$) δ [ppm] 10.01 (b, 1H), 9.20 (s, 1H), 8.69 (s, 2H), 8.64 (s, 1H), 8.44 (s, 1H), 8.31 (s, 1H), 8.27 (d, 1H), 7.59 (d, 1H), 7.52 (t, 1H), 6.04 (s, 2H), 4.57 (b, 2H), 3.98 (b, 2H), 3.95 (s, 3H), 3.1-3.8 (b, 8H).

Preparation of 6-bromo-1-[3-(5-bromopyrimidin-2-yl)benzyl]-1H-1,2,3-triazolo[4,5-b]pyrazine ("B1")

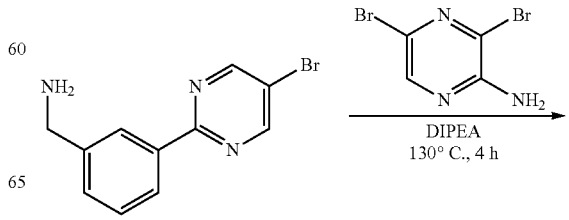

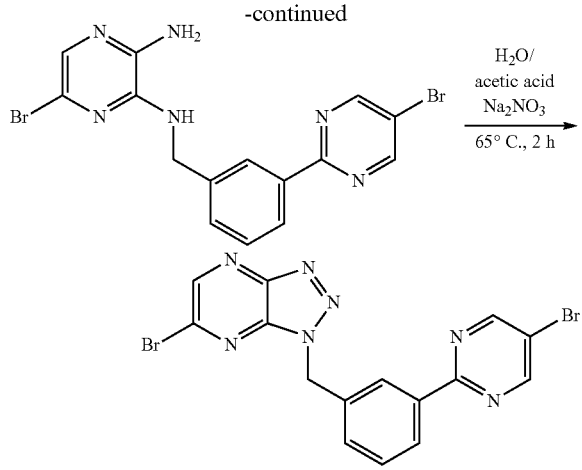

Step 1:

50 ml (294 mmol) of N-ethyl-N,N-diisopropylamine are added to 17.2 g (55.3 mmol) of 3-(5-bromopyrimidin-2-yl)benzylamine and 14.3 g (55.3 mmol) of 2-amino-3,5-dibromopyrazine. The reaction mixture is stirred at 130° C. for 4 h. The solution is filtered, the residue is dissolved in ethyl acetate and washed twice with water. The organic phase is dried over sodium sulfate and evaporated.

Yield: 24.85 g, HPLC: R$_t$=3.14 min (method B), LC-MS: [M+H]$^+$=437.

Step 2:

23.9 g (43.7 mmol) of 5-bromo-N3'-[3-(5-bromopyrimidin-2-yl)benzyl]-pyrazine-2,3-diamine are dissolved in 240 ml of water and 240 ml of acetic acid (96%), and 30.1 g (437 mmol) of sodium nitrite dissolved in 240 ml of water are added. The mixture is stirred at room temperature for 1 h and at 65° C. for 4 h. The reaction mixture is cooled, and the residue is filtered off with suction. The residue stirred with ether and reacted further without purification.

Yield: 15.5 g, HPLC: R$_t$=3.28 min (method C), LC-MS: [M+H]$^+$=448.

Preparation of 1-[3-(5-bromopyrimidin-2-yl)benzyl]-6-(1-methyl-1H-pyrazol-4-yl)-1H-1,2,3-triazolo[4,5-b]pyrazine ("B2")

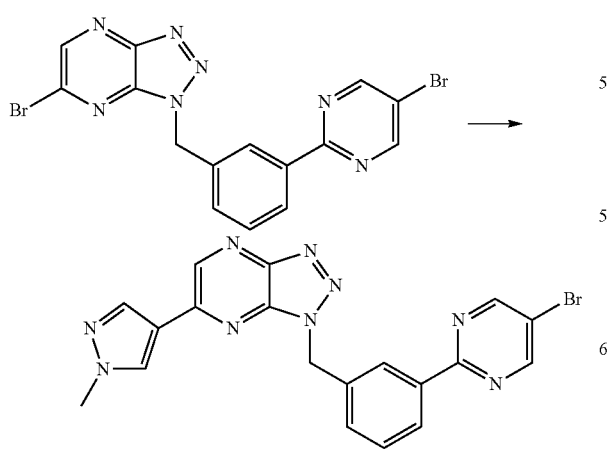

2.00 g (3.67 mmol) of 6-bromo-1-[3-(5-bromopyrimidin-2-yl)benzyl]-1H-1,2,3-triazolo[4,5-b]pyrazine, 840 mg (4.04 mmol) of 1-methyl-4-(4,4,5,5-tetramethyl-1,3,2-dioxaborolan-2-yl)-1H-pyrazole and 778 mg (7.34 mmol) of sodium carbonate are suspended in 3.7 ml (204 mmol) of water and 15 ml of N,N-dimethylformamide, degassed, evacuated and flushed with nitrogen a number of times. 257 mg (0.367 mmol) of bis(triphenylphosphine)palladium-(II) chloride are added, and the mixture is again evacuated and flushed with nitrogen. The reaction mixture is stirred at 80° C. for 24 h. The reaction mixture is filtered and washed with ethyl acetate and evaporated. The residue is stirred with isopropanol and reacted further without additional purification.

HPLC: R$_t$=2.96 min (method A), LC-MS: [M+H]$^+$=448/450, R$_t$=2.36 min (method C);

$^1$H-NMR (500 MHz, DMSO-d$_6$) δ [ppm] 9.19 (s, 1H), 9.07 (s, 2H), 8.62 (s, 1H), 8.52 (s, 1H), 8.33 (s, 1H), 8.32 (d, J=5.9, 1H), 7.64 (d, J=7.7, 1H), 7.55 (t, J=7.7, 1H), 6.06 (s, 2H), 3.95 (s, 3H).

The following compounds are prepared analogously

3-{3-[3-(5-bromopyrimidin-2-yl)benzyl]-3H-1,2,3-triazolo[4,5-b]byrazin-5-yl}-benzonitrile ("B3")

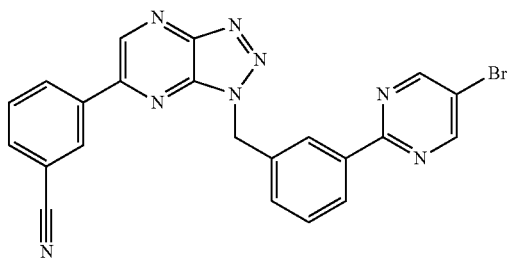 [SMILES: N#Cc1cccc(-c2cnc3nnn(Cc4cccc(-c5ncc(Br)cn5)c4)c3n2)c1]

HPLC: R$_t$=3.34 min (method A), LC-MS: [M+H]$^+$=469/471;

$^1$H-NMR (500 MHz, DMSO-d$_6$) δ [ppm] 9.07 (s, 2H), 8.73 (s, 1H), 8.37 (s, 1H), 8.33 (m, 1H), 7.89 (s, 1H), 7.76 (m, 1H), 7.72-7.64 (m, 2H), 7.51 (m, 1H), 7.47 (m, 1H), 2.54 (s, 2H).

1-[3-(5-bromopyrimidin-2-yl)benzyl]-6-(3,5-difluorophenyl)-1H-1,2,3-triazolo[4,5-b]pyrazine ("B4")

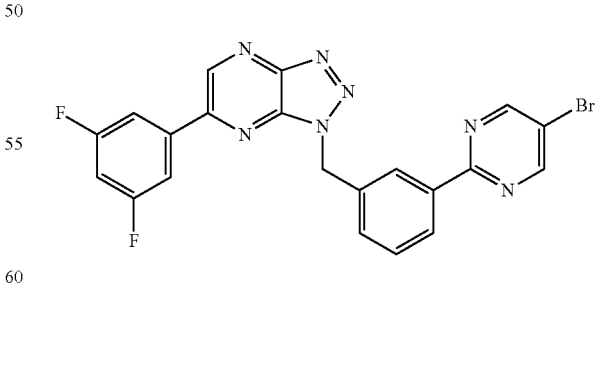

HPLC: $R_t$=3.56 min (method A), LC-MS: [M+H]⁺=480/482.

Preparation of 1-[3-(5-bromopyrimidin-2-yl)benzyl]-6-(1-methyl-1H-pyrazol-4-yloxy)-1H-1,2,3-triazolo[4,5-b]pyrazine ("B5")

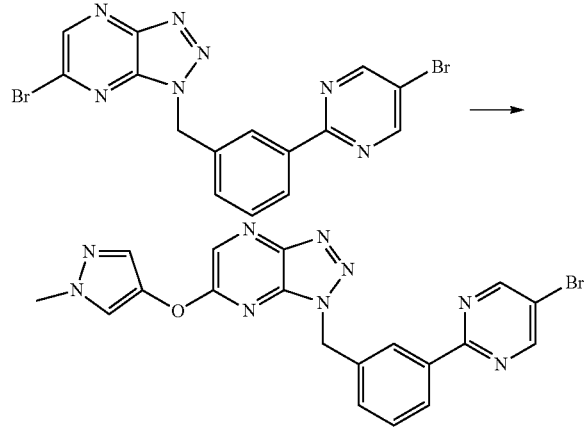

500 mg (0.932 mmol) of 6-bromo-1-[3-(5-bromopyrimidin-2-yl)benzyl]-1H-1,2,3-triazolo[4,5-b]pyrazine, 213 mg (1.03 mmol) of 1-methyl-4-(4,4,5,5-tetramethyl-1,3,2-dioxaborolan-2-yl)-1H-pyrazole and 396 mg (1.86 mmol) of tripotassium phosphate trihydrate are suspended in 20 ml of ethylene glycol dimethyl ether, degassed, evacuated and flushed with nitrogen a number of times. 65.4 mg (0.093 mmol) of bis(triphenylphosphine)palladium(II) chloride (15.2% of Pd) are added, and the mixture is again evacuated and flushed with nitrogen. The reaction mixture is stirred at 80° C. for 24 h. The reaction mixture is filtered, water is added to the filtrate, and the mixture is extracted with ethyl acetate. The organic phase is dried over sodium sulfate, evaporated under reduced pressure in a rotary evaporator and purified column-chromatically on silica gel.

Yield: 38 mg, HPLC: $R_t$=2.96 min (method C), LC-MS: [M+H]⁺=464/466;

¹H-NMR (500 MHz, DMSO-d₆) δ [ppm] 9.06 (s, 2H), 8.65 (s, 1H), 8.43 (s, 1H), 8.32 (d, J=7.4, 1H), 8.11 (s, 1H), 7.67 (s, 1H), 7.58 (d, J=7.6, 1H), 7.54 (t, J=7.6, 1H), 6.01 (s, 2H), 3.85 (s, 3H).

The following compounds are prepared analogously:

3-{3-[3-(5-bromopyrimidin-2-yl)benzyl]-3H-1,2,3-triazolo[4,5-b]pyrazin-5-yloxy}benzonitrile ("B6")

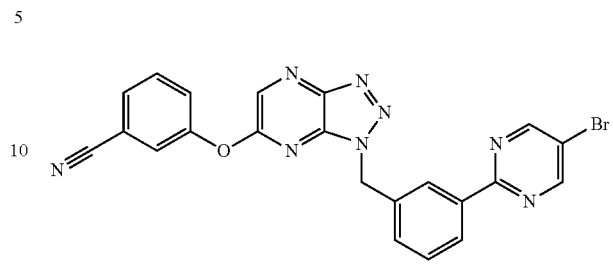

The crude product is purified by means of preparative HPLC.

HPLC: $R_t$=3.25 min (method A), LC-MS: [M+H]⁺=485/487;

¹H-NMR (500 MHz, DMSO-d₆) δ [ppm] 9.06 (s, 2H), 8.73 (s, 1H), 8.33 (s, 1H), 8.29 (d, J=7.8, 1H), 7.89 (s, 1H), 7.75 (dd, J=1.5, 7.2, 1H), 7.68 (m, 1H), 7.51-7.41 (m, 3H), 5.82 (s, 2H).

1-[3-(5-bromopyrimidin-2-yl)benzyl]-6-(3,5-difluorophenoxy)-1H-1,2,3-triazolo[4,5-b]pyrazine ("B7")

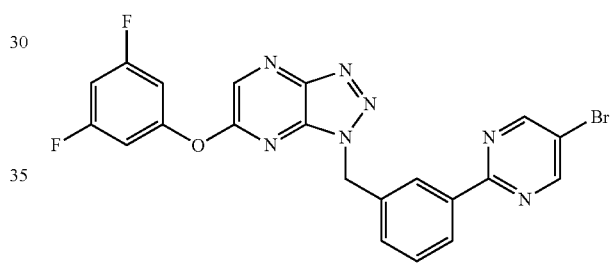

HPLC: $R_t$=3.52 min (method A), LC-MS: [M+H]⁺=495/497;

¹H-NMR (500 MHz, DMSO-d₆) δ [ppm] 9.06 (s, 2H), 8.72 (s, 1H), 8.36 (s, 1H), 8.32-8.28 (m, 1H), 7.50-7.44 (m, 2H), 7.20 (m, 2H), 7.18 (m, 1H), 5.87 (s, 2H).

Preparation of 6-(1-methyl-1H-pyrazol-4-yl)-1-(3-{5-[1-(2-pyrrolidin-1-yl-ethyl)-1H-pyrazol-4-yl]pyrimidin-2-yl}benzyl)-1H-1,2,3-triazolo[4,5-b]-pyrazine hydrochloride ("A24")

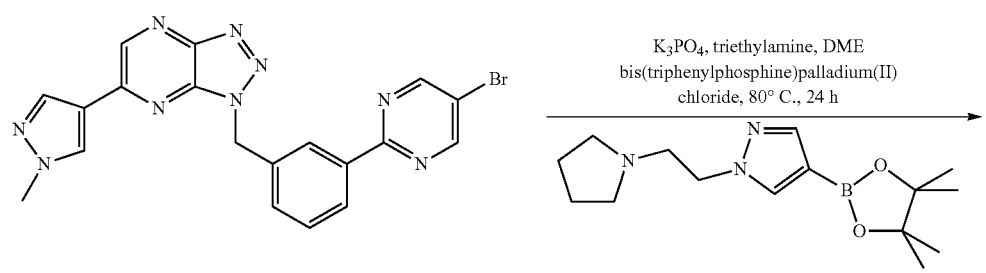

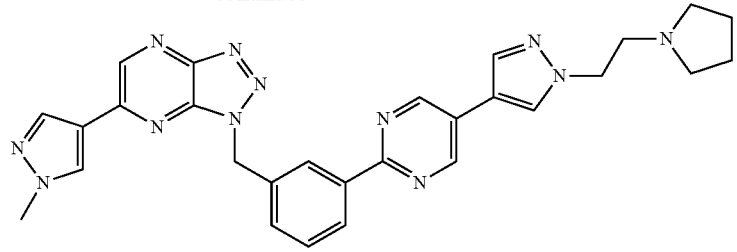

50 mg (0.104 mmol) of 1-[3-(5-bromopyrimidin-2-yl)benzyl]-6-(1-methyl-1H-pyrazol-4-yl)-1H-1,2,3-triazolo[4,5-b]pyrazine, 51.5 mg of 1-(2-pyrrolidin-1-ylethyl)-4-(4,4,5,5-tetramethyl-1,2,3-dioxaborolan-2-yl)-1H-pyrazole and 44.0 mg (0.207 mmol) of tripotassium phosphate trihydrate are suspended in 2 ml of ethylene glycol dimethyl ether, degassed, evacuated and flushed with nitrogen a number of times. 7.3 mg (0.010 mmol) of bis(triphenylphosphine)-palladium(II) chloride (15.2% of Pd) and 1.5 µl of triethylamine are added, and the mixture is again evacuated and flushed with nitrogen. The reaction mixture is stirred at 80° C. for 24 h. The reaction mixture is cooled, and ethyl acetate and water are added. The organic phase is separated off, the aqueous phase is extracted with ethyl acetate. The combined organic phases are subsequently dried over sodium sulfate, and the solvent is distilled off under reduced pressure. The aqueous phase is again extracted with dichloromethane, dried over sodium sulfate and evaporated under reduced pressure. The two residues are purified together by means of preparative HPLC. The residue is dissolved in methanol, methanolic HCl is added, and the mixture is evaporated in a Genevac. The product is in the form of the hydrochloride.

HPLC: $R_t$=2.36 min (method A), LC-MS: [M+H]$^+$=533;

$^1$H-NMR (500 MHz, DMSO-d$_6$) δ [ppm] 10.13 (s, 1H), 9.20 (s, 1H), 9.16 (s, 2H), 8.64 (s, 1H), 8.52 (s, 1H), 8.50 (s, 1H), 8.35 (d, J=7.8, 1H), 8.31 (s, 1H), 8.23 (s, 1H), 7.61 (d, J=7.8, 1H), 7.55 (t, J=7.7, 1H), 6.06 (s, 2H), 4.60 (t, J=6.2, 2H), 3.95 (s, 3H), 3.69 (t, J=6.1, 2H), 3.52-1.19 (m, 8H).

Preparation of 2-{3-[6-(1-methyl-1H-pyrazol-4-yl)-1,2,3-triazolo[4,5-b]-pyrazin-1-ylmethyl]phenyl}pyrimidin-5-ol ("B8")

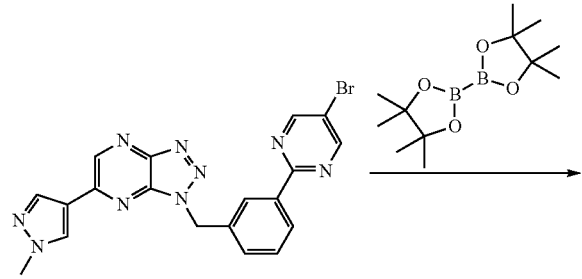

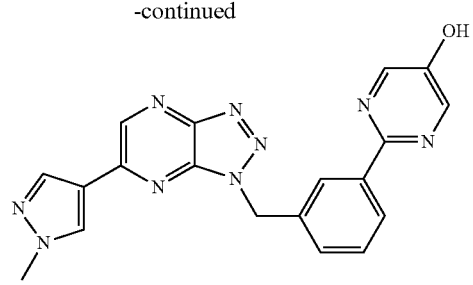

800 mg (1.66 mmol) of 1-[3-(5-bromopyrimidin-2-yl)benzyl]-6-(1-methyl-1H-pyrazol-4-yl)-1H-1,2,3-triazolo[4,5-b]pyrazine is suspended in 10 ml of THF and 1 ml of DMF, and 515 mg (1.99 mmol) of bis(pinacolato)diboron and 488 mg (4.97 mmol) of potassium acetate are added. The reaction mixture is evacuated and flushed with argon a number of times. 16.3 mg (0.023 mmol) of bis(triphenylphosphine)palladium(II) chloride is added, and the mixture is again evacuated and flushed with argon. The reaction mixture is stirred at 80° C. for 24 h. When the reaction of the starting material is complete, 255 mg (1.656 mmol) of sodium perborate trihydrate and 2 ml of water are added to the reaction mixture, which is then stirred at room temperature for 24 h. The reaction mixture is filtered off with suction and washed with ethyl acetate. The filtrate is subsequently adjusted to pH 12 using NaOH solution and extracted with ethyl acetate. The aqueous phase is neutralised using hydrochloric acid and extracted twice with ethyl acetate. The combined organic phases are then dried over sodium sulfate and evaporated under reduced pressure.

Yield: 320 mg, HPLC: $R_t$=2.42 min, LC-MS: [M+H]$^+$=385.

The following are prepared analogously:

2-{3-[3-(3-hydroxylpyrimidin-2-yl)benzyl]-3H-1,2,3-triazolo[4,5-b]pyrazin-5-yl}benzonitrile ("B9")

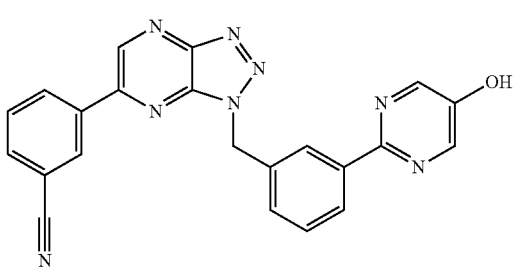 [SMILES: N#Cc1cccc(-c2cnc3nnn(Cc4cccc(-c5ncc(O)cn5)c4)c3n2)c1]

HPLC: $R_t$=2.81 min (method A), LC-MS: [M+H]$^+$=407;

¹H-NMR (500 MHz, DMSO-d₆) δ [ppm] 10.95 s, 1H), 9.59 (s, 1H), 8.81 (s, 1H), 8.68 (d, J=8.1, 1H), 8.54 (s, 1H), 8.44 (s, 2H), 8.24 (d, J=7.8, 1H), 8.09 (d, J=7.7, 1H), 7.84 (t, J=7.9, 1H), 7.58 (d, J=7.7, 1H), 7.49 (t, J=7.7, 1H), 6.17 (s, 2H).

2-{3-[6-(3,5-difluorophenyl)-1,2,3-triazolo[4,5-b]pyrazin-1-ylmethyl]phenyl}-pyrimidin-5-ol ("B10")

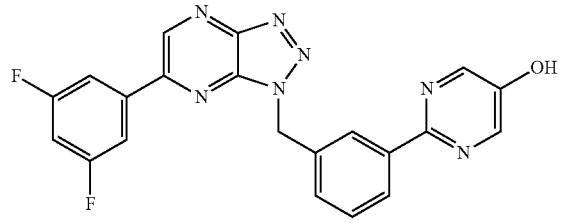 [SMILES: Oc1cnc(-c2cccc(Cn3nnc4ncc(-c5cc(F)cc(F)c5)nc43)c2)nc1]

HPLC: R$_t$=2.97 min (method A), LC-MS: [M+H]⁺=418;
¹HNMR (500 MHz, DMSO-d₆) δ [ppm] 10.59 (s, 1H), 9.55 (s, 1H), 8.60 (s, 1H), 8.43 (s, 2H), 8.23 (d, J=7.8, 1H), 8.11 (d, J=6.7, 2H), 7.58 (d, J=7.7, 1H), 7.53 (d, J=9.1, 1H), 7.49 (m, 1H), 6.16 (s, 2H).

2-{3-[6-(1-methyl-1H-pyrazol-4-yloxy)-1,2,3-triazolo[4,5-b]pyrazin-1-yl-methyl]phenyl}pyrimidin-5-ol ("B11")

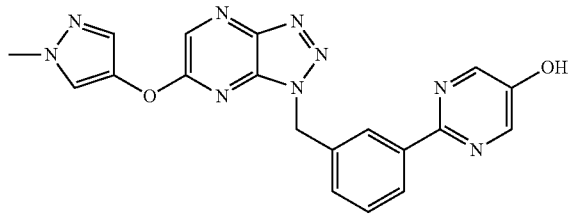 [SMILES: Cn1cc(Oc2cnc3nnn(Cc4cccc(-c5ncc(O)cn5)c4)c3n2)cn1]

LC-MS: [M+H]⁺=402.

3-{3-[3-(5-hydroxypyrimidin-2-yl)benzyl]-3H-1,2,3-triazolo[4,5-b]pyrazin-5-yloxy}benzonitrile ("B12")

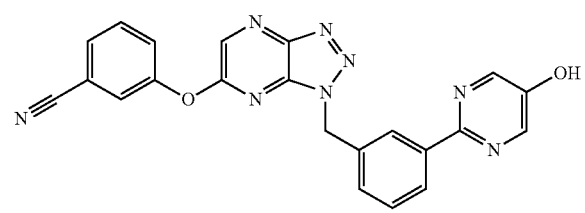 [SMILES: N#Cc1cccc(Oc2cnc3nnn(Cc4cccc(-c5ncc(O)cn5)c4)c3n2)c1]

LC-MS: [M₊H]⁺=423.

2-{3-[6-(3,5-difluorophenoxy)-1,2,3-triazolo[4,5-b]pyrazin-1-ylmethyl]-phenyl}pyrimidin-5-ol ("B13")

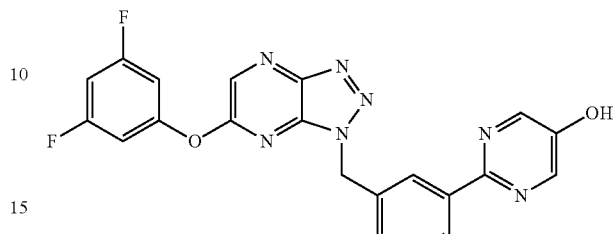

LC-MS: [M+H]⁺=434.

Preparation of dimethyl-[2(2-{3-[6-(1-methyl-1H-pyrazol-4-yl)-1,2,3-triazolo[4,5-b]pyrazin-1-ylmethyl]phenyl}pyrimidin-5-yloxy)ethyl]amine hydrochloride ("B14")

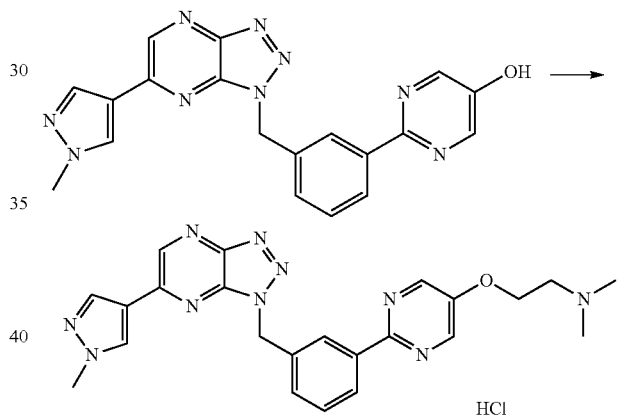

77.9 mg (0.234 mmol) of polymer-bound triphenylphosphine are added to 60.00 mg (0.156 mmol) of 2-{3-[6-(1-methyl-1H-pyrazol-4-yl)-1,2,3-triazolo-[4,5-b]pyrazin-1-ylmethyl]phenyl}pyrimidin-5-ol and 15.6 µl (0.156 mmol) of 2-(dimethylamino)ethanol in 5 ml of tetrahydrofuran and 1 ml of N,N-dimethylformamide. This reaction mixture is subsequently evacuated, flushed with nitrogen and shaken for 5 min. 53.8 mg (0.234 mmol) of di-tert-butyl azodicarboxylate are added to the reaction mixture, which is then again evacuated and flushed with nitrogen. The batch is shaken at RT for 4 h. 15.6 µl (0.156 mmol) of 2-(dimethylamino)ethanol, 77.9 mg (0.234 mmol) of polymer-bound triphenylphosphine and 53.8 mg (0.234 mmol) of di-tert-butyl azodicarboxylate were subsequently again added, and the mixture was shaken for 24 h. The reaction mixture is filtered off through Celite with suction and washed with DMF. The filtrate is subsequently evaporated under reduced pressure and purified by means of preparative HPLC. The residue is dissolved in methanol, methanolic HCl is added, and the mixture is evaporated in a Genevac. The product is in the form of the hydrochloride.

Yield: 20 mg, HPLC: R$_t$=2.20 min (method A), LC-MS: [M+H]⁺=457;

¹H-NMR (500 MHz, DMSO-d₆) δ [ppm] 10.31 (s, 1H), 9.19 (s, 1H), 8.69 (s, 2H), 8.64 (s, 1H), 8.45 (s, 1H), 8.31 (s, 1H), 8.27 (d, J=7.8, 1H), 7.57 (d, J=7.7, 1H), 7.52 (t, J=7.7, 1H), 6.04 (s, 2H), 4.60-4.56 (m, 2H), 3.95 (s, 3H), 3.56 (t, J=4.7, 2H), 2.86 (d, J=4.8, 6H).

The following compounds are prepared analogously:

| Compound No. | Name and/or structure | LCMS [M + H] | HPLC Rt. in min |
|---|---|---|---|
| "A4" | | 483 | |
| "A5" | | 569 | |
| "A6" | hydrochloride | 469 | 2.24 (method A) |

¹H-NMR (500 MHz, DMSO-d₆) δ [ppm] 9.19 (s, 1H), 8.74 (s, 1H), 8.69 (s, 2H), 8.63 (s, 1H), 8.42 (s, 1H), 8.31 (s, 1H), 8.26 (d, J = 7.8, 1H), 7.57 (d, J = 7.6, 1H), 7.51 (t, J = 7.7, 1H), 6.04 (s, 2H), 4.86 (m, 1H), 3.95 (s, 3H), 3.25 (d, J = 13.5, 2H), 3.08 (m, 2H), 2.15 (m, 2H), 1.92 (d, J = 12.4, 2H)

| Compound No. | Name and/or structure | LCMS [M + H] | HPLC Rt. in min |
|---|---|---|---|
| "A7" | | 497 | |
| "A8" | | 583 | |

-continued

| Compound No. | Name and/or structure | LCMS [M + H] | HPLC Rt. in min |
|---|---|---|---|
| "A9" | (structure shown) hydrochloride | 483 | 2.31 (method A) |

$^1$H-NMR (500 MHz, DMSO-d$_6$) δ [ppm] 9.19 (s, 1H), 8.86 (s, 1H), 8.64 (s, 2H), 8.55 (s, 1H), 8.44 (s, 1H), 8.31 (s, 1H), 8.25 (d, J = 7.7, 1H), 7.56 (d, J = 7.8, 1H), 7.51 (t, J = 7.7, 1H), 6.04 (s, 2H), 5.74 (s, 1H), 4.09 (d, J = 6.3, 2H), 3.95 (s, 3H), 3.27 (dd, J = 11.1, 26.7, 2H), 2.89 (t, J = 11.8, 2H), 2.12 (m, 1H), 1.92 (m, 2H), 1.51 (dd, J = 12.0, 22.2, 2H)

| | | | |
|---|---|---|---|
| "A10" | (structure shown) | 383 | |
| "A11" | (structure shown) | 384 | |
| "A12" | (structure shown) | 414 | |
| "A13" | (structure shown) | 428 | |

| Compound No. | Name and/or structure | LCMS [M + H] | HPLC Rt. in min |
|---|---|---|---|
| "A14" | | 454 | |
| "A15" | | 527 | |
| "A16" | | 427 | |
| "A17" | | 468 | |
| "A18" | | 554 | |
| "A19" | | 454 | |

US 8,435,986 B2

67                                                                              68

-continued

| Compound No. | Name and/or structure | LCMS [M + H] | HPLC Rt. in min |
|---|---|---|---|
| "A20" | | 485 | |
| "A21" | | 549 | |
| "A22" | | 619 | |
| "A23" | | 519 | |
| "A24" | | 533 | |
| "A25" | | 504 | |

-continued

| Compound No. | Name and/or structure | LCMS [M + H] | HPLC Rt. in min |
|---|---|---|---|
| "A26" | | 590 | |
| "A27" | hydrochloride | 490 | 2.51 (method A) |

¹H-NMR (500 MHz, DMSO-d₆) δ [ppm] 9.58 (s, 1H), 8.78 (s, 1H), 8.76-8.72 (m, 1H), 8.70 (s, 2H), 8.66 (d, J = 8.1, 1H), 8.53 (s, 1H), 8,27 (d, J = 7.8, 1H), 8.06 (d, J = 7.7, 1H), 7.84 (t, J = 7.9, 1H), 7.62 (d, J = 7.6, 1H), 7.53 (t, J = 7.7, 1H), 6.17 (s, 2H), 4.86 (m, 1H), 3.98 (m, 1H), 3.26 (m, 2H), 3.07 (m, 2H), 2.15 (m, 2H). 1.91 (m, 2H)

| | | | |
|---|---|---|---|
| "A28" | | 518 | |
| "A29" | | 604 | |
| "A30" | hydrochloride | 504 | 2.57 (method A) |

¹H-NMR (500 MHz, DMSO-d₆) δ [ppm] 9.58 (s, 1H), 8.78 (m, 2H), 8.66 (d, J = 8.1, 1H), 8.65 (s, 2H), 8.54 (m, 1H), 8.48 (s, 1H), 8.26 (d, J = 7.8, 1H), 8.07 (d, J = 7.7, 1H), 7.84 (t, J = 7.9, 1H), 7.60 (d, J = 7.7, 1H), 7.51 (t, J = 7.7, 1H), 6.17 (s, 2H), 4.12 (d, J = 6.3, 2H), 3.26 (m, 2H), 2.68 (m, 2H), 1.89 (m, 2H), 1.57-1.18 (m, 2H)

-continued
| Compound No. | Name and/or structure | LCMS [M + H] | HPLC Rt. in min |
|---|---|---|---|
| "A31" | 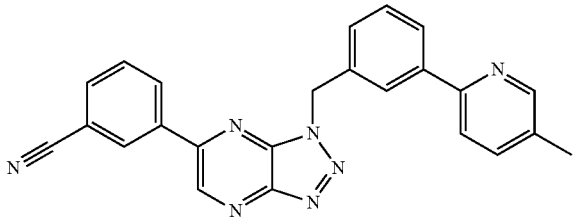 | 404 | |
| "A32" | 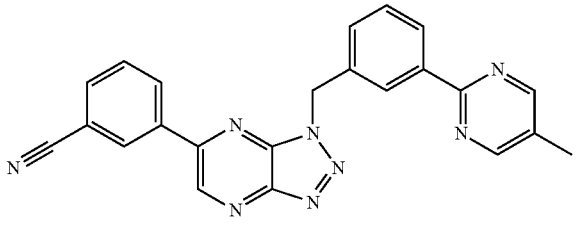 | 405 | |
| "A33" | 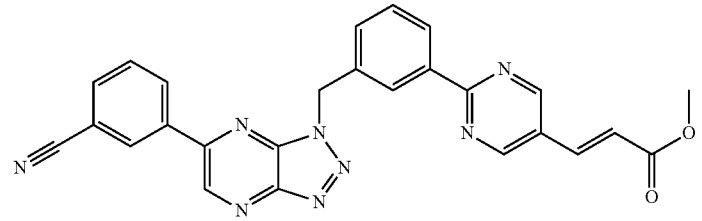 [SMILES: COC(=O)/C=C/c1cnc(-c2cccc(Cn3nnc4ncc(-c5cccc(C#N)c5)nc43)c2)nc1] | 475 | |
| "A34" | 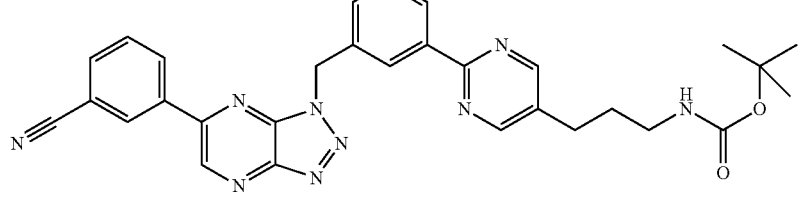 | 548 | |
| "A35" | 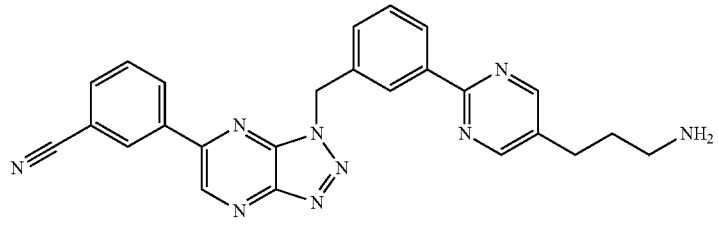 [SMILES: N#Cc1cccc(-c2cnc3nnn(Cc4cccc(-c5ncc(CCCN)cn5)c4)c3n2)c1] | 448 | |
| "A36" | 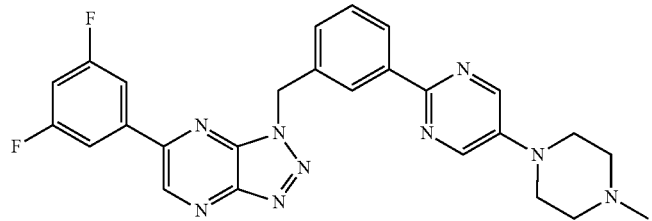 [SMILES: CN1CCN(c2cnc(-c3cccc(Cn4nnc5ncc(-c6cc(F)cc(F)c6)nc54)c3)nc2)CC1] | 500 | |

| Compound No. | Name and/or structure | LCMS [M + H] | HPLC Rt. in min |
|---|---|---|---|
| "A37" | 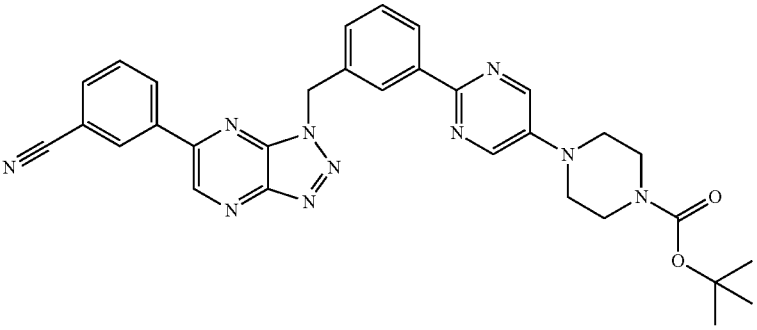 [SMILES: CC(C)(C)OC(=O)N1CCN(c2cnc(-c3cccc(Cn4nnc5ncc(-c6cccc(C#N)c6)nc54)c3)nc2)CC1] | 575 | |
| "A38" | 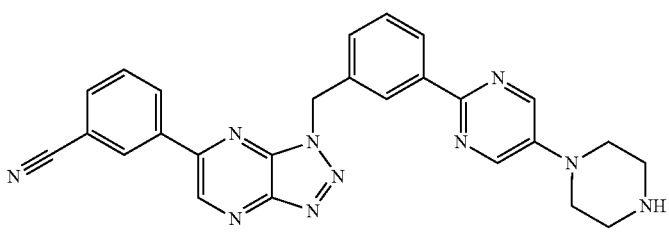 [SMILES: N#Cc1cccc(-c2cnc3nnn(Cc4cccc(-c5ncc(N6CCNCC6)cn5)c4)c3n2)c1] | 475 | |
| "A39" | 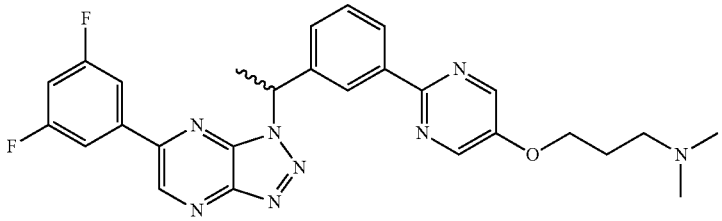 [SMILES: CC(c1cccc(-c2ncc(OCCCN(C)C)cn2)c1)n1nnc2ncc(-c3cc(F)cc(F)c3)nc21] | 517 | |
| "A40" | 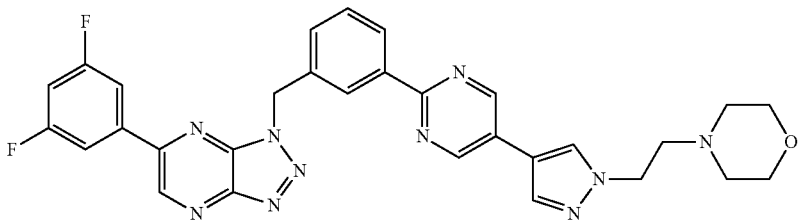 [SMILES: Fc1cc(F)cc(-c2cnc3nnn(Cc4cccc(-c5ncc(-c6cnn(CCN7CCOCC7)c6)cn5)c4)c3n2)c1] | 549 | |
| "A41" | 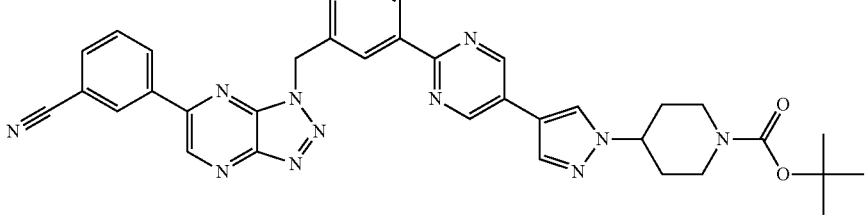 | 640 | |
| "A42" | 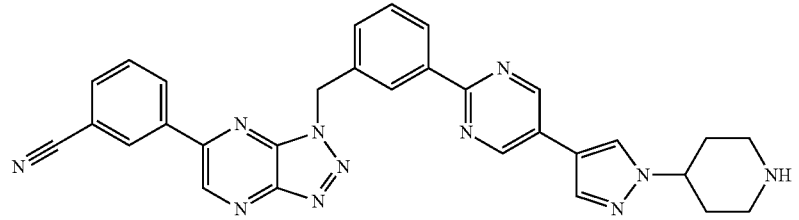 [SMILES: N#Cc1cccc(-c2cnc3nnn(Cc4cccc(-c5ncc(-c6cnn(C7CCNCC7)c6)cn5)c4)c3n2)c1] | 540 | |

| Compound No. | Name and/or structure | LCMS [M + H] | HPLC Rt. in min |
|---|---|---|---|
| "A43" | [structure: 5-(3,5-difluorophenyl)-3-[[3-[5-[1-(2-pyrrolidin-1-ylethyl)pyrazol-4-yl]pyrimidin-2-yl]phenyl]methyl]triazolo[4,5-b]pyrazine] | 565 | |
| "B15" | [structure with hydrochloride] | 444 | 2.50 (method A) |

¹H-NMR (500 MHz, DMSO-d₆) δ [ppm] 9.19 (s, 1H), 8.63 (s, 4H), 8.46 (s, 1H), 8.32 (s, 1H), 8.25 (d, J = 7.7, 1H), 7.54 (d, J = 7.7, 1H), 7.50 (t, J = 7.6, 1H), 6.03 (s, 2H), 4.25 (t, J = 6.3, 2H), 3.95 (s, 3H), 3.58 (t, J = 6.2, 2H), 1.91 (p, J = 6.3, 2H)

| "B16" | [structure with hydrochloride] | 444 | 2.66 (method A) |

¹H-NMR (500 MHz, DMSO-d₆) δ [ppm] 9.19 (s, 1H), 8.65 (s, 2H), 8.63 (s, 1H), 8.45 (s, 1H), 8.32 (s, 1H), 8.26 (d, J = 7.7, 1H), 7.55 (d, J = 7.7, 1H), 7.51 (t, J = 7.6, 1H), 6.04 (s, 2H), 4.32 (dd, J = 3.6, 5.3, 2H), 3.95 (s, 3H), 3.74-3.66 (m, 2H), 3.47 (s, 3H)

| "B17" | [structure with hydrochloride] | 512 | 2.12 (method A) |

¹H-NMR (500 MHz, DMSO-d₆) δ [ppm] 9.19 (s, 1H), 8.64 (s, 3H), 8.43 (s, 1H), 8.31 (s, 1H), 8.26 (d, J = 7.8, 1H), 7.56 (m, 1H), 7.51 (t, J = 7.7, 1H), 6.03 (s, 2H), 4.32 (m, 2H), 3.95 (s, 3H), 3.66-3.37 (m, 2H), 2.77 (s, 3H), 1.42 (m, 8H)

| "B18" | [structure] | 513 | 2.26 (method A) |

¹H-NMR (500 MHz, DMSO-d₆) δ [ppm] 9.19 (s, 1H), 8.63 (s, 3H), 8.46 (s, 1H), 8.32 (s, 1H), 8.25 (d, J = 7.7, 1H), 7.54 (d, J = 7.6, 1H), 7.50 (t, J = 7.6, 1H), 6.03 (s, 2H), 4.23 (t, J = 6.3, 2H), 3.95 (s, 3H); 3.61-3.47 (m, 4H), 2.65-2.29 (m, 6H), 1.92 (m, 2H)

| Compound No. | Name and/or structure | LCMS [M + H] | HPLC Rt. in min |
|---|---|---|---|
| "B19" | (structure) | 526 | 2.16 (method A) |

¹H-NMR (500 MHz, DMSO-d₆) δ [ppm] 9.19 (s, 1H), 8.64 (s, 2H), 8.63 (s, 1H), 8.45 (s, 1H), 8.31 (s, 1H), 8.25 (d, J = 7.6, 1H), 7.54 (d, J = 7.7, 1H), 7.50 (t, J = 7.6, 1H), 6.04 (s, 2H), 4.32 (t, J = 5.4, 2H), 3.95 (s, 3H), 3.56-3.29 (m, 6H), 2.81 (s, 3H), 2.50 (dt, J = 1.8, 3.6, 2H)

| "B20" | (structure) hydrochloride | 485 | 2.23 (method A) |

¹H-NMR (500 MHz, DMSO-d₆) δ [ppm] 9.30 (s, 1H), 9.19, s, 1H), 8.66 (s, 2H), 8.63 (s, 1H), 8.44 (s, 1H), 8.32 (s, 1H), 8.26 (d, J = 7.7, 1H), 7.56 (d, J = 7.7, 1H), 7.51 (t, J = 7.7, 1H), 6.04 (s, 2H), 5.57 (s, 1H), 4.30 (dd, J = 4.5, 10.1, 2H), 4.12 (m, 1H), 3.95 (s, 3H), 3.41-2.38 (m, 6H)

| "B21" | (structure) hydrochloride | 554 | 2.64 (method A) |

¹H-NMR (500 MHz, DMSO-d₆) δ [ppm] 9.59 (s, 1H), 9.16 (s, 2H), 8.80 (s, 1H), 8.67 (d, J = 8.1, 1H), 8.62 (s, 1H), 8.49 (s, 1H), 8.36 (d, J = 7.8, 1H), 8.23 (s, 1H), 8.08 (d, J = 7.7, 1H); 7.84 (t, J = 7.9, 1H), 7.65 (t, J = 8.1, 1H), 7.62 (d, J = 4.8, 1H), 6.20 (s, 2H), 4.58 (t, J = 6.1, 2H), 3.70 (t, 2H), 3.55 (m, 2H), 3.06 (m, 2H), 2.01 (m, 2H), 1.85 (m, 2H)

| "B22" | (structure) hydrochloride | 519 | 2.30 (method A) |

¹H-NMR (500 MHz, DMSO-d₆) δ [ppm] 9.58 (s, 1H), 8.79 (s, 1H), 8.66 (d, J = 10.0, 1H), 8.64 (s, 2H), 8.53 (s, 1H), 8.27 (d, J = 7.9, 1H), 8.07 (d, J = 7.8, 1H), 7.84 (t, J = 7.9, 1H), 7.61 (d, J = 7.7, 1H), 7.52 (t, J = 7.7, 1H), 6.17 (s, 2H), 4.34 (m, 2H), 3.82 (s, 1H), 3.13 (m, 2H), 2.97-2.85 (m, 4H), 2.73-2.54 (m, 4H)

| Compound No. | Name and/or structure | LCMS [M + H] | HPLC Rt. in min |
|---|---|---|---|
| "B23" | (structure) hydrochloride | 530 | 2.45 (method A) |

¹H-NMR (500 MHz, DMSO-d$_6$) δ [ppm] 9.56 (s, 1H), 9.32 (m, 1H), 8.69 (s, 2H), 8.58 (s, 1H), 8.28 (d, J = 7.9, 1H), 8.10 (m, 2H), 7.62 (d, J = 7.7, 1H), 7.52 (m, 2H), 6.17 (s, 2H), 4.59 (m, 2H), 3.74 (m, 9H), 3.42 (m, 2H)

| | | | |
|---|---|---|---|
| "B24" | (structure) hydrochloride | 515 | 2.73 (method A) |

¹H-NMR (500 MHz, DMSO-d$_6$) δ [ppm] 9.56 (s, 1H), 8.76 (m, 1H), 8.63 (s, 2H), 8.57 (s, 1H), 8.45 (m, 1H), 8.27 (d, J = 7.9, 1H), 8.20 (d, J = 6.6, 2H), 7.61 (d, J = 7.7, 1H), 7.55-7.46 (m, 2H), 6.16 (s, 2H), 4.10 (d, J = 6.3, 2H), 3.30 (m, 2H), 2.91 (m, 2H), 2.12 (m, 1H), 1.93 (m, 2H), 1.50 (m, 2H)

| | | | |
|---|---|---|---|
| "B25" | (structure) hydrochloride | 531 | |
| "B26" | (structure) hydrochloride | 520 | |
| "B27" | (structure) hydrochloride | 506 | |

-continued

| Compound No. | Name and/or structure | LCMS [M + H] | HPLC Rt. in min |
|---|---|---|---|
| "B28" | | 514 | |
| "B29" | hydrochloride | 515 | |
| "B30" | hydrochloride | 520 | |
| "B31" | hydrochloride | 529 | |
| "B32" | | 491 | |
| "B33" | | 543 | 2.08 (method C) |

$^1$H-NMR (500 MHz, DMSO-d$_6$) δ [ppm] 9.21 (s, 1H), 8.67-8.61 (m, 3H), 8.46 (b, 1H), 8.35 (s, 1H), 8.25 (d, J = 7.6, 1H), 7.47-7.57 (m, 2H), 6.04 (s, 2H), 4.37 (t, J = 5.2, 2H), 4.28 (t, 2H), 3.72 (t, 2H), 3.60-3.53 (m, 4H), 3.23 (s, 3H), 2.73 (t, J = 5.6, 2H), 2.49-2.41 (m, 4H)

| Compound No. | Name and/or structure | LCMS [M + H] | HPLC Rt. in min |
|---|---|---|---|
| "B34" | 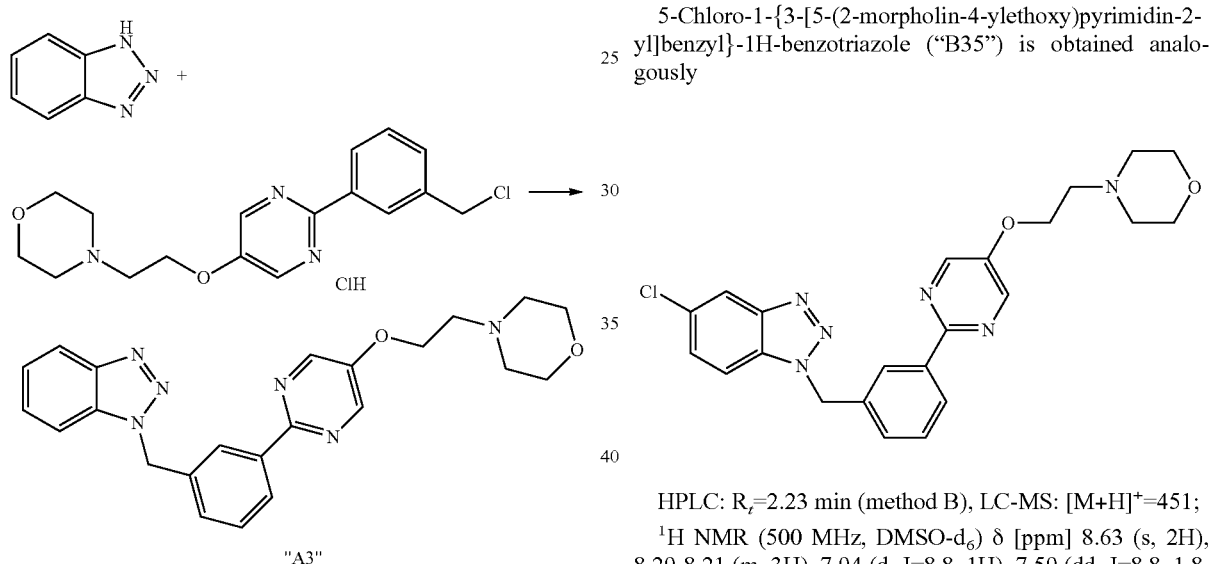 ¹H-NMR (500 MHz, DMSO-d₆) δ [ppm] 9.22 (s, 1H), 8.69-8.60 (m, 3H), 8.46 (s, 1H), 8.35 (s, 1H), 8.29-8.22 (m, 1H), 7.47-7.57 (m, 2H), 6.04 (s, 2H), 4.98 (t, J = 5.3, 1H), 4.30 (t, J = 5.6, 2H), 4.25 (t, J = 5.4, 2H), 3.79 (q, J = 5.4, 2H), 3.62-3.52 (m, 4H), 2.73 (t, J = 5.6, 2H), 2.40-2.50 (m, 4H) | 529 | 1.94 (method C) |

Preparation of 1-{3-[5-(2-morpholin-4-ylethoxy)pyrimidin-2-yl]benzyl}-1H-benzotriazole ("A3")

49 mg (0.41 mmol) of 1H-benzotriazole, 150 mg (0.41 mmol) of 4-{2-[2-(3-chloromethylphenyl)pyrimidin-5-yloxy]ethyl}morpholine hydrochloride and 136 mg (1.62 mmol) of sodium hydrogencarbonate are suspended in 4 ml of acetonitrile and stirred at 90° C. for 18. Water is added to the reaction mixture, which is then extracted with ethyl acetate. The organic phase is dried over sodium sulfate, evaporated and purified by means of column chromatography on silica gel.

Yield: 14 mg; Rt.=2.27 min; LCMS: 417 (M+H);

¹H-NMR (500 MHz, DMSO-d₆) δ [ppm] 8.63 (s, 2H), 8.27 (b, 1H), 8.23 (td, 1H), 8.06 (d, 1H), 7.86 (d, 1H), 7.38-7.56 (m, 4H), 6.09 (s, 2H), 4.29 (2, 1H), 3.57 (t, 4H), 2.72 (t, 2H), 2.45-2.49 (b, 4 H).

5-Chloro-1-{3-[5-(2-morpholin-4-ylethoxy)pyrimidin-2-yl]benzyl}-1H-benzotriazole ("B35") is obtained analogously HPLC: R$_t$=2.23 min (method B), LC-MS: [M+H]⁺=451;

¹H NMR (500 MHz, DMSO-d₆) δ [ppm] 8.63 (s, 2H), 8.29-8.21 (m, 3H), 7.94 (d, J=8.8, 1H), 7.59 (dd, J=8.8, 1.8, 1H), 7.53-7.37 (m, 2H), 6.09 (d, J=12.7, 2H), 4.30 (t, J=5.6, 2H), 3.61-3.55 (m, 4H), 2.72 (t, J=5.6, 2H), 2.49-2.41 (m, 4H).

Preparation of 5-chloro-3-{3-[5-(2-morpholin-4-ylethoxy)pyrimidin-2-yl]-benzyl}-3H-1,2,3-triazolo[4,5-b]pyridine ("A48")

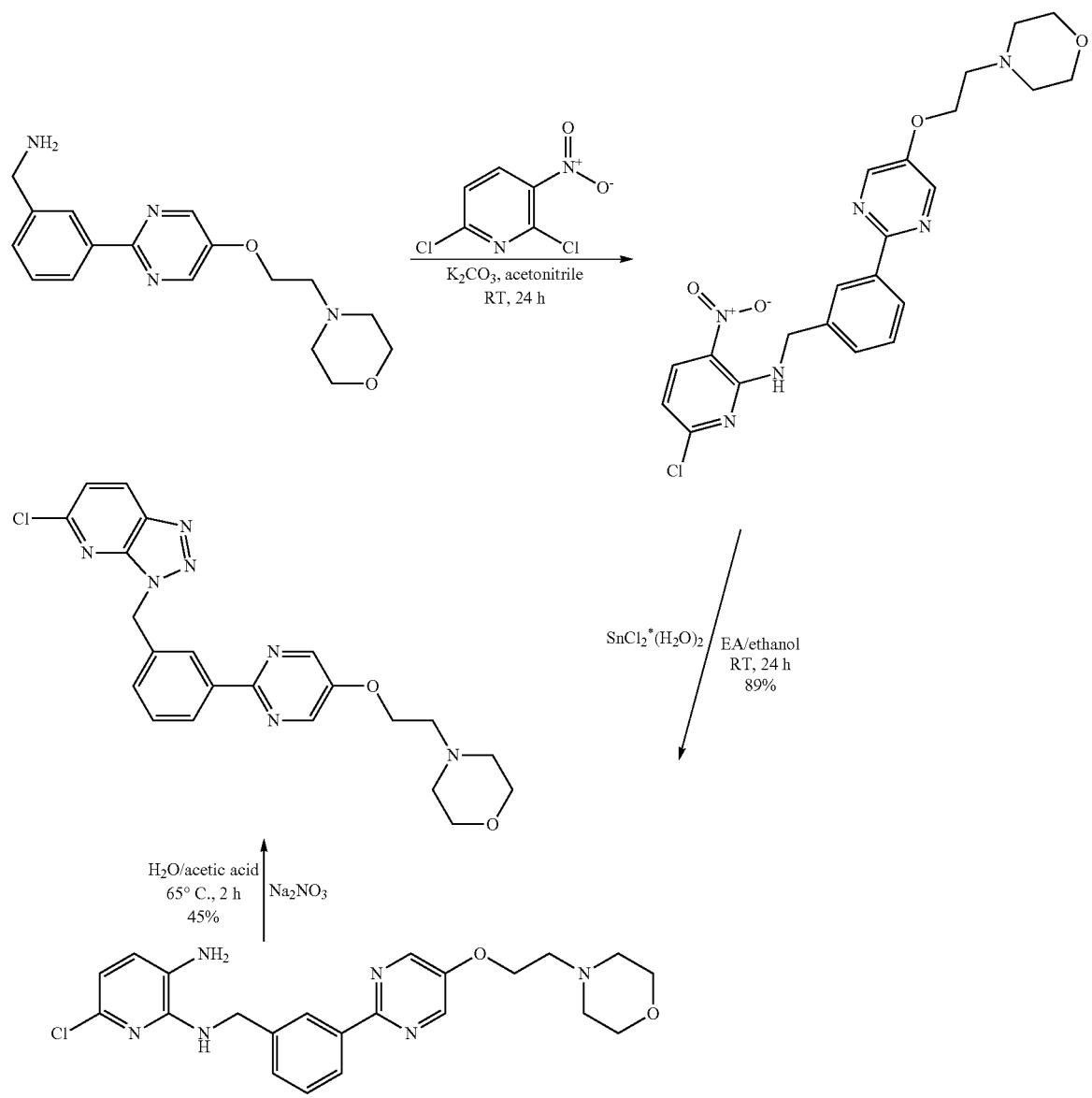

Step 1:

87.8 mg (0.442 mmol) of 2,6-dichloro-3-nitropyridine is dissolved in 3 ml of acetonitrile, and 144 mg (0.442 mmol) of potassium carbonate are added. The mixture is subsequently cooled to 0° C., and a solution of 200 mg (0.442 mmol) of 3-[5-(2-morpholin-4-ylethoxy)pyrimidin-2-yl]benzylamine in 3 ml of acetonitrile is added dropwise. The reaction mixture is stirred at RT for 3.5 h. Water and ethyl acetate are subsequently added to the reaction mixture. The organic phase is dried over sodium sulfate, evaporated under reduced pressure and purified by column chromatography on silica gel.

Yield: 115 mg, HPLC: $R_t$=2.50 min (method B), LC-MS: [M+H]$^+$=471.

Step 2:

115 mg (0.244 mmol) of (6-chloro-3-nitropyridin-2-yl)-{3-[5-(2-morpholin-4-ylethoxy)pyrimidin-2-yl]benzyl}amine are dissolved in 7 ml of ethyl acetate and 3 ml of ethanol. 275 mg (1.22 mmol) of tin(II) chloride dihydrate are added, and the reaction mixture is stirred at 55° C. for 24 h. The reaction mixture is adjusted to pH 7 using 32% NaOH. The resultant precipitate is filtered off through Celite with suction and washed with EA. The filtrate is extracted. The organic phase is subsequently washed with water, dried over sodium sulfate and evaporated under reduced pressure.

Yield: 95.5 mg, HPLC: $R_t$=2.22 min (method C), LC-MS: [M+H]$^+$=441.

Step 3:

95.5 mg (0.217 mmol) of 6-chloro-N'2'-{3-[5-(2-morpholin-4-ylethoxy)pyrimidin-2-yl]benzyl}pyridine-2,3-diamine are dissolved in 2.4 ml of water and 2.4 ml of acetic acid. A solution of 149.4 mg (2.166 mmol) of sodium nitrite in 2.4 ml of water is added and stirred at RT for 1 h. The solution is subsequently stirred at 65° C. for 4 h. The reaction mixture is neutralised using NaOH, and ethyl acetate and water are added. The organic phase is separated off, the aqueous phase is extracted with ethyl acetate, and the combined organic phases are dried over sodium sulfate. The solvent is evaporated under reduced pressure and purified by column chromatography on silica gel.

Yield: 45 mg, HPLC: $R_t$=2.18 min (method C), LC-MS: [M+H]$^+$=452;

$^1$H-NMR (500 MHz, DMSO-d$_6$) δ [ppm] 8.67 (d, J=8.6, 1H), 8.64 (s, 2H), 8.31 (s, 1H), 8.26 (d, 1H), 7.61 (d, J=8.6, 1H), 7.50 (t, J=7.6, 1H), 7.45 (d, J=7.7, 1H), 6.02 (s, 2H), 4.30 (t, J=5.6, 2H), 3.59-3.54 (m, 4H), 2.73 (t, J=5.6, 2H), 2.49 (ddd, J=3.1, 6.2, 12.6, 4H).

Preparation of (5-bromo-2-nitrophenyl)-{3-[5-(2-morpholin-4-ylethoxy)-pyrimidin-2-yl]benzyl}amine ("B36")

column chromatography on silica gel; yield: 1.29 g, HPLC: $R_t$=2.61 min (method B), LC-MS: [M+H]$^+$=514/516.

Step 2:

763 mg (1.35 mmol) of (5-bromo-2-nitrophenyl)-{3-[5-(2-morpholin-4-ylethoxy)-pyrimidin-2-yl]benzyl}amine are dissolved in 14 ml of ethyl acetate and 6 ml of ethanol. 1.53 g (6.75 mmol) of tin(II) chloride dihydrate are added, and the reaction mixture is stirred at 55° C. for 24 h. The reaction mixture is adjusted to pH 7 using 32% NaOH. The resultant precipitate is filtered off through Celite with suction and washed with EA. The filtrate is extracted. The organic phase

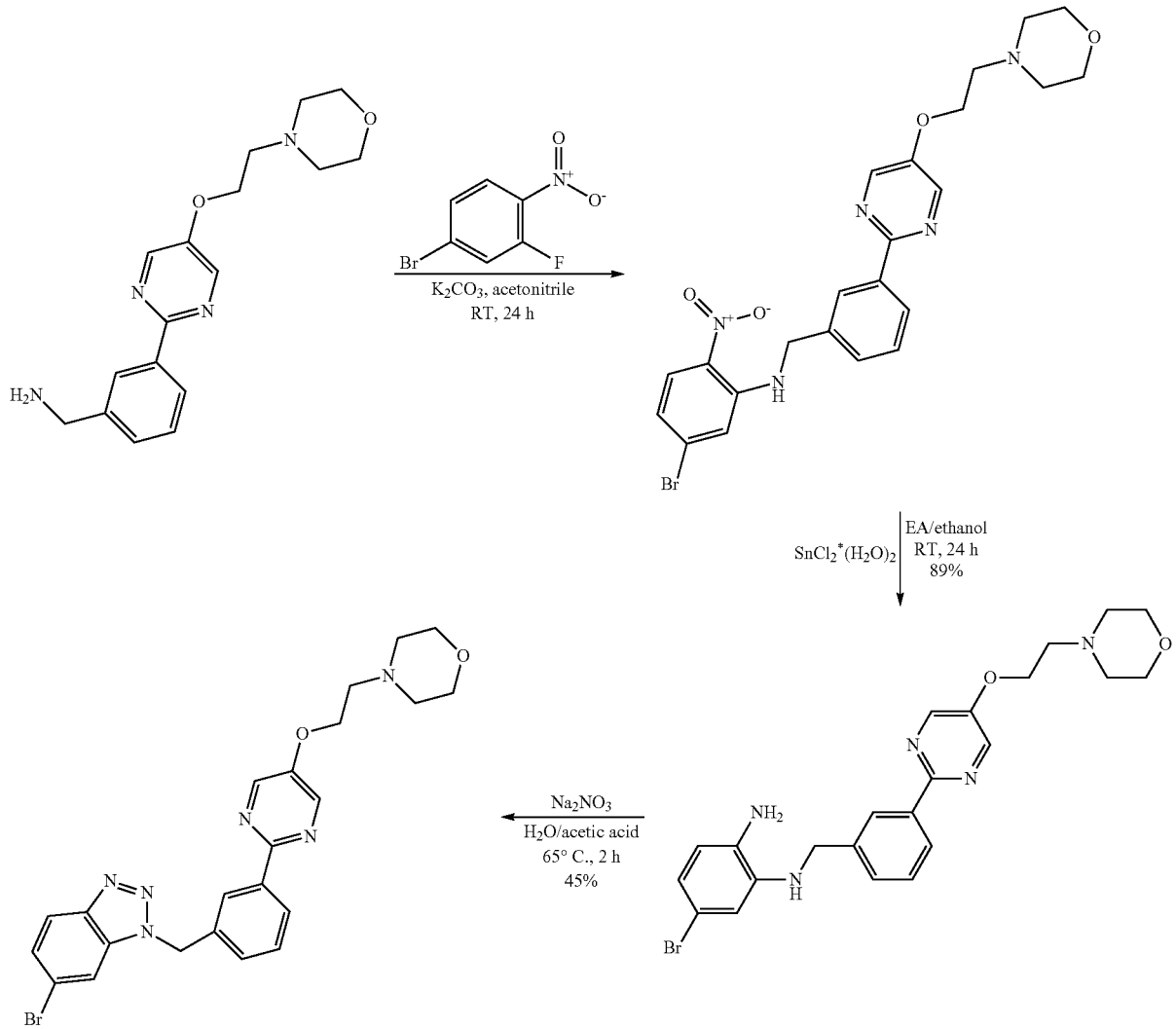

is subsequently washed with water, dried over sodium sulfate and evaporated under reduced pressure;

yield: 617 mg, HPLC: $R_t$=2.28 min (method C), LC-MS: [M+H]$^+$=484/486.

Step 3:

617 mg (1.11 mmol) of 4-bromo-N'-2'-{3-[5-(2-morpholin-4-ylethoxy)-pyrimidin-2-yl]benzyl}benzene-1,2-diamine are dissolved in 7.2 ml of water and 7.2 ml of acetic acid. A solution of 776 mg (11.1 mmol) of sodium nitrite in 7.2 ml of water is added and stirred at RT for 1 h. The solution is subsequently stirred at 65° C. for 4 h. The reaction mixture is neutralised using NaOH, and ethyl acetate and water are Step 1:

496 mg (0.208 mmol) of 4-bromo-2-fluoro-1-nitrobenzene is dissolved in 10 ml of acetonitrile, and 0.305 g (0.208 mmol) of potassium carbonate is added. The mixture is subsequently cooled to 0° C., and a solution of 1.00 g (0.208 mmol) of 3-[5-morpholin-4-ylethoxy)pyrimidin-2-yl]benzylamine in 10 ml of acetonitrile is added dropwise. The reaction mixture is stirred at RT for 3.5 h.

Water and ethyl acetate are subsequently added to the reaction mixture. The organic phase is dried over sodium sulfate, evaporated under reduced pressure and purified by added. The organic phase is separated off, the aqueous phase is extracted with ethyl acetate, and the combined organic phases are dried over sodium sulfate. The solvent is evaporated under reduced pressure and purified by column chromatography on silica gel; yield: 484 mg, HPLC: $R_t$=2.27 min (method C), LC-MS: [M+H]$^+$=495/497.

Preparation of 6-(1-methyl-1H-pyrazol-4-yl)-1-{3-[5-(2-morpholin-4-yl-ethoxy)pyrimidin-2-yl]benzyl}-1H-benzotriazole ("A50")

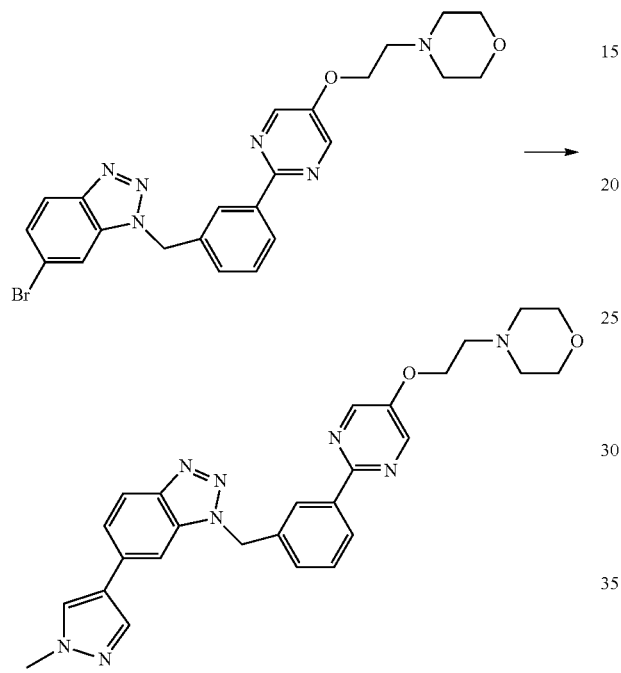

200 mg (0.352 mmol) of 6-bromo-1-{3-[5-(2-morpholin-4-ylethoxy)pyrimidin-2-yl]benzyl}-1H-benzotriazole, 80.6 mg (0.387 mmol) of 1-methyl-4-(4,4,5,5-tetramethyl-1,3,2-dioxaborolan-2-yl)-1H-pyrazole and 150 mg (0.704 mmol) of tripotassium phosphate trihydrate are suspended in 6 ml of ethylene glycol dimethyl ether, degassed evacuated and flushed with nitrogen a number of times. 24.7 mg (0.035 mmol) of bis(triphenylphosphine)palladium(II) chloride are added, and the mixture is again evacuated and flushed with nitrogen. The reaction mixture is stirred at 80° C. for 24 h. Water is added to the reaction mixture, which is then rendered basic using 32% NaOH and extracted with DCM. The organic phase is dried over sodium sulfate, evaporated under reduced pressure in a rotary evaporator and purified by column chromatography on silica gel; yield: 41 mg, HPLC: $R_t$=2.08 min (method C), LC-MS: [M+H]$^+$=497;

$^1$H-NMR (500 MHz, DMSO-d$_6$) δ [ppm] 8.63 (s, 2H), 8.29 (s, 1H), 8.26-8.20 (m, 2H), 8.10 (s, 1H), 8.02 (d, J=8.7, 1H), 7.96 (s, 1H), 7.63 (dd, J=1.4, 8.7, 1H), 7.49 (dd, J=1.7, 4.9, 2H), 6.05 (s, 2H), 4.29 (t, J=5.6, 2H), 3.88 (s, 3H), 3.61-3.51 (m, 4H), 2.72 (t, J=5.6, 2H), 2.53-2.44 (m, 4H).

Preparation of 3-{3-[5-(2-morpholin-4-ylethoxy)pyrimidin-2-yl]benzyl}-3H-1,2,3-triazolo[4,5-b]pyridines ("A44")

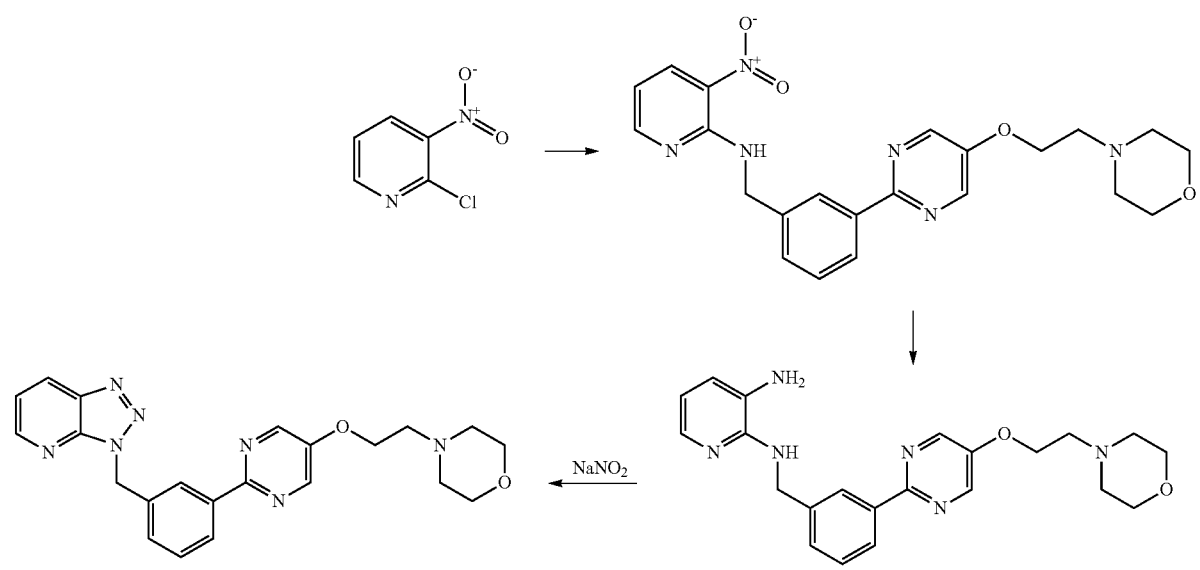

"A44"

The following compounds are prepared analogously

| Compound No. | Name and/or structure | LCMS [M + H] | HPLC Rt. in min |
|---|---|---|---|
| "A45" | | 435 | |
| "A46" | | 453 | 2.21 (method C) |
| | ¹H-NMR (500 MHz, DMSO-d₆) δ [ppm] 8.63 (s, 2H), 8.25 (d, J = 9.2 2H), 7.98 (m, 1H), 7.55-7.47 (m, 2H), 7.38 (d, J = 7.5 1H), 6.10 (s, 2H), 3.61-3.54 (m, 2H), 3.28 (m, 4H), 2.72 (t, J = 5.6, 2H), 2.50 (m, 4H) | | |
| "A47" | | 432 | |
| "A48" | | 452 | |
| "A49" | | 413/415 | |
| "A50" | | 469 | |

| Compound No. | Name and/or structure | LCMS [M + H] | HPLC Rt. in min |
|---|---|---|---|
| "B37" | (structure) | 420 | 2.43 (method A) |
$^1$H-NMR (500 MHz, DMSO-d$_6$) δ [ppm] 9.45 (s, 1H) 8.64 (s, 2H), 8.44 (s, 1H), 8.39 (d, J = 8.9, 1H), 8.25 (d, J = 7.7, 1H), 7.55 (d, J = 7.8, 1H), 7.50 (t, J = 7.6, 1H), 6.93 (d, J = 8.9, 1H), 5.91 (s, 2H), 4.28 (t, J = 5.9, 2H), 4.04 (s, 3H), 3.30 (m, 2H), 2.82 (s, 6H), 2.20-2.15 (m, 2H)
Preparation of 5-(1-methyl-1H-pyrazol-4-yl)-3-{3-[5-(2-morpholin-4-ylethoxy)-pyrimidin-2-yl]benzyl}-3H-1,2,3-triazolo[4,5-d]pyrimidine ("A51")
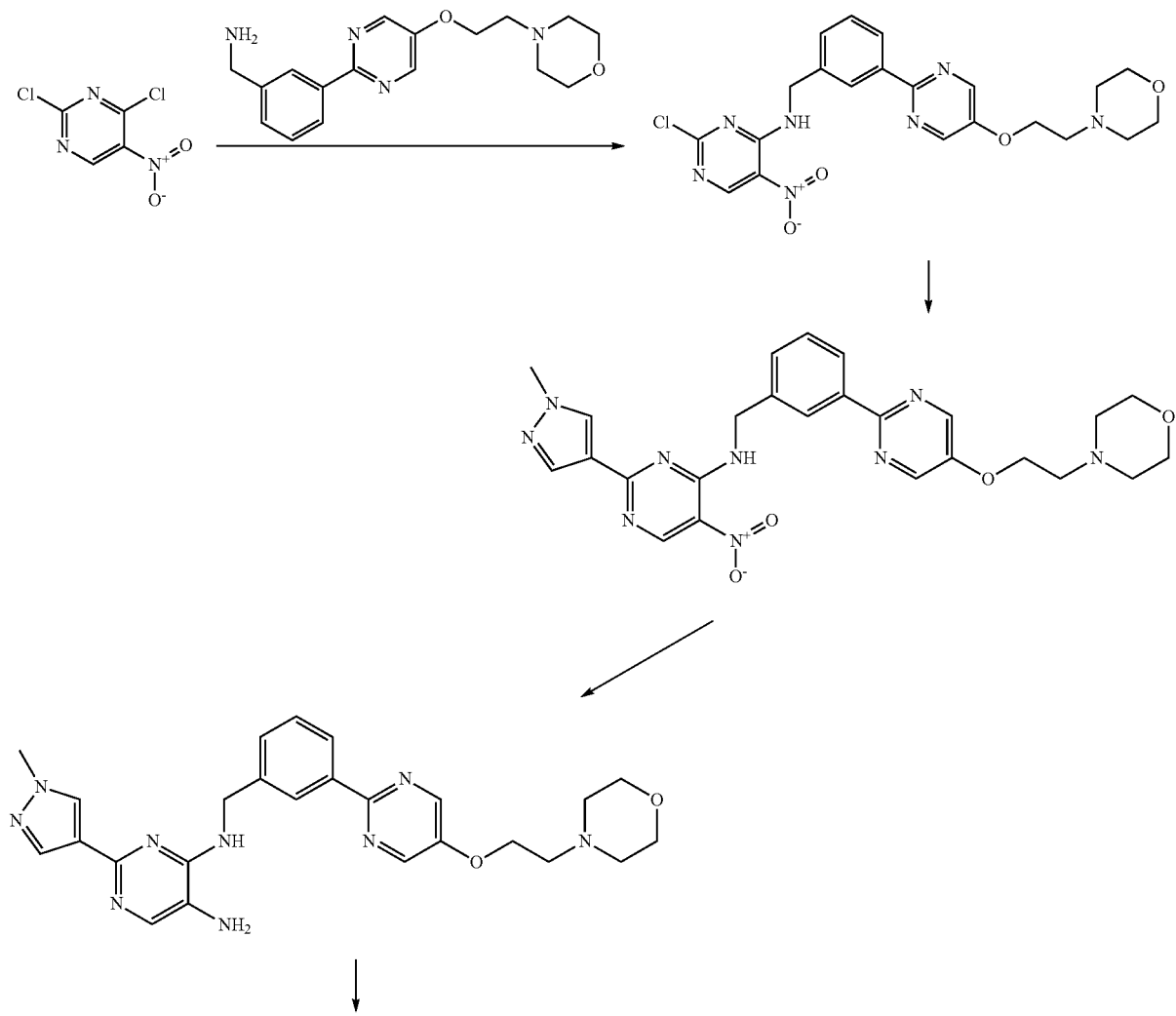

-continued
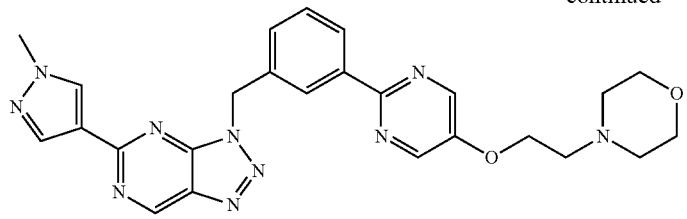
"A51"
The following compounds are obtained analogously:
| Compound No | Name and/or structure | LCMS [M + H] | Rt. in min |
|---|---|---|---|
| "A52" | | 503 | |
| "A53" | | 468 | |
| "A54" | | 471 | |
Preparation of 1-{3-[5-(2-morpholin-4-ylethoxy)pyrimidin-2-yl]benzyl}-6-(propane-1-sulfonyl)-1H-benzotriazole ("A55")
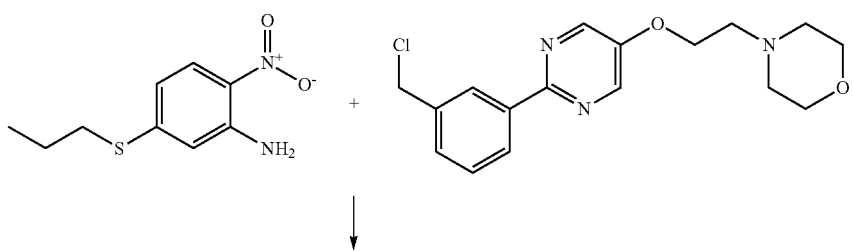

-continued

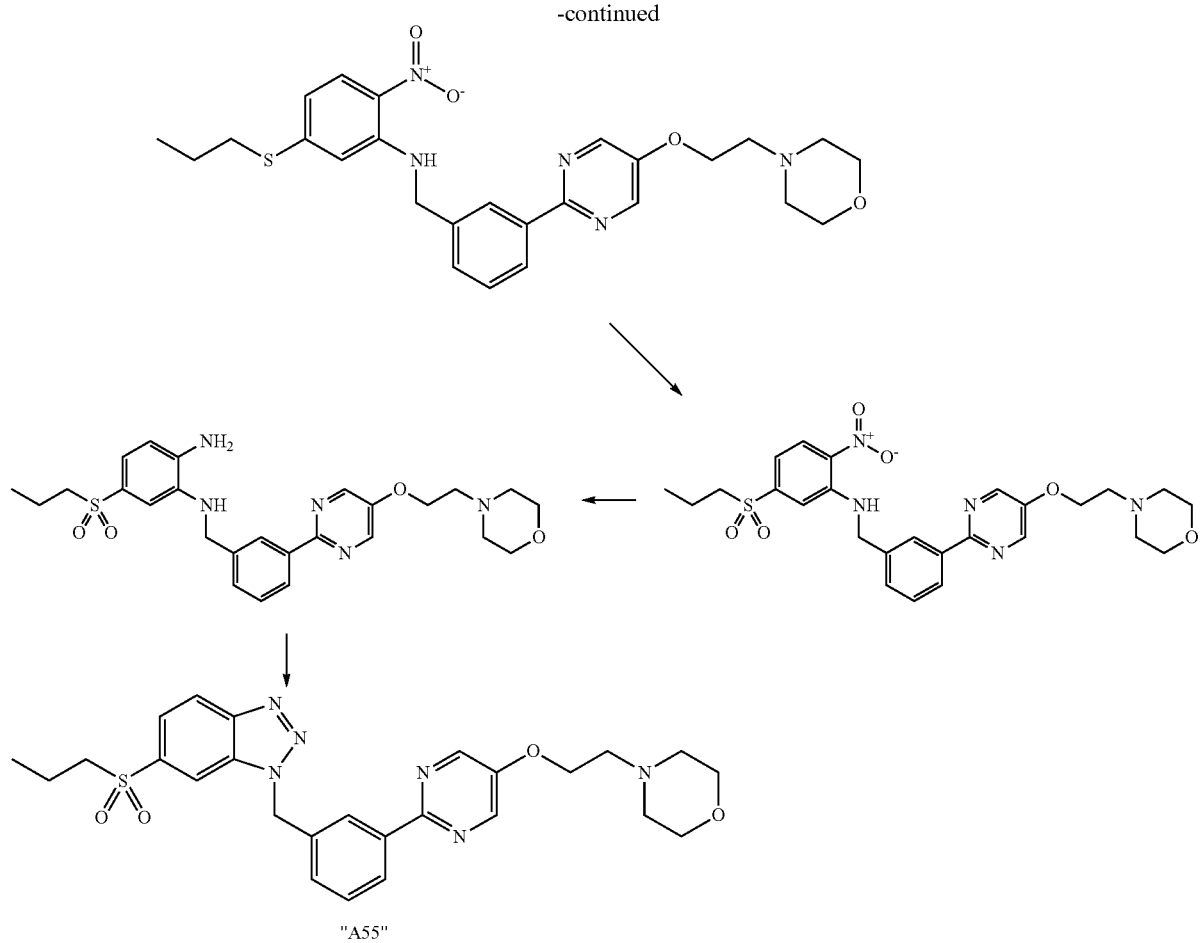

"A55"

Pharmacological Data

TABLE 1

Met kinase inhibition

| Compound No. | Biochemical assay IC$_{50}$ (enzyme) | Cellular assay IC$_{50}$ (cell) |
| --- | --- | --- |
| "A1" |  | A |
| "A2" | A | A |
| "A3" | A | B |
| "A6" | A | A |
| "A9" | A | A |
| "A24" | A | A |
| "A27" | A | A |
| "A30" | A | A |
| "A46" | A | A |
| "A48" | A | B |
| "A50" | A | A |
| "B1" | A | B |
| "B5" | A | A |
| "B6" | A | A |
| "B7" | A | A |
| "B9" | A | A |
| "B10" | A | A |
| "B14" | A | A |
| "B15" | A | A |
| "B16" | A | A |
| "B17" | A | A |
| "B18" | A | A |
| "B19" | A | A |
| "B20" | A | A |
| "B21" | A | A |
| "B22" | A | A |
| "B23" | A | A |
| "B24" | A | A |
| "B33" | A | A |
| "B34" | A | A |
| "B35" | B | C |
| "B36" | A | B |
| "B37" | A | A |

IC$_{50}$: 1 nM-0.1 μM = A
0.1 μM-10 μM = B
>10 μM = C

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

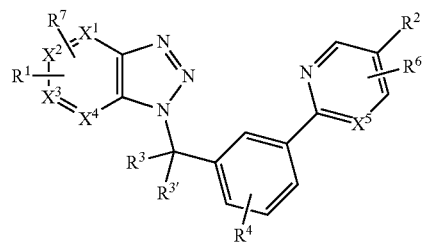

in which
$X^1$, $X^2$, $X^3$, $X^4$, $X^5$ each, independently of one another, denote CH or N,
$R^1$, $R^2$, $R^7$ each, independently of one another, denote H, Hal, A, $[C(R^5)_2]_n OR^5$, $N\!=\!CR^5 N(R^5)_2$, $SR^5$, $NO_2$, CN, $[C(R^5)_2]_n COOR^5$, $CON(R^5)_2$, $NR^5 COA$, $NR^5 SO_2 A$, $SO_2 N(R^5)_2$, $S(O)_m A$, $[C(R^5)_2]_n N(R^5)_2$, $[C(R^5)_2]_n Het$, $O[C(R^5)_2]_p OR^5$, $O[C(R^5)_2]_p N(R^5)_2$, $O[C(R^5)_2]_p N^+O^{3\,1}(R^5)_2$, $O[C(R^5)_2]_n Het$, $S[C(R^5)_2]_p N(R^5)_2$, $S[C(R^5)_2]_p Het$, $NR^5[C(R^5)_2]_n N(R^5)_2$, $NR^5[C(R^5)_2]_n Het$, $NHCON(R^5)_2$, $NHCONH[C(R^5)_2]_p N(R^5)_2$, $NHCONH[C(R^5)_2]_n Het$, $NHCO[C(R^5)_2]_n N(R^5)_2$, $NHCO[C(R^5)_2]_n Het$, $[C(R^5)_2]_n CON(R^5)_2$, $CONR^5[C(R^5)_2]_n N(R^5)_2$, $CONR^5[C(R^5)_2]_n NR^5 COOA$, $[C(R^5)_2]_n NR^5 COOA$, $CONR^5[C(R^5)_2]_n OR^5$, $CONR^5[C(R^5)_2]_n Het$, $COHet$, $COA$, $CH\!=\!CH\!-\!COOR^5$, $CH\!=\!CH\!-\!N(R^5)_2$, $CH\!=\!CH\!-\!CON(R^5)_2$, $O\!-\![C(R^5)_2]_n$-cycloalkylene-$[C(R^5)_2]_n$-Het, $O\!-\![C(R^5)_2]_n$-cycloalkylene-$[C(R^5)_2]_n N(R^5)_2$, $O\!-\![C(R^5)_2]_n$-cycloalkylene-$[C(R^5)_2]_n\!-\!OR^5$, $[C(R^5)_2]_n Ar$, $O[C(R^5)_2]_n Ar$, $S[C(R^5)_2]_n Ar$, $NR^5[C(R^5)_2]_n Ar$, $NHCONH[C(R^5)_2]_n Ar$, $NHCO[C(R^5)_2]_n Ar$, $CONR^5[C(R^5)_2]_n Ar$ or $COAr$,
$R^3$, $R^{3'}$ each, independently of one another, denote H, F or $R^8$, or
$R^3$ and $R^{3'}$ together denote an alkylene chain having 2-5 C atoms, in which 1 or 2 non-adjacent $CH_2$ groups are optionally replaced by O, NH and/or $NR^5$,
$R^4$, $R^6$ each, independently of one another, denote H, A or Hal,
$R^5$ denotes H or $R^8$,
$R^8$ denotes unbranched or branched alkyl having 1-6 C atoms,
A denotes unbranched or branched alkyl having 1-10 C atoms, in which 1-7 H atoms are optionally replaced by OH, F, Cl and/or Br, and/or in which one or two $CH_2$ groups are optionally replaced by O, $NR^8$, NH, S, SO, $SO_2$ and/or $CH\!=\!CH$ groups, or cyclic alkyl having 3-7 C atoms, which is optionally monosubstituted by OH,
Ar denotes phenyl, naphthyl or biphenyl, each of which is un-substituted or mono-, di- or trisubstituted by Hal, A, $OR^5$, $N(R^5)_2$, $SR^5$, $NO_2$, CN, $COOR^5$, $CON(R^5)_2$, $NR^5 COA$, $NR^5 SO_2 A$, $SO_2 N(R^5)_2$ and/or $S(O)_m A$,
Het denotes a mono-, bi- or tricyclic saturated, unsaturated or aromatic heterocycle having 1 to 4 N, O and/or S atoms, which is unsubstituted or mono-, di- or trisubstituted by Hal, A, $OR^5$, $N(R^5)_2$, $SR^5$, $NO_2$, CN, $COOR^5$, $CON(R^5)_2$, $NR^5 COA$, $NR^5 SO_2 A$, $SO_2 N(R^5)_2$, $S(O)_m A$, CO—$Het^1$, $Het^1$, $[C(R^5)_2]_n N(R^5)_2$, $[C(R^5)_2]_n OR^5$, $[C(R^5)_2]_n Het^1$, $O[C(R^5)_2]_n N(R^5)_2$, $O[C(R^5)_2]_p OR^5$, $O[C(R^5)_2]_n Het^1$, NHCOOA, $NHCON(R^5)_2$, NHCOO$[C(R^5)_2]_p N(R^5)_2$, NHCOO$[C(R^5)_2]_n Het$, NHCONH$[C(R^5)_2]_n N(R^5)_2$, NHCONH$[C(R^5)_2]_n Het^1$, OCONH[C $(R^5)_2]_nN(R^5)_2$, OCONH$[C(R^5)_2]_n$Het$^1$, CO—Het$^1$, CHO, COA, =S, =NH, =NA and/or =O, Het$^1$ denotes a monocyclic saturated heterocycle having 1 to 2 N and/or O atoms, which is optionally mono- or disubstituted by A, COOA, OA, OH, Hal and/or =O, Hal denotes F, Cl, Br or I, m denotes 0, 1 or 2, n denotes 0, 1, 2, 3 or 4, and p denotes 1, 2, 3 or 4, or a pharmaceutically acceptable salt, tautomer or stereoisomer thereof.

2. A compound according to claim 1, in which

R$^1$ denotes H, Hal, A, S(O)$_m$A, Ar, Het, O[C(R$^5$)$_2$]$_n$Ar, O[C(R$^5$)$_2$]$_n$Het or OR$^5$, or a pharmaceutically acceptable salt, tautomer or stereoisomer thereof.

3. A compound according to claim 1, in which

R$^7$ denotes H or Hal, or a pharmaceutically acceptable salt, tautomer or stereoisomer thereof.

4. A compound according to claim 1, in which

R$^2$ denotes A, Hal, [C(R$^5$)$_2$]$_n$N(R$^5$)$_2$, [C(R$^5$)$_2$]$_n$Het, O[C(R$^5$)$_2$]$_p$N(R$^5$)$_2$, O[C(R$^5$)$_2$]$_n$Het, [C(R$^5$)$_2$]$_n$OR$^5$, O[C(R$^5$)$_2$]$_p$OR$^5$, O—[C(R$^5$)$_2$]$_n$—cycloalkylene-[C(R$^5$)$_2$]$_n$—N(R$^5$)$_2$, [C(R$^5$)$_2$]$_n$NR$^5$COOA or CH=CH—COOR$^5$, or a pharmaceutically acceptable salt, tautomer or stereoisomer thereof.

5. A compound according to claim 1, in which

R$^3$, R$^{3'}$ each, independently of one another, denote H or R$^8$, or a pharmaceutically acceptable salt, tautomer or stereoisomer thereof.

6. A compound according to claim 1, in which

R$^4$, R$^6$ denote H, or a pharmaceutically acceptable salt, tautomer or stereoisomer thereof.

7. A compound according to claim 1, in which

R$^1$ denotes H, Hal, A, OR$^5$, S(O)$_m$A, or a heterocycle selected from the group consisting of thiazolyl, thiophenyl, furanyl, pyrrolyl, oxazolyl, isoxazolyl, oxadiazolyl, pyrazolyl, imidazolyl, thiadiazolyl, pyridazinyl, pyrazinyl, pyridinyl, pyrimidinyl, and pyrazolyloxy, which heterocycle is optionally mono-, di- or trisubstituted by Hal, A and/or O[C(R$^5$)$_2$]$_p$-OR$^5$, or phenyl or phenoxy, each of which is mono-, di- or tri-substituted by Hal and/or CN, or a pharmaceutically acceptable salt, tautomer or stereoisomer thereof.

8. A compound according to claim 1, in which

Het denotes a monocyclic saturated, unsaturated or aromatic heterocycle having 1 to 4 N, O and/or S atoms, which is unsubstituted or mono-, di- or trisubstituted by Hal, A, COOR$^5$, O[C(R$^5$)$_2$]$_p$OR$^5$, [C(R$^5$)$_2$]$_n$Het$^1$, O[C(R$^5$)$_2$]$_n$Het$^1$ and/or =O(carbonyl oxygen), or a pharmaceutically acceptable salt, tautomer or stereoisomer thereof.

9. A compound according to claim 1, in which

Het denotes piperidinyl, pyrrolidinyl, morpholinyl, piperazinyl, oxazolidinyl, pyrazolyl, pyridinyl, pyrimidinyl, furyl, thienyl, oxazolyl, oxadiazolyl, imidazolyl, pyrrolyl, isoxazolyl or imidazolidinyl, which is optionally mono- or disubstituted by Hal, A, COOR$^5$, O[C(R$^5$)$_2$]$_p$OR$^5$, [C(R$^5$)$_2$]$_n$Het$^1$, O [C(R$^5$)$_2$]$_n$Het$^1$ and/or =O, or a pharmaceutically acceptable salt, tautomer or stereoisomer thereof.

10. A compound according to claim 1, in which

Het$^1$ denotes piperidinyl, pyrrolidinyl, morpholinyl, piperazinyl, oxazolidinyl or imidazolidinyl, which is optionally mono- or disubstituted by COOA, =O and/or A, or a pharmaceutically acceptable salt, tautomer or stereoisomer thereof.

11. A compound according to claim 1, in which

Ar denotes phenyl, which is unsubstituted or mono-, di- or trisubstituted by Hal, A and/or CN, or a pharmaceutically acceptable salt, tautomer or stereoisomer thereof.

12. A compound according to claim 1, in which

A denotes unbranched or branched alkyl having 1-10 C atoms, in which 1-7 H atoms are optionally replaced by OH, F, Cl and/or Br, or cyclic alkyl having 3-7 C atoms, which is optionally monosubstituted by OH, or a pharmaceutically acceptable salt, tautomer or stereoisomer thereof.

13. A compound according to claim 1, in which

X$^1$, X$^2$, X$^3$, X$^4$, X$^5$ each, independently of one another, denote CH or N, R$^1$ denotes H, Hal, A, S(O)$_m$A, Ar, Het, O[C(R$^5$)$_2$]$_n$Ar, O[C(R$^5$)$_2$]$_n$Het or OR$^5$, R$^7$ denotes H or Hal, R$^2$ denotes A, Hal, [C(R$^5$)$_2$]$_n$N(R$^5$)$_2$, [C(R$^5$)$_2$]$_n$Het, O[C(R$^5$)$_2$]$_p$N(R$^5$)$_2$, O[C(R$^5$)$_2$]$_n$Het, [C(R$^5$)$_2$]$_n$OR$^5$, O[C(R$^5$)$_2$]$_p$OR$^5$, O—[C(R$^5$)$_2$]$_n$-cycloalkylene-[C(R$^5$)$_2$]$_n$—N(R$^5$)$_2$, [C(R$^5$)$_2$]$_n$NR$^5$COOA or CH=CH—COOR$^5$, R$^3$, R$^{3'}$ each, independently of one another, denote H or R$^8$, R$^4$, R$^6$ denote H, R$^5$ denotes H or R$^8$, R$^8$ denotes unbranched or branched alkyl having 1-6 C atoms, A denotes unbranched or branched alkyl having 1-10 C atoms, in which 1-7 H atoms are optionally replaced by OH, F, Cl and/or Br, or cyclic alkyl having 3-7 C atoms, which is optionally monosubstituted by OH, Ar denotes phenyl, which is unsubstituted or mono-, di- or trisubstituted by Hal, A and/or CN, Het denotes a monocyclic saturated, unsaturated or aromatic heterocycle having 1 to 4 N, O and/or S atoms, which is unsubstituted or mono-, di- or trisubstituted by Hal, A, COOR$^5$, O[C(R$^5$)$_2$]$_p$OR$^5$, [C(R$^5$)$_2$]$_n$Het$^1$, O[C(R$^5$)$_2$]$_n$Het$^1$ and/or =O, Het$^1$ denotes piperidinyl, pyrrolidinyl, morpholinyl, piperazinyl, oxazolidinyl or imidazolidinyl, which is optionally mono- or disubstituted by COOA, =O and/or A, Hal denotes F, Cl, Br or I, m denotes 0, 1 or 2, n denotes 0, 1, 2, 3 or 4, and p denotes 1, 2, 3 or 4, or a pharmaceutically acceptable salt, tautomer or stereoisomer thereof.

14. A compound, which is one of the following compounds

| No. | Structure or name |
|---|---|
| "A1" | 6-Bromo-1-{3-[5-(2-morpholin-4-ylethoxy)pyrimidin-2-yl]-benzyl}-1H-1,2,3-triazolo[4,5-b]pyrazine |
| "A2" | 6-(1-Methyl-1H-pyrazol-4-yl)-1-{3-[5-(2-morpholin-4-yl-ethoxy)pyrimidin-2-yl]benzyl}-1H-1,2,3-triazolo[4,5-b]- |

| No. | Structure or name |
|---|---|
| "A3" | pyrazine 1-{3-[5-(2-Morpholin-4-ylethoxy)pyrimidin-2-yl]benzyl}-1H-benzotriazole |
| "A4" | |
| "A5" | |
| "A6" | |
| "A7" | |
| "A8" | |
| "A9" | |

-continued

| No. | Structure or name |
|---|---|
| "A10" | |
| "A11" | |
| "A12" | |
| "A13" | |
| "A14" | |
| "A15" | |

-continued
| No. | Structure or name |
|---|---|
| "A16" | 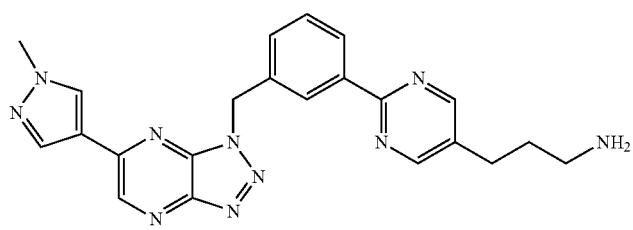 [SMILES: Cn1cc(-c2cnc3nnn(Cc4cccc(-c5ncc(CCCN)cn5)c4)c3n2)cn1] |
| "A17" | 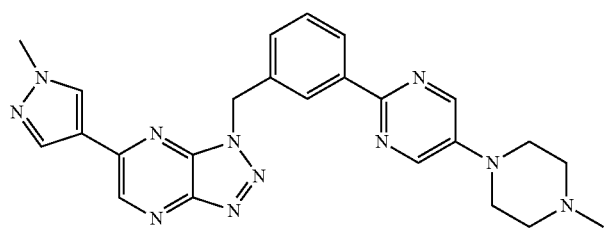 [SMILES: CN1CCN(c2cnc(-c3cccc(Cn4nnc5ncc(-c6cnn(C)c6)nc54)c3)nc2)CC1] |
| "A18" | 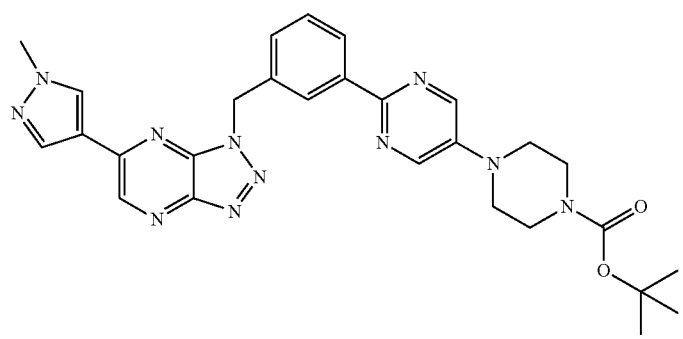 [SMILES: Cn1cc(-c2cnc3nnn(Cc4cccc(-c5ncc(N6CCN(C(=O)OC(C)(C)C)CC6)cn5)c4)c3n2)cn1] |
| "A19" | 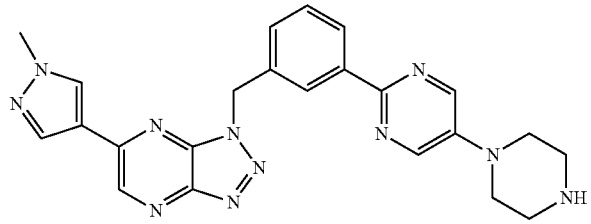 [SMILES: Cn1cc(-c2cnc3nnn(Cc4cccc(-c5ncc(N6CCNCC6)cn5)c4)c3n2)cn1] |
| "A20" | 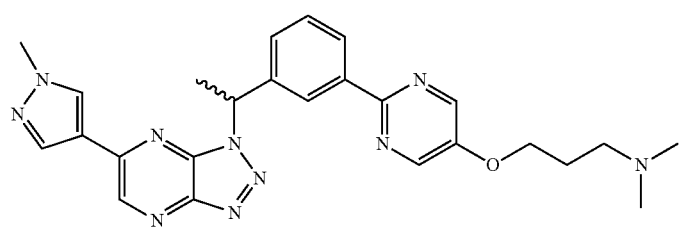 [SMILES: CC(c1cccc(-c2ncc(OCCCN(C)C)cn2)c1)n1nnc2ncc(-c3cnn(C)c3)nc21] |
| "A21" | 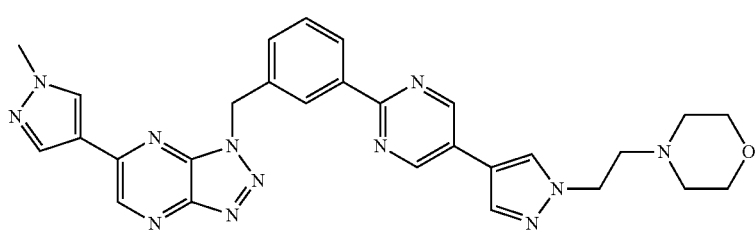 [SMILES: Cn1cc(-c2cnc3nnn(Cc4cccc(-c5ncc(-c6cnn(CCN7CCOCC7)c6)cn5)c4)c3n2)cn1] |

| No. | Structure or name |
|---|---|
| "A22" | |
| "A23" | |
| "A24" | |
| "A25" | |
| "A26" | |
| "A27" | |

| No. | Structure or name |
|---|---|
| "A28" | 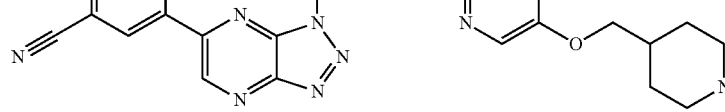 |
| "A29" | 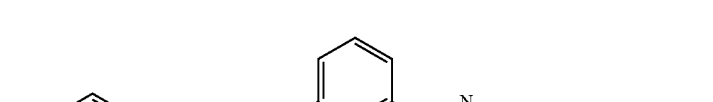 |
| "A30" | 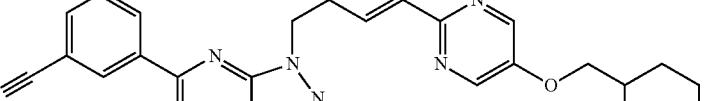 |
| "A31" |  |
| "A32" |  |
| "A33" | 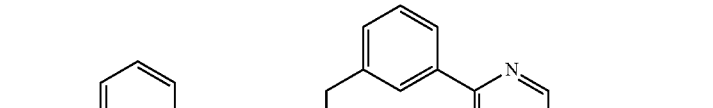 |

| No. | Structure or name |
|---|---|
| "A34" | |
| "A35" | |
| "A36" | |
| "A37" | |
| "A38" | |
| "A39" | |

-continued
| No. | Structure or name |
|---|---|
| "A40" | 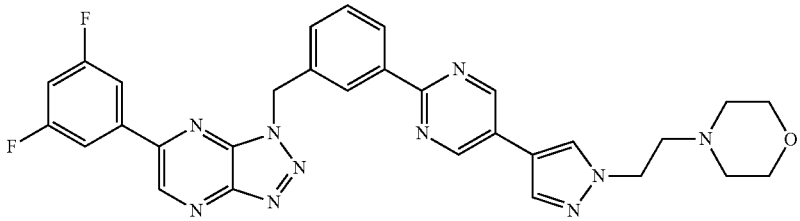 [SMILES: Fc1cc(F)cc(-c2cnc3nnn(Cc4cccc(-c5ncc(-c6cnn(CCN7CCOCC7)c6)cn5)c4)c3n2)c1] |
| "A41" | 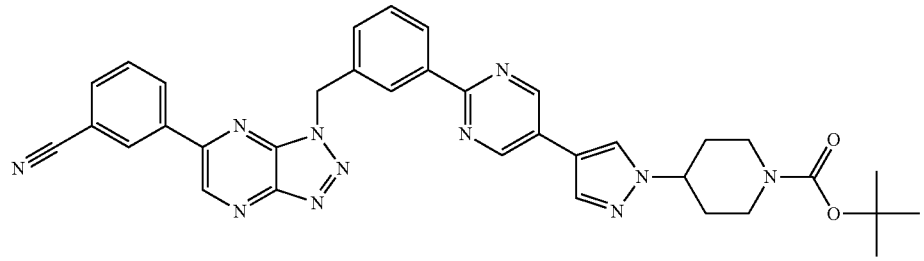 [SMILES: CC(C)(C)OC(=O)N1CCC(n2cc(-c3cnc(-c4cccc(Cn5nnc6ncc(-c7cccc(C#N)c7)nc65)c4)nc3)cn2)CC1] |
| "A42" | 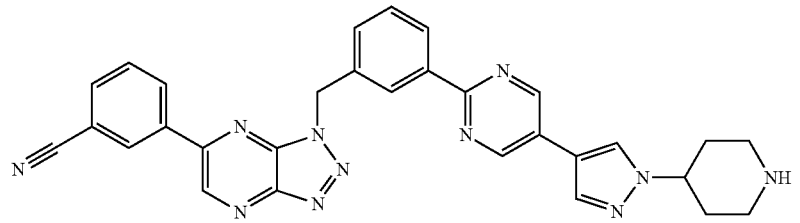 [SMILES: N#Cc1cccc(-c2cnc3nnn(Cc4cccc(-c5ncc(-c6cnn(C7CCNCC7)c6)cn5)c4)c3n2)c1] |
| "A43" | 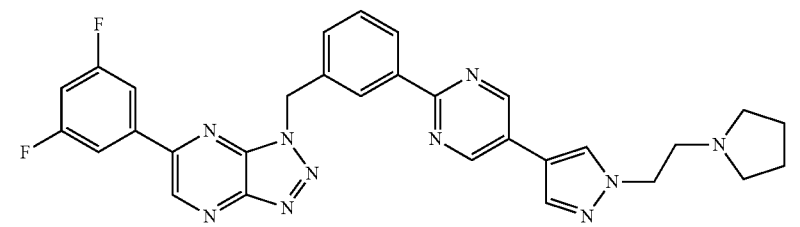 [SMILES: Fc1cc(F)cc(-c2cnc3nnn(Cc4cccc(-c5ncc(-c6cnn(CCN7CCCC7)c6)cn5)c4)c3n2)c1] |
| "A44" | 3-{3-[5-(2-Morpholin-4-ylethoxy)pyrimidin-2-yl]benzyl}-3H-1,2,3-triazolo[4,5-b]pyridines |
| "A45" | 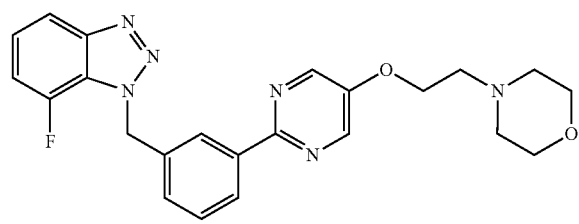 [SMILES: Fc1cccc2nnn(Cc3cccc(-c4ncc(OCCN5CCOCC5)cn4)c3)c12] |
| "A46" | 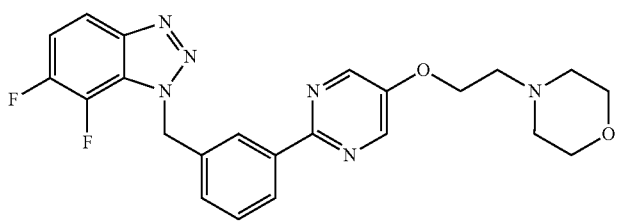 [SMILES: Fc1ccc2nnn(Cc3cccc(-c4ncc(OCCN5CCOCC5)cn4)c3)c2c1F] |

-continued

| No. | Structure or name |
|---|---|
| "A47" | (structure) |
| "A48" | (structure) |
| "A49" | (structure) |
| "A50" | (structure) |
| "A51" | 5-(1-Methyl-1H-pyrazol-4-yl)-3-{3-[5-(2-morpholin-4-yl-ethoxy)pyrimidin-2-yl]benzyl}-3H-1,2,3-triazolo[4,5-d]-pyrimidine |
| "A52" | (structure) |
| "A53" | (structure) |

| No. | Structure or name |
|---|---|
| "A54" | |
| "A55" | 1-{3-[5-(2-Morpholin-4-ylethoxy)pyrimidin-2-yl]benzyl}-6-(propane-1-sulfonyl)-1H-benzotriazole |
| "B1" | 6-Bromo-1-[3-(5-bromopyrimidin-2-yl)benzyl]-1H-1,2,3-triazolo[4,5-b]pyrazine |
| "B2" | 1-[3-(5-Bromopyrimidin-2-yl)benzyl]-6-(1-methyl-1H-pyrazol-4-yl)-1H-1,2,3-triazolo[4,5-b]pyrazine |
| "B3" | 3-{3-[3-(5-Bromopyrimidin-2-yl)benzyl]-3H-1,2,3-triazolo[4,5-b]pyrazin-5-yl}benzonitrile |
| "B4" | 1-[3-(5-Bromopyrimidin-2-yl)benzyl]-6-(3,5-difluoro-phenyl)-1H-1,2,3-triazolo[4,5-b]pyrazine |
| "B5" | 1-[3-(5-Bromopyrimidin-2-yl)benzyl]-6-(1-methyl-1H-pyrazol-4-yloxy)-1H-1,2,3-triazolo[4,5-b]pyrazine |
| "B6" | 3-{3[3-(5-Bromopyrimidin-2-yl)benzyl]-3H-1,2,3-triazolo[4,5-b]pyrazin-5-yloxy}benzonitrile |
| "B7" | 1-[3-(5-Bromopyrimidin-2-yl)benzyl]-6-(3,5-difluorophenoxy)-1H-1,2,3-triazolo[4,5-b]pyrazine |
| "B8" | 2-{3-[6-(1-Methyl-1H-pyrazol-4-yl)-1,2,3-triazolo[4,5-b]-pyrazin-1-ylmethyl]phenyl}pyrimidin-5-ol |
| "B9" | 2-{3-[3-(3-Hydroxylpyrimidin-2-yl)benzyl]-3H-1,2,3-triazolo[4,5-b]pyrazin-5-yl}benzonitrile |
| "B10" | 2-{3-[6-(3,5-Difluorophenyl)-1,2,3-triazolo[4,5-b]pyrazin-1-ylmethyl]phenyl}pyrimidin-5-ol |
| "B11" | 2-{3-[6-(1-Methyl-1H-pyrazol-4-yloxy)-1,2,3-triazolo-[4,5-b]pyrazin-1-ylmethyl]phenyl}pyrimidin-5-ol |
| "B12" | 3-{3-[3-(5-Hydroxypyrimidin-2-yl)benzyl]-3H-1,2,3-triazolo[4,5-b]pyrazin-5-yloxy}benzonitrile |
| "B13" | 2-{3-[6-(3,5-Difluorophenoxy)-1,2,3-triazolo[4,5-b]pyrazin-1-ylmethyl]phenyl}pyrimidin-5-ol |
| "B14" | Dimethyl-[2-(2-{3-[6-(1-methyl-1H-pyrazol-4-yl)-1,2,3-triazolo[4,5-b]pyrazin-1-ylmethyl]phenyl}pyrimidin-5-yloxy)ethyl]amine |
| "B15" | |
| "B16" | |
| "B17" | |
| "B18" | |

-continued

| No. | Structure or name |
|---|---|
| "B19" | |
| "B20" | |
| "B21" | |
| "B22" | |
| "B23" | |
| "B24" | |

-continued

| No. | Structure or name |
|---|---|
| "B25" | [structure] |
| "B26" | [structure] |
| "B27" | [structure] |
| "B28" | [structure] |
| "B29" | [structure] |
| "B30" | [structure] |

| No. | Structure or name |
|---|---|
| "B31" | |
| "B32" | |
| "B33" | |
| "B34" | |
| "B35" | 5-Chloro-1-{3-[5-(2-morpholin-4-ylethoxy)pyrimidin-2-yl]-benzyl}-1H-benzotriazole |
| "B36" | (5-Bromo-2-nitrophenyl)-{3-[5-(2-morpholin-4-ylethoxy)-pyrimidin-2-yl]benzyl}amine or |
| "B37" | | or a pharmaceutically acceptable salt, tautomer or stereoisomer thereof.

15. A process for preparing a compound of formula I according to claim 1 or a pharmaceutically acceptable salt, tautomer or stereoisomer thereof, comprising a) reacting a compound of formula II

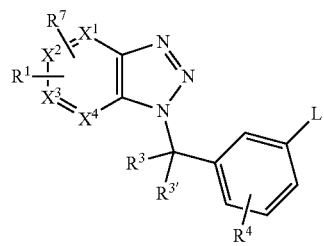

in which $X^1, X^2, X^3, X^4, R^1, R^3, R^{3'}, R^4$ and $R^7$ have the meanings indicated for the compound of formula I, and L denotes a boronic acid or boronic acid ester radical, with a compound of formula III

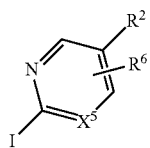

III in which $X^5, R^2$ and $R^6$ have the meanings indicated for the compound of formula I, or b) replacing a radical $R^1, R^2$ and/or $R^7$, which is a halogen atom, by a radical Het and/or Ar, which have the meanings indicated for the compound of formula I, or c) reacting a compound of formula IV

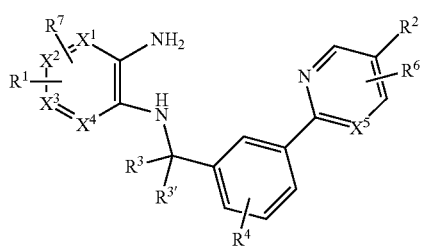

IV in which $X^1, X^2, X^3, X^4, X^5, R^1, R^2, R^3, R^{3'}, R^4, R^6$ and $R^7$ have the meanings indicated for the compound of formula I, with $NaNo_2$, and/or converting a base or acid compound of formula I into one of its salts.

16. A pharmaceutical composition comprising a compound of formula I according to claim 1 or a pharmaceutically acceptable salt, tautomer or stereoisomer thereof, and one or more pharmaceutically acceptable excipients and/or adjuvants.

17. A method for treating a disease which is influenced by inhibition of a Met kinase, comprising administering to a subject having said disease an effective amount of a compound of claim 1 or a pharmaceutically acceptable salt, tautomer or stereoisomer thereof.

18. A method according to claim 17, where the disease is a solid tumour.

19. A method according to claim 18, where the solid tumour originates from a tumor of the squamous epithelium, the bladder, the stomach, the kidneys, head and neck, the oesophagus, the cervix, the thyroid, the intestine, the liver, the brain, the prostate, the urogenital tract, the lymphatic system, the stomach, the larynx or the lung.

20. A method according to claim 18, where the solid tumour originates from monocytic leukaemia, lung adenocarcinoma, small-cell lung carcinoma, pancreatic cancer, glioblastoma or breast carcinoma.

21. A method according to claim 19, where the solid tumour originates from lung adenocarcinoma, small-cell lung carcinoma, pancreatic cancer, glioblastoma, colon carcinoma or breast carcinoma.

22. A method according to claim 17, where the disease is a tumour of the blood or immune system.

23. A method according to claim 22, where the tumour originates from acute myeloid leukaemia, chronic myeloid leukaemia, acute lymphatic leukaemia or chronic lymphatic leukaemia.

24. A pharmaceutical composition according to claim 16, further comprising a pharmaceutically active ingredient, which is not a compound of formula I.

25. A kit comprising separate packs of
  (a) a compound of formula I according to claim 1 or a pharmaceutically acceptable salt, tautomer or stereoisomer thereof,
  and
  (b) a pharmaceutically active ingredient, which is not a compound of formula I.

26. A method for treating a disease which is influenced by inhibition of a Met kinase, which is a solid tumor, comprising administering to a subject having said disease an effective amount of a compound of claim 14 or a pharmaceutically acceptable salt, tautomer or stereoisomer thereof.

* * * * *

UNITED STATES PATENT AND TRADEMARK OFFICE
CERTIFICATE OF CORRECTION

PATENT NO. : 8,435,986 B2  
APPLICATION NO. : 13/059016  
DATED : May 7, 2013  
INVENTOR(S) : Stieber et al.

Page 1 of 1

It is certified that error appears in the above-identified patent and that said Letters Patent is hereby corrected as shown below:

In the Claims:

Column 100, line 22 reads "$O[C(R^5)_2]_pOR^5, O[C(R^5)_2]_pN(R^5)_2, O[C(R^5)_2]_pN^+O^{31}$" should read -- $O[C(R^5)_2]_pOR^5, O[C(R^5)_2]_pN(R^5)_2, O[C(R^5)_2]_pN^+O^-$ --

Column 100, line 66 reads "$[C(R^5)_2]_pN(R^5)_2, NHCOO[C(R^5)_2]_nHet, NHCONH[C$" should read -- $[C(R^5)_2]_pN(R^5)_2, NHCOO[C(R^5)_2]_nHet^1, NHCONH[C$ --

Signed and Sealed this  
Thirtieth Day of July, 2013

Teresa Stanek Rea  
*Acting Director of the United States Patent and Trademark Office*